US012280055B2

(12) United States Patent
Haling et al.

(10) Patent No.: US 12,280,055 B2
(45) Date of Patent: Apr. 22, 2025

(54) COMBINATION THERAPIES

(71) Applicant: Mirati Therapeutics, Inc., San Diego, CA (US)

(72) Inventors: Jacob Haling, San Diego, CA (US); John Michael Ketcham, Carlsbad, CA (US); Shilpi Khare, San Diego, CA (US)

(73) Assignee: MIRATI THERAPEUTICS, INC., Princeton, NJ (US)

( * ) Notice: Subject to any disclaimer, the term of this patent is extended or adjusted under 35 U.S.C. 154(b) by 56 days.

(21) Appl. No.: 17/752,609

(22) Filed: May 24, 2022

(65) Prior Publication Data

US 2022/0395507 A1  Dec. 15, 2022

Related U.S. Application Data

(60) Provisional application No. 63/329,056, filed on Apr. 8, 2022, provisional application No. 63/194,140, filed on May 27, 2021.

(51) Int. Cl.
| | | |
|---|---|---|
| *A61K 31/519* | (2006.01) | |
| *A61K 31/502* | (2006.01) | |
| *A61K 31/5025* | (2006.01) | |
| *A61K 31/506* | (2006.01) | |
| *A61K 31/5377* | (2006.01) | |
| *A61K 31/5383* | (2006.01) | |
| *A61P 11/00* | (2006.01) | |
| *A61P 35/00* | (2006.01) | |

(52) U.S. Cl.
CPC .......... *A61K 31/519* (2013.01); *A61K 31/502* (2013.01); *A61K 31/5025* (2013.01); *A61K 31/506* (2013.01); *A61K 31/5377* (2013.01); *A61K 31/5383* (2013.01); *A61P 11/00* (2018.01); *A61P 35/00* (2018.01)

(58) Field of Classification Search
CPC ................ A61K 31/519; A61K 31/502; A61K 31/5025; A61K 31/506; A61K 31/5377; A61K 31/5383; A61P 11/00; A61P 35/00
See application file for complete search history.

(56) References Cited

U.S. PATENT DOCUMENTS

| | | | |
|---|---|---|---|
| 2019/0358230 A1 | 11/2019 | Gmachl | |
| 2020/0197391 A1 | 6/2020 | Jin | |
| 2021/0188857 A1 * | 6/2021 | Marx | C07D 487/04 |
| 2023/0233568 A1 * | 7/2023 | Hofmann | A61K 31/519 |

FOREIGN PATENT DOCUMENTS

| | | | | |
|---|---|---|---|---|
| WO | WO 2019/099524 A1 * | 5/2019 | | C07D 401/06 |
| WO | WO 2021/154929 A1 * | 8/2021 | | A61K 31/519 |
| WO | WO 2022/157629 A1 * | 7/2022 | | A61K 31/519 |

OTHER PUBLICATIONS

Canon, J., Rex, K., Saiki, A.Y. et al. The clinical KRAS(G12C) inhibitor AMG 510 drives anti-tumour immunity. Nature, 2020, 575: 217-223 (Year: 2020).*
International Search Report and Written Opinion for corresponding PCT Application No. PCT/US2022/030697 mailed Aug. 17, 2022.
International Preliminary Report for corresponding PCT Application No. PCT/US2022/030697 mailed Aug. 17, 2022.
Hillig et al. 'Discovery of potent SOS1 inhibitors that block RAS activation via disruption of the RAS-SOS1 interaction', PNAS, 2019, vol. 116, pp. 2551 2560. abstract; p. 2554, Fig 2; p. 2555, Fig 3; p. 2557, Fig 4; p. 2558, Fig 5F; p. 2559, col. 1, para 4.
Moore et al. 'RAS-targeted therapies: is the undruggable drugged?', Nat Rev Drug Discov. 2020, vol. 19(8), pp. 533-552. doi:10.1038/s41573-020-0068-6. abstract; p. 7, para 2.

* cited by examiner

*Primary Examiner* — Alicia L Otton
*Assistant Examiner* — David M Shim
(74) *Attorney, Agent, or Firm* — Roy Issac

(57) ABSTRACT

The present invention relates to combination therapies for treating KRas G12C cancers. In particular, the present invention relates to methods of treating cancer in a subject in need thereof, comprising administering to the subject a therapeutically effective amount of a combination of a SOS1 inhibitor and a KRas G12C inhibitor, pharmaceutical compositions comprising a such compositions, kits comprising such compositions and methods of use therefor.

34 Claims, 9 Drawing Sheets

Tumor Growth Inhitition of MIA PaCA-2 Tumor Bearing Mice Treated with MRTX0902 and in Combination with KRas G12C Inhibitor Adagrasib Tumor Growth Inhibition of MIA PaCA-2 Tumor Bearing Mice Treated with MRTX0902 and in Combination with KRas G12C Inhibitor Adagrasib Tumor Growth Inhitition of MIA PaCA-2 Tumor Bearing Mice Treated with MRTX2006 and in Combination with KRas G12C Inhibitor Adagrasib Tumor Growth Inhitition of MIA PaCA-2 Tumor Bearing Mice Treated with MRTX4197 and in Combination with KRas G12C Inhibitor Adagrasib Tumor Growth Inhitition of LU99 Tumor Bearing Mice Treated with MRTX0902 and in Combination with KRas G12C Inhibitor Adagrasib Tumor Growth Inhitition of NCI-H2122 Tumor Bearing Mice Treated with MRTX0902 and in Combination with KRas G12C Inhibitor Adagrasib Tumor Growth Inhitition of NCI-H2122 Tumor Bearing Mice Treated with MRTX0902 and in Combination with MEK Inhibitor VS-6766 and KRas G12C Inhibitor Adagrasib Tumor Growth Inhitition of CR6256 Tumor Bearing Mice Treated with MRTX0902 and in Combination with KRas G12C Inhibitor Adagrasib Breadth of Efficacy of MRTX0902 in Human Tumor Xenograft KRASG12C Models

COMBINATION THERAPIES

FIELD OF THE INVENTION

The present invention relates to combination therapies useful for treating cancer. In particular, the present invention relates to therapeutically effective combinations of a Son of sevenless homolog 1 (SOS1) inhibitor and a KRas G12C inhibitor, pharmaceutical compositions comprising the inhibitors, kits comprising the compositions and methods of use therefor.

BACKGROUND OF THE INVENTION

KRas Inhibitors

Kirsten Rat Sarcoma 2 Viral Oncogene Homolog ("KRas") is a small GTPase and a member of the Ras family of oncogenes. KRas serves as a molecular switch cycling between inactive (GDP-bound) and active (GTP-bound) states to transduce upstream cellular signals received from multiple tyrosine kinases to downstream effectors regulating a wide variety of processes, including cellular proliferation (e.g., see Alamgeer et al., (2013) Current Opin Pharmcol. 13:394-401).

The role of activated KRas in malignancy was observed over thirty years ago (e.g., see Der et al., (1982) Proc. Natl Acad. Sci. USA 79(11):3637-3640). Aberrant expression of KRas accounts for up to 20% of all cancers and oncogenic KRas mutations that stabilize GTP binding and lead to constitutive activation of KRas and downstream signaling have been reported in 25-30% of lung adenocarcinomas. (e.g., see Samatar and Poulikakos (2014) Nat Rev Drug Disc 13(12): 928-942 doi: 10.1038/nrd428). Single nucleotide substitutions that result in missense mutations at codons 12 and 13 of the KRas primary amino acid sequence comprise approximately 40% of these KRas driver mutations in lung adenocarcinoma, with a G12C transversion being the most common activating mutation (e.g., see Dogan et al., (2012) Clin Cancer Res. 18(22):6169-6177, published online 2012 Sep. 26. doi: 10.1158/1078-0432.CCR-11-3265).

The well-known role of KRas in malignancy and the discovery of these frequent mutations in KRas in various tumor types made KRas a highly attractable target of the pharmaceutical industry for cancer therapy. Notwithstanding thirty years of large scale discovery efforts to develop inhibitors of KRas for treating cancer, no KRas inhibitor has demonstrated sufficient safety and/or efficacy to obtain regulatory approval (e.g., see McCormick (2015) Clin Cancer Res. 21 (8):1797-1801).

Compounds that inhibit KRas activity are still highly desirable and under investigation, including those that disrupt effectors such as guanine nucleotide exchange factors (e.g., see Sun et al., (2012) Agnew Chem Int Ed Engl. 51(25):6140-6143 doi: 10.1002/anie201201358) as well as those that target KRas G12C (e.g., see Ostrem et al., (2013) Nature 503:548-551). Clearly there remains a continued interest and effort to develop inhibitors of KRas, particularly inhibitors of activating KRas mutants, including KRas G12C.

While the KRas G12C inhibitors disclosed herein are potent inhibitors of KRas G12C enzymatic activity and exhibit single agent activity inhibiting the in vitro proliferation of cell lines harboring a KRas G12C mutation, the relative potency and/or observed maximal effect of any given KRas G12C inhibitor can vary between KRas mutant cell lines. The reason or reasons for the range of potencies and observed maximal effect is not fully understood but certain cell lines appear to possess differing intrinsic resistance. Thus, there is a need to develop alternative approaches to maximize the potency, efficacy, therapeutic index and/or clinical benefit of KRas G12C inhibitors in vitro and in vivo.

SOS1 Inhibitors

The Ras family comprises v-Ki-ras2 Kirsten rat sarcoma viral oncogene homolog (KRas), neuroblastoma RAS viral oncogene homolog (NRAS), and Harvey murine sarcoma virus oncogene (HRas) and critically regulates cellular division, growth and function in normal and altered states including cancer (see e.g., Simanshu et al. Cell, 2017. 170(1): p. 17-33; Matikas et al., Crit Rev Oncol Hematol, 2017. 110: p. 1-12). RAS proteins are activated by upstream signals, including receptor tyrosine kinases (RTKs), and transduce signals to several downstream signaling pathways such as the mitogen-activated protein kinase (MAPK)/extracellular signal-regulated kinases (ERK) pathway. Hyperactivation of RAS signaling is frequently observed in cancer as a result of mutations or alterations in RAS genes or other genes in the RAS pathway. The identification of strategies to inhibit RAS and RAS signaling are predicted to be useful for the treatment of cancer and RAS-regulated disease states.

RAS proteins are guanosine triphosphatases (GTPases) that cycle between an inactive, guanosine diphosphate (GDP)-bound state and an active guanosine triphosphate (GTP)-bound state. RAS proteins exhibit both intrinsic GTP hydrolysis and nucleotide exchange, which is further enhanced by extrinsic GTPase activating proteins (GAPs) and guanine echange factors (GEFs). Son of sevenless homolog 1 (SOS1) is a GEF that mediates the exchange of GDP for GTP, thereby activating RAS proteins. This regulation through GAPs and GEFs is the mechanism whereby activation and deactivation are tightly regulated under normal conditions. Mutations at several residues in all three RAS proteins are frequently observed in cancer and result in RAS remaining predominantly in the activated state (Sanchez-Vega et al., Cell, 2018. 173: p. 321-337 Li et al., Nature Reviews Cancer, 2018. 18: p. 767-777). Mutations at codon 12 and 13 disrupt the GTP hydrolysis and exchange rate of RAS proteins. Recent biochemical analyses demonstrated these mutated proteins still require nucleotide cycling for activation based on their intrinsic GTPase activity and may exhibit partial sensitivity to extrinsic GAPs and GEFs. As such, mutant RAS proteins are sensitive to inhibition of upstream factors such as the SOS1 GEF (Hillig, 2019; Patricelli, 2016; Lito, 2016; Nichols, 2018).

The three main RAS-GEF families that have been identified in mammalian cells are SOS, RAS-GRF and RAS-GRP (Rojas, 2011). RAS-GRF and RAS-GRP are expressed in the cells of the central nervous system and hematopoietic cells, respectively, while the SOS family is ubiquitously expressed and is responsible for transducing RTK signaling. The SOS family comprises SOS1 and SOS2 and these proteins share approximately 70% sequence identity. SOS1 appears to be much more active than SOS2 due to the rapid degradation of SOS2. The mouse SOS2 knockout is viable whereas the SOS1 knockout is embryonic lethal. A tamoxifen-inducible SOS1 knockout mouse model was used to interrogate the role of SOS1 and SOS2 in adult mice and demonstrated the SOS1 knockout was viable but the SOS1/2 double knockout was not viable (Baltanas, 2013) suggesting functional redundancy and that selective inhibition of SOS1 may have a sufficient therapeutic index for the treatment of SOS1—RAS activated diseases.

SOS proteins are recruited to phosphorylated RTKs through an interaction with growth factor receptor bound protein 2 (GRB2). Recruitment to the plasma membrane places SOS in close proximity to RAS and enables SOS-mediated RAS activation. SOS proteins bind to RAS through a catalytic binding site that promotes nucleotide exchange as well as through an allosteric site that binds GTP-bound RAS-family proteins which increases the catalytic function of SOS (Freedman et al., Proc. Natl. Acad. Sci, USA 2006. 103(45): p. 16692-97). Binding to the allosteric site relieves steric occlusion of the catalytic site and is therefore required for full activation of the catalytic site. Retention of the active conformation at the catalytic site following interaction with the allosteric site is maintained in isolation due to strengthened interactions of key domains in the activated state. SOS1 mutations are found in Noonan syndrome and several cancers including lung adenocarcinoma, embryonal rhabdomyosarcoma, Sertoli cell testis tumor and granular cell tumors of the skin (see e.g., Denayer, E., et al, Genes Chromosomes Cancer, 2010. 49(3): p. 242-52).

GTPase-activating proteins (GAPs) are proteins that stimulate the low intrinsic GTPase activity of RAS family members and therefore converts active GTP-bound RAS proteins into inactive, GDP-bound RAS proteins (e.g., see Simanshu, D. K., Cell, 2017, Ras Proteins and their Regulators in Human Disease). While activating alterations in the phosphatase PTPN11(SHP2) and the GEF SOS1 occur in cancers, inactivating mutations and loss-of-function alterations in the GAP neurofibromin 1 (NF-1) also occur creating a state where SOS1 activity is unopposed and activity downstream of the pathway through RAS proteins is elevated.

MEK Inhibitors

The mitogen-activated protein kinase (MAPK) signaling pathway is involved in the regulation of various cellular activities, including, but not limited to cell proliferation, survival, differentiation, and motility. The classical MAPK pathway consists of Ras (a family of related proteins which is expressed in all animal cell lineages and organs), Raf (a family of three serine/threonine-specific protein kinases that are related to retroviral oncogenes), MEK (mitogen-activated protein kinase kinase), and ERK (extracellular signal-regulated kinases), sequentially relaying proliferative signals generated at the cell surface receptors into the nucleus through cytoplasmic signaling.

MEK inhibitors target the Ras/Raf/MEK/ERK signaling pathway, thereby inhibiting cell proliferation and inducing apoptosis.

The MAPK pathway is one of the most commonly mutated oncogenic pathways in cancer, Deregulation of this pathway is frequently observed and plays a central role in the carcinogenesis and maintenance of several cancers, including melanoma, pancreatic, lung, colorectal, and breast cancers. (e.g., Neuzillet et al., (2014) Pharmacology & Therapeutics 141:160-171).

Several inhibitors exhibiting activity against MEK have been developed, and a number of these inhibitors are or have been investigated in human clinical trials. Examples of MEK inhibitors suitable for the provided compositions and methods include, but are not limited to selumetinib, 6-(4-bromo-2-chloroanilino)-7-fluoro-N-(2-hydroxyethoxy)-3-methylbenzimidazole-5-carboxamide; AZD8330, 2-(2-fluoro-4-iodoanilino)-N-(2-hydroxyethoxy)-1,5-dimethyl-6-oxopyridine-3-carboxamide; PD0325901, N-[(2R)-2,3-dihydroxypropoxy]-3,4-difluoro-2-(2-fluoro-4-iodoanilino)benzamide; PD318088, 5-bromo-N-(2,3-dihydroxypropoxy)-3,4-difluoro-2-(2-fluoro-4-iodoanilino)benzamide; refametinib, N-[3,4-difluoro-2-(2-fluoro-4-iodoanilino)-6-methoxyphenyl]-1-[(2S)-2,3-dihydroxypropyl]cyclopropane-1-sulfonamide; binimetinib, 6-(4-bromo-2-fluoroanilino)-7-fluoro-N-(2-hydroxyethoxy)-3-methylbenzimidazole-5-carboxamide; RO4987655, 3,4-difluoro-2-(2-fluoro-4-iodoanilino)-N-(2-hydroxyethoxy)-5-[(3-oxooxazinan-2-yl)methyl]benzamide, RO5126766 (VS-6766), 3-[[3-fluoro-2-(methylsulfamoylamino)pyridin-4-yl]methyl]-4-methyl-7-pyrimidin-2-yloxychromen-2-one; WX-554, HL-085; ClnQ-03; G-573, 7-fluoro-3-(2-fluoro-4-iodoanilino)-N-[(2S)-2-hydroxypropoxy]furo[3,2-c]pyridine-2-carboxamide; PD184161, 5-bromo-2-(2-chloro-4-iodoanilino)-N-(cyclopropylmethoxy)-3,4-difluorobenzamide; RO5068760, (2S,3S)-2-[(4R)-4-[4-[(2R)-2,3-dihydroxypropoxy]phenyl]-2,5-dioxoimidazolidin-1-yl]-N-(2-fluoro-4-iodophenyl)-3-phenylbutanamide; SL327, (Z)-3-amino-3-(4-aminophenyl)sulfanyl-2-[2-(trifluoromethyl)phenyl]prop-2-enenitrile; MEK162 (Arry-162), 5-((4-bromo-2-fluorophenyl)amino)-4-fluoro-N-(2-hydroxyethoxy)-1-methyl-1H-benzo[d]imidazole-6-carboxamide; Tak-733, (R)-3-(2,3-dihydroxypropyl)-6-fluoro-5-((2-fluoro-4-iodophenyl)amino)-8-methylpyrido[2,3-d]pyrimidine-4,7(3H,8H)-dione; GDC-0623, 5-((2-fluoro-4-iodophenyl)amino)-N-(2-hydroxyethoxy)imidazo[1,5-a]pyridine-6-carboxamide; U0126, (2E,3E)-2-(amino((2-aminophenyl)thio)methylene)-3-(amino((3-aminophenyl)thio)methylene)succinonitrile; trametinib, N-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)acetamide; BI-847325, (E)-3-(3-(((4-((dimethylamino)methyl)phenyl)amino)(phenyl)methylene)-2-oxoindolin-6-yl)-N-ethylpropiolamide; pimasertib, (S)—N-(2,3-dihydroxypropyl)-3-((2-fluoro-4-iodophenyl)amino)isonicotinamide; BIX02189, (Z)-3-(((3-((dimethylamino)methyl)phenyl)amino)(phenyl)methylene)-N,N-dimethyl-2-oxoindoline-6-carboxamide; cobimetinib, (3,4-difluoro-2-((2-fluoro-4-iodophenyl)amino)phenyl)(3-hydroxy-3-(piperidin-2-yl)azetidin-1-yl)methanone; PD-98059, 2-(2-amino-3-methoxyphenyl)-4H-chromen-4-one; APS-2-79, 6,7-dimethoxy-N-(2-methyl-4-phenoxyphenyl)quinazolin-4-amine; PD 198306, N-(cyclopropylmethoxy)-3,4,5-trifluoro-2-(4-iodo-2-methylbenzyl)benzamide; CI-1040, 2-(2-chloro-4-iodobenzyl)-N-(cyclopropylmethoxy)-3,4-difluorobenzamide; SL327, (Z)-3-amino-3-((4-aminophenyl)thio)-2-(2-(trifluoromethyl)phenyl)acrylonitrile; and BIX02188, (Z)-3-(((3-((dimethylamino)methyl)phenyl)amino)(phenyl)methylene)-2-oxoindoline-6-carboxamide.

Structures of these MEK inhibitors can be found, for example, in Cheng et al, *Current Development Status of MEK Inhibitors*, Molecules 2017, 22, 1551, as well as in U.S. Pat. Nos. 10,370,374 and 10,323,035, as well as in US Patent Application Publication Nos: 20190144382; 20180370948; 20180296533; 20180147192; 20180118715; 20170231963; 20170183348; 20170183333; 20170166523; 20170101408; 20170096388; 20160331753; 20160168103; 20160168102; 20160136150; 20160108041; 20150141399; 20150133424; 20150051209; 20140378466; 20140275527; 20140135519; 20140128442; 20140080804; 20130150573; 20130018075; 20120238599; 20120208859; 20120107307; 20120022076; 20110288092; 20110263558; 20110190257; 20110183981; 20110172191; 20110158971; 20110124622; 20110112152; 20110060049; 20110021558; 20100331334; 20100267710; 20100261718; 20100261717; 20100260714; 20100256149; 20100249096; 20100197676; 20100179124; 20100063053; 20090291961; 20090264411; 20090233915; 20090215834; 20090209542; 20090156576; 20090149437;

20090143579; 20090143389; 20090131435; 20090082457; 20090030058; 20080306063; 20080280957; 20080255133; 20080177082; 20080171778; 20080166359; 20080058340; 20070299063; 20070293544; 20070287737; 20070287709; 20070244164; 20070238710; 20070213367; 20070172843; 20070112038; 20070105859; 20060211073; 20060194802; 20060189808; 20060189668; 20060189649; 20060154990; 20060106225; 20060089382; 20060052608; 20050256123; 20050250782 and 20050153942, the contents of which are hereby incorporated by reference in their entirety.

One of the MEK inhibitors suitable for the provided compositions and methods is VS-6766 which has the following structure:

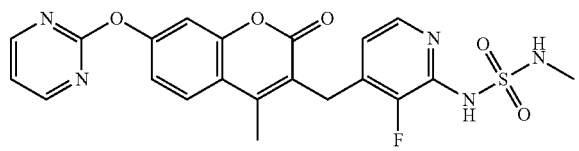 [SMILES: CNS(=O)(=O)Nc1nccc(Cc2c(C)c3ccc(Oc4ncccn4)cc3oc2=O)c1F]

3-[[3-fluoro-2-(methylsulfamoylamino)pyridin-4-yl]
methyl]-4-methyl-7-pyrimidin-2-yloxychromen-2-
one Methods for manufacturing MEK inhibitors, or pharmaceutically acceptable salts or pharmaceutical compositions thereof are well known to those skilled in the art and MEK inhibitors may be obtained from a wide-variety of commercial suppliers, in forms suitable for both research or human use. In addition, suitable MEK inhibitors for use in the compositions and methods disclosed herein and methods for preparing such inhibitors are disclosed in US Patent Application Publication Nos: 20190144382; 20180370948; 20180296533; 20180147192; 20180118715; 20170231963; 20170183348; 20170183333; 20170166523; 20170101408; 20170096388; 20160331753; 20160168103; 20160168102; 20160136150; 20160108041; 20150141399; 20150133424; 20150051209; 20140378466; 20140275527; 20140135519; 20140128442; 20140080804; 20130150573; 20130018075; 20120238599; 20120208859; 20120107307; 20120022076; 20110288092; 20110263558; 20110190257; 20110183981; 20110172191; 20110158971; 20110124622; 20110112152; 20110060049; 20110021558; 20100331334; 20100267710; 20100261718; 20100261717; 20100260714; 20100256149; 20100249096; 20100197676; 20100179124; 20100063053; 20090291961; 20090264411; 20090233915; 20090215834; 20090209542; 20090156576; 20090149437; 20090143579; 20090143389; 20090131435; 20090082457; 20090030058; 20080306063; 20080280957; 20080255133; 20080177082; 20080171778; 20080166359; 20080058340; 20070299063; 20070293544; 20070287737; 20070287709; 20070244164; 20070238710; 20070213367; 20070172843; 20070112038; 20070105859; 20060211073; 20060194802; 20060189808; 20060189668; 20060189649; 20060154990; 20060106225; 20060089382; 20060052608; 20050256123; 20050250782 and 20050153942.

SUMMARY OF THE INVENTION

The combination therapy of the present invention, in one aspect, synergistically increases the potency of KRas G12C inhibitors resulting in improved efficacy of KRas G12C inhibitors disclosed herein. The combination therapy of the present invention, in another aspect, provides improved clinical benefit to patients compared to treatment with KRas G12C inhibitors disclosed herein as a single agent.

Thus in one aspect of the invention there are provided therapeutically effective combinations of a SOS1 inhibitor such as those described in U.S. provisional patent applications 62/951,812, 62/975,645, 63/044,802, 62/980,790 and 63/057,563 (and corresponding U.S. and international applications and publications including PCT/US20/66003, PCT/US21/19184, PCT/US21/43309 and U.S. Ser. No. 17/127,582) as described in greater detail herein, for instance:

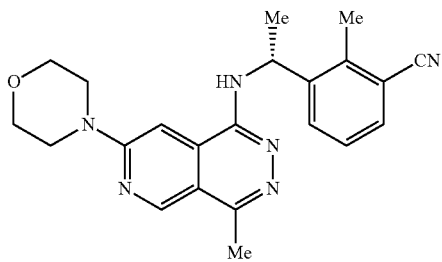 [SMILES: Cc1c(C#N)cccc1[C@@H](C)Nc1nnc(C)c2cnc(N3CCOCC3)cc12]

(R)-2-methyl-3-(1-((4-methyl-7-morpholinopyrido[3,4-d]
pyridazin-1-yl)amino)ethyl)benzonitrile,

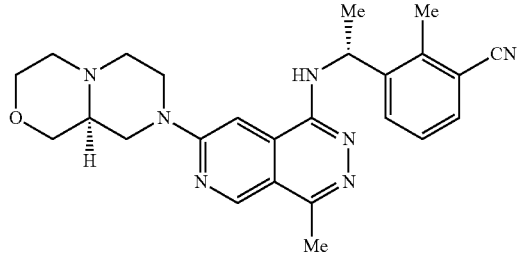 [SMILES: Cc1c(C#N)cccc1[C@@H](C)Nc1nnc(C)c2cnc(N3CCN4CCOC[C@@H]4C3)cc12]

3-((R)-1-((7-((S)-hexahydropyrazino[2,1-c][1,4]oxazin-8
(1H)-yl)-4-methylpyrido[3,4-d]pyridazin-1-yl)amino)
ethyl)-2-methylbenzonitrile,

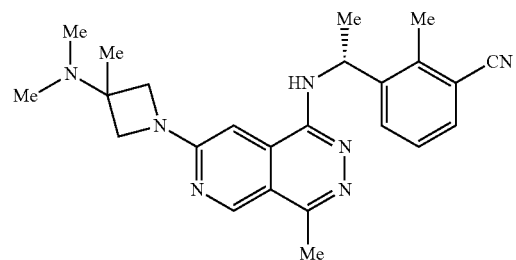 [SMILES: Cc1c(C#N)cccc1[C@@H](C)Nc1nnc(C)c2cnc(N3CC(C)(N(C)C)C3)cc12]

(R)-3-(1-((7-(3-(dimethylamino)-3-methylazetidin-1-yl)-4-methylpyrido[3,4-d]pyridazin-1-yl)amino)ethyl)-2-methylbenzonitrile, 3-((R)-1-((7-((S)-3-(dimethylamino)pyrrolidin-1-yl)-4-methylpyrido[3,4-d]pyridazin-1-yl)amino)ethyl)-2-methylbenzonitrile,

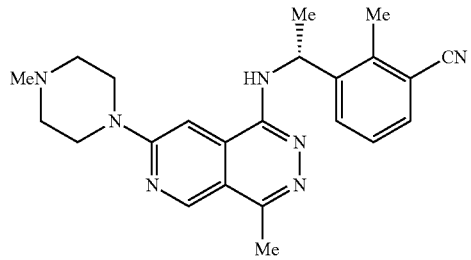 [SMILES: Cc1c(C#N)cccc1[C@@H](C)Nc1nnc(C)c2cnc(N3CCN(C)CC3)cc12]

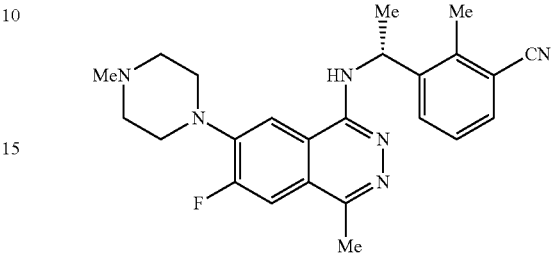

(R)-2-methyl-3-(1-((4-methyl-7-(4-methylpiperazin-1-yl)pyrido[3,4-d]pyridazin-1-yl)amino)ethyl)benzonitrile, (R)-3-(1-((6-fluoro-4-methyl-7-(4-methylpiperazin-1-yl)phthalazin-1-yl)amino)ethyl)-2-methylbenzonitrile, or a pharmaceutically acceptable salt thereof, and the KRas G12C inhibitor compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (also known as MRTX849, and also known as adagrasib):

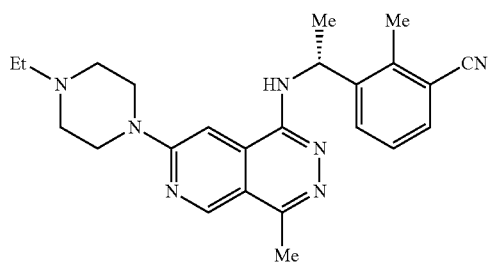 [SMILES: CCN1CCN(c2cc3c(N[C@H](C)c4cccc(C#N)c4C)nnc(C)c3cn2)CC1]

(R)-3-(1-((7-(4-ethylpiperazin-1-yl)-4-methylpyrido[3,4-d]pyridazin-1-yl)amino)ethyl)-2-methylbenzonitrile,

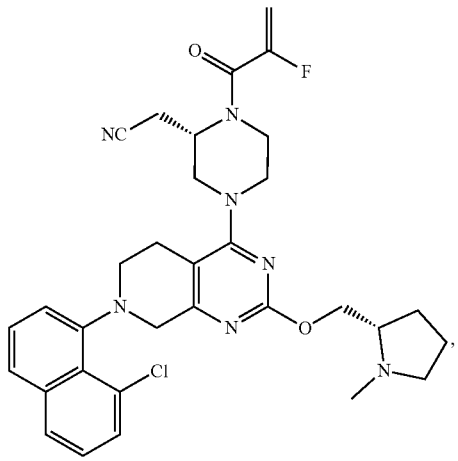

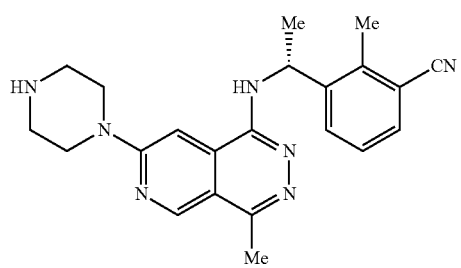 [SMILES: Cc1c(C#N)cccc1[C@@H](C)Nc1nnc(C)c2cnc(N3CCNCC3)cc12]

(R)-2-methyl-3-(1-((4-methyl-7-(piperazin-1-yl)pyrido[3,4-d]pyridazin-1-yl)amino)ethyl)benzonitrile,

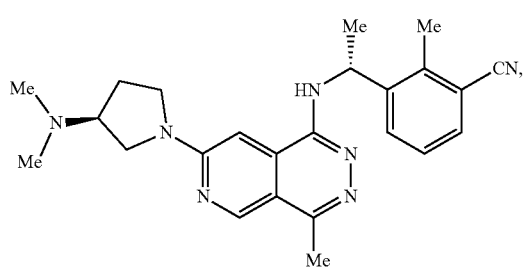 [SMILES: Cc1c(C#N)cccc1[C@@H](C)Nc1nnc(C)c2cnc(N3CC[C@H](N(C)C)C3)cc12]

or a pharmaceutically acceptable salt thereof.

In another aspect of the invention there are provided therapeutically effective combinations of a SOS1 inhibitor such as BI1701963 or a pharmaceutically acceptable salt thereof, and the KRas G12C inhibitor compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (also known as MRTX849, and also known as adagrasib):

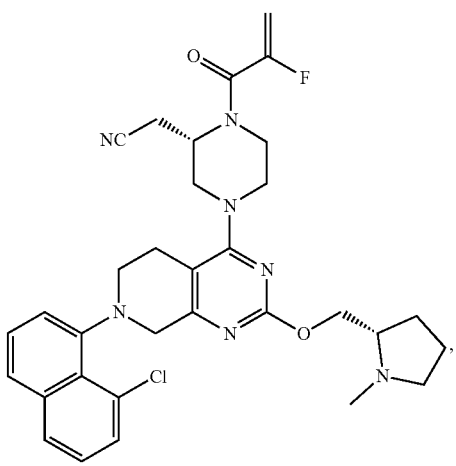

or a pharmaceutically acceptable salt thereof.

In one aspect, the invention provides a therapeutically effective combination of:

the SOS1 inhibitor (R)-2-methyl-3-(1-((4-methyl-7-morpholinopyrido[3,4-d]pyridazin-1-yl)amino)ethyl)benzonitrile (also known as MRTX0902), having the formula:

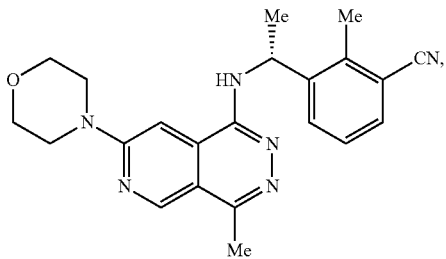 [SMILES: Cc1c(C#N)cccc1[C@@H](C)Nc1nnc(C)c2cnc(N3CCOCC3)cc12]

or a pharmaceutically acceptable salt thereof; and
a KRas G12C inhibitor compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (also known as MRTX849, and also known as adagrasib).

In another aspect, the invention provides a therapeutically effective combination of:

the SOS1 inhibitor (R)-2-methyl-3-(1-((4-methyl-7-morpholinopyrido[3,4-d]pyridazin-1-yl)amino)ethyl)benzonitrile (also known as MRTX0902), having the formula:

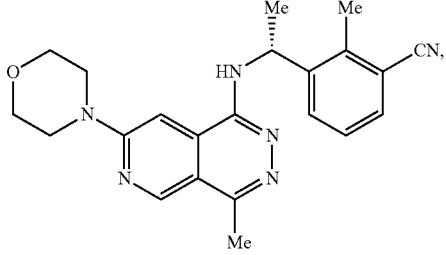 [SMILES: Cc1c(C#N)cccc1[C@@H](C)Nc1nnc(C)c2cnc(N3CCOCC3)cc12]

or a pharmaceutically acceptable salt thereof, a KRas G12C inhibitor compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (also known as MRTX849, and also known as adagrasib); and the MEK inhibitor [[3-fluoro-2-(methylsulfamoylamino)pyridin-4-yl]methyl]-4-methyl-7-pyrimidin-2-yloxychromen-2-one (also known as VS-6766) which has the following structure:

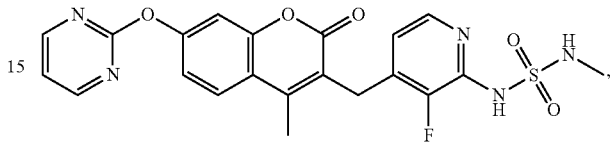

or a pharmaceutically acceptable salt thereof.

In another aspect of the invention, pharmaceutical compositions are provided for use in the methods comprising a therapeutically effective amount of a combination of a SOS1 inhibitor such as (R)-2-methyl-3-(1-((4-methyl-7-morpholinopyrido[3,4-d]pyridazin-1-yl)amino)ethyl)benzonitrile, 3-((R)-1-((7-((S)-hexahydropyrazino[2,1-c][1,4]oxazin-8(1H)-yl)-4-methylpyrido[3,4-d]pyridazin-1-yl)amino)ethyl)-2-methylbenzonitrile, (R)-3-(1-((7-(3-(dimethylamino)-3-methylazetidin-1-yl)-4-methylpyrido[3,4-d]pyridazin-1-yl)amino)ethyl)-2-methylbenzonitrile, (R)-2-methyl-3-(1-((4-methyl-7-(4-methylpiperazin-1-yl)pyrido[3,4-d]pyridazin-1-yl)amino)ethyl)benzonitrile, (R)-3-(1-((7-(4-ethylpiperazin-1-yl)-4-methylpyrido[3,4-d]pyridazin-1-yl)amino)ethyl)-2-methylbenzonitrile, (R)-2-methyl-3-(1-((4-methyl-7-(piperazin-1-yl)pyrido[3,4-d]pyridazin-1-yl)amino)ethyl)benzonitrile, 3-((R)-1-((7-((S)-3-(dimethylamino)pyrrolidin-1-yl)-4-methylpyrido[3,4-d]pyridazin-1-yl)amino)ethyl)-2-methylbenzonitrile or (R)-3-(1-((6-fluoro-4-methyl-7-(4-methylpiperazin-1-yl)phthalazin-1-yl)amino)ethyl)-2-methylbenzonitrile, or a SOS1 inhibitor such as BI1701963, and the KRas G12C inhibitor compound adagrasib, or a pharmaceutically acceptable salt thereof and a pharmaceutically acceptable excipient.

In some embodiments, the methods may further comprise administering MEK inhibitors to the subject in need thereof, so that the subject is being administered adagrasib, a SOS1 inhibitor, and a MEK inhibitor, for example VS-6766.

In one aspect of the invention, provided herein are methods of treating cancer in a subject in need thereof, comprising administering to the subject a therapeutically effective amount of a combination of a SOS1 inhibitor such as (R)-2-methyl-3-(1-((4-methyl-7-morpholinopyrido[3,4-d]pyridazin-1-yl)amino)ethyl)benzonitrile, 3-((R)-1-((7-((S)-hexahydropyrazino[2,1-c][1,4]oxazin-8(1H)-yl)-4-methylpyrido[3,4-d]pyridazin-1-yl)amino)ethyl)-2-methylbenzonitrile, (R)-3-(1-((7-(3-(dimethylamino)-3-methylazetidin-1-yl)-4-methylpyrido[3,4-d]pyridazin-1-yl)amino)ethyl)-2-methylbenzonitrile, (R)-2-methyl-3-(1-((4-methyl-7-(4-methylpiperazin-1-yl)pyrido[3,4-d]pyridazin-1-yl)amino)ethyl)benzonitrile, (R)-3-(1-((7-(4-ethylpiperazin-1-yl)-4-methylpyrido[3,4-d]pyridazin-1-yl)amino)ethyl)-2-methylbenzonitrile, (R)-2-methyl-3-(1-((4-methyl-7-(piperazin-1-yl)pyrido[3,4-d]pyridazin-1-yl)amino)ethyl)benzonitrile, 3-((R)-1-((7-((S)-3-(dimethylamino)pyrrolidin-1-yl)-4-methylpyrido[3,4-d]pyridazin-1-yl)amino)ethyl)-2-methylbenzonitrile or (R)-3-

(1-((6-fluoro-4-methyl-7-(4-methylpiperazin-1-yl)phthalazin-1-yl)amino)ethyl)-2-methylbenzonitrile, or a SOS1 inhibitor such as BI1701963, or a pharmaceutically acceptable salt or a pharmaceutical composition thereof and the KRas G12C inhibitor adagrasib, or a pharmaceutically acceptable salt or a pharmaceutical composition thereof.

In one embodiment, the cancer is a KRas G12C-associated cancer. In one embodiment, the KRas G12C-associated cancer is lung cancer.

In some aspects of the invention, KRas G12C inhibitor compounds and SOS1 inhibitors are the only active agents in the provided compositions and methods.

Examples of SOS1 inhibitors suitable for the provided compositions and methods include, but are not limited to (R)-2-methyl-3-(1-((4-methyl-7-morpholinopyrido[3,4-d]pyridazin-1-yl)amino)ethyl)benzonitrile, 3-((R)-1-((7-((S)-hexahydropyrazino[2,1-c][1,4]oxazin-8(1H)-yl)-4-methylpyrido[3,4-d]pyridazin-1-yl)amino)ethyl)-2-methylbenzonitrile, (R)-3-(1-((7-(3-(dimethylamino)-3-methylazetidin-1-yl)-4-methylpyrido[3,4-d]pyridazin-1-yl)amino)ethyl)-2-methylbenzonitrile, (R)-2-methyl-3-(1-((4-methyl-7-(4-methylpiperazin-1-yl)pyrido[3,4-d]pyridazin-1-yl)amino)ethyl)benzonitrile, (R)-3-(1-((7-(4-ethylpiperazin-1-yl)-4-methylpyrido[3,4-d]pyridazin-1-yl)amino)ethyl)-2-methylbenzonitrile, (R)-2-methyl-3-(1-((4-methyl-7-(piperazin-1-yl)pyrido[3,4-d]pyridazin-1-yl)amino)ethyl)benzonitrile, 3-((R)-1-((7-((S)-3-(dimethylamino)pyrrolidin-1-yl)-4-methylpyrido[3,4-d]pyridazin-1-yl)amino)ethyl)-2-methylbenzonitrile and (R)-3-(1-((6-fluoro-4-methyl-7-(4-methylpiperazin-1-yl)phthalazin-1-yl)amino)ethyl)-2-methylbenzonitrile, and pharmaceutically acceptable salts thereof.

Other examples of SOS1 inhibitors suitable for the provided compositions and methods include BI1701963.

In yet another aspect, the invention provides a method for inhibiting KRas G12C activity in a cell, comprising contacting the cell in which inhibition of KRas G12C activity is desired with an effective amount of a combination of the KRas G12C inhibitor adagrasib:

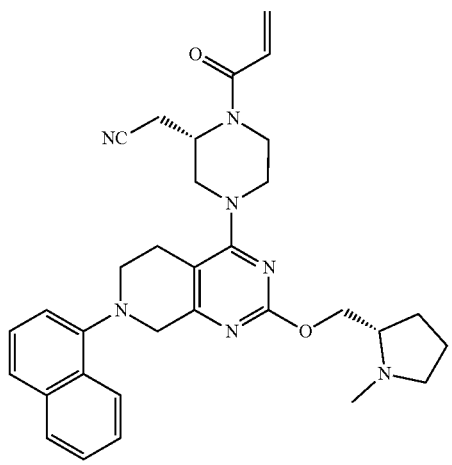

or a pharmaceutically acceptable salt thereof, and a SOS1 inhibitor.

In one embodiment, the SOS1 inhibitor has the following structure:

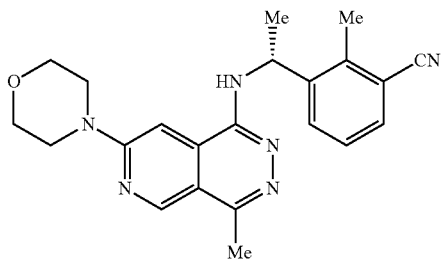 [SMILES: Cc1c(C#N)cccc1[C@@H](C)Nc1nnc(C)c2cnc(N3CCOCC3)cc12]

or a pharmaceutically acceptable salt thereof.

In yet another aspect, the method also comprises contacting the cell with a compound having the following structure:

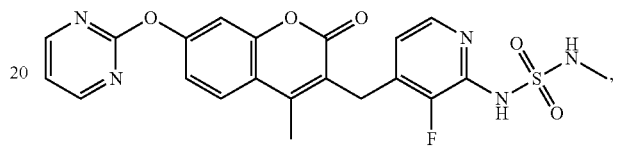

or a pharmaceutically acceptable salt thereof.

In yet another aspect, the invention provides for methods for increasing the sensitivity of a cancer cell to a KRas G12C inhibitor, comprising contacting the cancer cell with a therapeutically effective amount of a combination of the KRas G12C inhibitor compound adagrasib or a pharmaceutically acceptable salt or a pharmaceutical composition thereof, and a SOS1 inhibitor or a pharmaceutically acceptable salt or a pharmaceutical composition thereof, wherein the SOS1 inhibitor synergistically increases the sensitivity of the cancer cell to the KRas G12C inhibitor. In one embodiment, the contacting is in vitro. In one embodiment, the contacting is in vivo. In one embodiment, the method comprises administering to a subject undergoing KRas G12C treatment with an effective amount of a combination the KRas G12C inhibitor adagrasib or a pharmaceutically acceptable salt thereof, and a SOS1 inhibitor, wherein the SOS1 inhibitor synergistically increases the sensitivity of the cancer cell to the KRas G12C inhibitor.

In one embodiment, the method for increasing the sensitivity of a cancer cell to a KRas G12C inhibitor, comprises contacting the cancer cell with a therapeutically effective amount of a combination of the KRas G12C inhibitor compound adagrasib or a pharmaceutically acceptable salt or a pharmaceutical composition thereof, and a SOS1 inhibitor having the following structure:

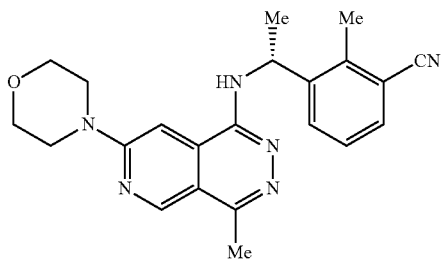 [SMILES: Cc1c(C#N)cccc1[C@@H](C)Nc1nnc(C)c2cnc(N3CCOCC3)cc12]

or a pharmaceutically acceptable salt thereof or a pharmaceutically acceptable salt or a pharmaceutical composition thereof.

In yet another embodiment, the method for increasing the sensitivity of a cancer cell to a KRas G12C inhibitor also comprises contacting the cancer cell with a compound having the following structure:

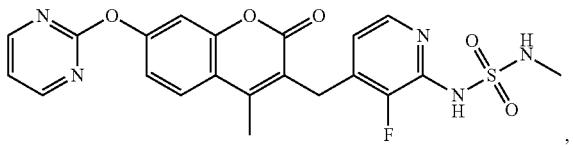 [SMILES: CNS(=O)(=O)Nc1nccc(Cc2c(C)c3ccc(Oc4ncccn4)cc3oc2=O)c1F]

or a pharmaceutically acceptable salt thereof.

Also provided herein are methods for treating cancer in a subject in need thereof, the method comprising (a) determining that cancer is associated with a KRas G12C mutation (e.g., a KRas G12C-associated cancer) (e.g., as determined using a regulatory agency-approved, e.g., FDA-approved, assay or kit); and (b) administering to the patient a therapeutically effective amount of a combination of a SOS1 inhibitor, or a pharmaceutically acceptable salt or a pharmaceutical composition thereof, and the KRas G12C inhibitor adagrasib or a pharmaceutically acceptable salt or a pharmaceutical composition thereof, wherein the SOS1 inhibitor synergistically increases the sensitivity of the KRas G12C-associated cancer to adagrasib.

Also provided herein are kits comprising a SOS1 inhibitor, or a pharmaceutically acceptable salt or a pharmaceutical composition thereof and the KRas G12C inhibitor compound adagrasib or a pharmaceutically acceptable salt or a pharmaceutical composition thereof. Also provided is a kit comprising a SOS1 inhibitor, or a pharmaceutically acceptable salt or a pharmaceutical composition thereof, and the KRas G12C inhibitor compound adagrasib or a pharmaceutically acceptable salt or a pharmaceutical composition thereof, for use in treating a KRas G12C cancer.

In a related aspect, the invention provides a kit containing a dose of a SOS1 inhibitor, or a pharmaceutically acceptable salt or a pharmaceutical composition thereof and the KRas G12C inhibitor compound adagrasib or a pharmaceutically acceptable salt or a pharmaceutical composition thereof in an amount effective to inhibit proliferation of cancer cells in a subject. The kit in some cases includes an insert with instructions for administration of a SOS1 inhibitor, or a pharmaceutically acceptable salt or a pharmaceutical composition thereof and the KRas G12C inhibitor compound adagrasib or a pharmaceutically acceptable salt or a pharmaceutical composition thereof. The insert may provide a user with one set of instructions for using the a SOS1 inhibitor or a pharmaceutically acceptable salt or a pharmaceutical composition thereof in combination with the KRas G12C inhibitor compound adagrasib or a pharmaceutically acceptable salt or a pharmaceutical composition thereof.

In some aspects of any of the methods described herein, before treatment with the compositions or methods of the invention, the patient was treated with one or more of a chemotherapy, a targeted anticancer agent, radiation therapy, and surgery, and optionally, the prior treatment was unsuccessful; and/or the patient has been administered surgery and optionally, the surgery was unsuccessful; and/or the patient has been treated with a platinum-based chemotherapeutic agent, and optionally, the patient has been previously determined to be non-responsive to treatment with the platinum-based chemotherapeutic agent; and/or the patient has been treated with a kinase inhibitor, and optionally, the prior treatment with the kinase inhibitor was unsuccessful; and/or the patient was treated with one or more other therapeutic agent(s).

DETAILED DESCRIPTION OF THE INVENTION

Figure 1:
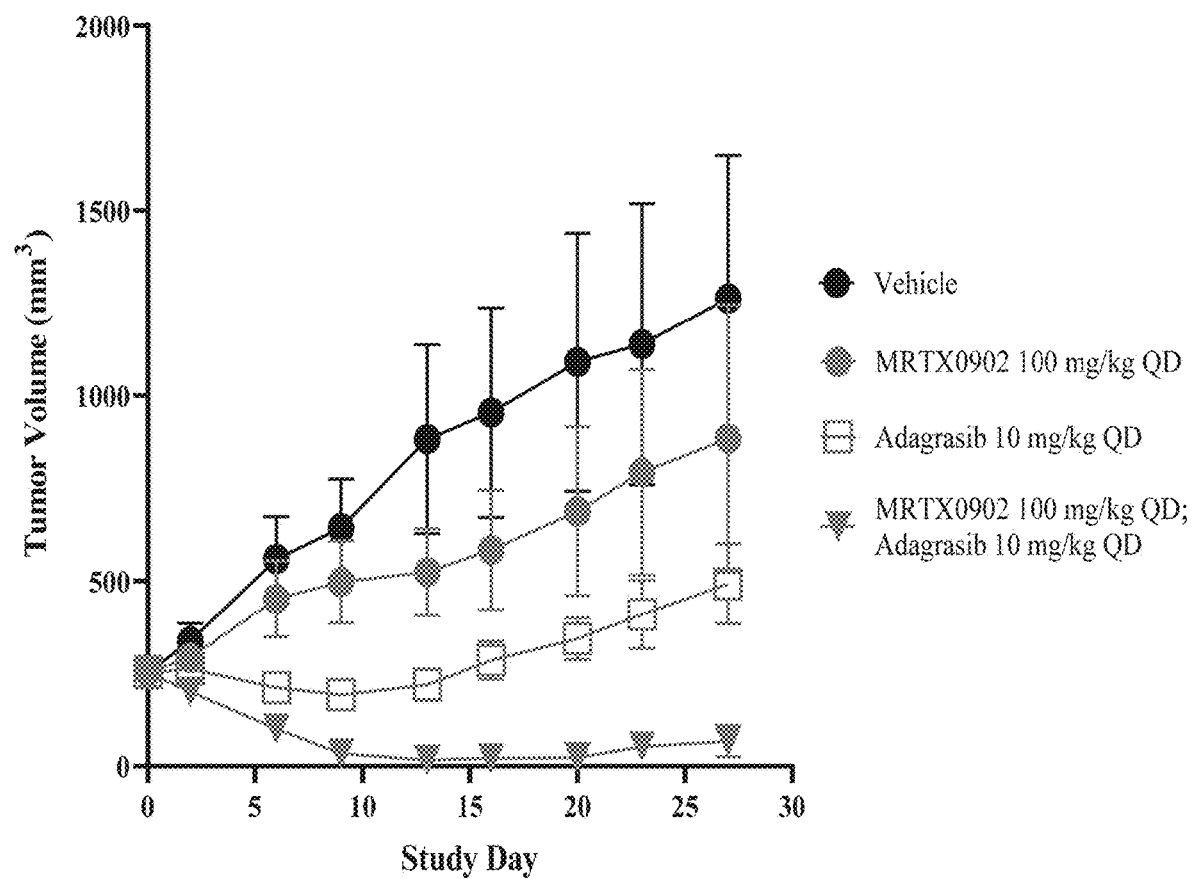
FIG. 1 is a chart of tumor growth inhibition of MIA PaCA-2 tumor bearing mice by MRTX0902, adagrasib, and a combination of MRTX0902 and adagrasib.

The present invention relates to combination therapies for treating KRas G12C cancers. In particular, the present invention relates to methods of treating cancer in a subject in need thereof, comprising administering to the subject a therapeutically effective amount of a combination of a SOS1 inhibitor or a pharmaceutically acceptable salt or a pharmaceutical composition thereof, and the KRas G12C inhibitor adagrasib or a pharmaceutically acceptable salt or a pharmaceutical composition thereof, pharmaceutical compositions comprising therapeutically effective amounts of the inhibitors, kits comprising the compositions and methods of use therefor.

Combinations of the SOS1 inhibitor, or a pharmaceutically acceptable salt or a pharmaceutical composition thereof, with a KRas G12C inhibitor, or a pharmaceutically acceptable salt or a pharmaceutical composition thereof, synergistically increase the potency of the KRas G12C inhibitor compound adagrasib against cancer cells that express KRas G12C thereby increasing the efficacy and therapeutic index of the KRas G12C inhibitor compound adagrasib or pharmaceutically acceptable salts thereof.

Definitions

Unless defined otherwise, all technical and scientific terms used herein have the same meaning as is commonly understood by one of skill in the art to which this invention belongs. All patents, patent applications, and publications referred to herein are incorporated by reference.

As used herein, "KRas G12C" refers to a mutant form of a mammalian KRas protein that contains an amino acid substitution of a cysteine for a glycine at amino acid position 12. The assignment of amino acid codon and residue positions for human KRas is based on the amino acid sequence identified by UniProtKB/Swiss-Prot P01116: Variant p.Gly12Cys.

As used herein, a "KRas G12C inhibitor" refers to compounds of the present invention that are represented by Formula (I), Formula I-A and Formula I-B as described in WO2019099524), or pharmaceutically acceptable salts thereof (e.g., Example Nos 234, 359, 478 or 507, or a pharmaceutically acceptable salt thereof). These compounds are capable of negatively modulating or inhibiting all or a portion of the enzymatic activity of KRas G12C. The KRas G12C inhibitors of the present invention interact with and irreversibly bind to KRas G12C by forming a covalent adduct with the sulfhydryl side chain of the cysteine residue at position 12 resulting in the inhibition of the enzymatic activity of KRas G12C. Adagrasib is an example of a KRas G12C inhibitor, A "KRas G12C-associated disease or disorder" as used herein refers to diseases or disorders associated with or mediated by or having a KRas G12C mutation. A non-limiting example of a KRas G12C-associated disease or disorder is a KRas G12C-associated cancer.

As used herein, "SOS1" refers to the Son of sevenless homolog 1 protein encoded by the SOS1 gene that is involved in signaling through RAS pathways.

As used herein, a "SOS1 inhibitor" refers to a compound that is capable of negatively modulating or inhibiting all or a portion of the interaction between KRAS and SOS1.

As used herein, the term "subject," "individual," or "patient," used interchangeably, refers to any animal, including mammals such as mice, rats, other rodents, rabbits, dogs, cats, swine, cattle, sheep, horses, primates, and humans. In some embodiments, the patient is a human. In some embodiments, the subject has experienced and/or exhibited at least one symptom of the disease or disorder to be treated and/or prevented. In some embodiments, the subject has been identified or diagnosed as having a cancer having a KRas G12C mutation (e.g., as determined using a regulatory agency-approved, e.g., FDA-approved, assay or kit). In some embodiments, the subject has a tumor that is positive for a KRas G12C mutation (e.g., as determined using a regulatory agency-approved assay or kit). The subject can be a subject with a tumor(s) that is positive for a KRas G12C mutation (e.g., identified as positive using a regulatory agency-approved, e.g., FDA-approved, assay or kit). The subject can be a subject whose tumors have a KRas G12C mutation (e.g., where the tumor is identified as such using a regulatory agency-approved, e.g., FDA-approved, kit or assay). In some embodiments, the subject is suspected of having a KRas G12C gene-associated cancer. In some embodiments, the subject has a clinical record indicating that the subject has a tumor that has a KRas G12C mutation (and optionally the clinical record indicates that the subject should be treated with any of the compositions provided herein).

The term "pediatric patient" as used herein refers to a patient under the age of 16 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E. Nelson Textbook of Pediatrics, 15th Ed. Philadelphia: W.B. Saunders Company, 1996; Rudolph A M, et al. Rudolph's Pediatrics, 21st Ed. New York: McGraw-Hill, 2002; and Avery M D, First L R. Pediatric Medicine, 2nd Ed. Baltimore: Williams & Wilkins; 1994.

In some embodiments of any of the methods or uses described herein, an assay is used to determine whether the patient has KRas G12C mutation using a sample (e.g., a biological sample or a biopsy sample such as a paraffin-embedded biopsy sample) from a patient (e.g., a patient suspected of having a KRas G12C-associated cancer, a patient having one or more symptoms of a KRas G12C-associated cancer, and/or a patient that has an increased risk of developing a KRas G12C-associated cancer) can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR, quantitative real-time RT-PCR, allele-specific genotyping or ddPCR). As is well-known in the art, the assays are typically performed, e.g., with at least one labelled nucleic acid probe or at least one labelled antibody or antigen-binding fragment thereof.

The term "regulatory agency" is a country's agency for the approval of the medical use of pharmaceutical agents with the country. For example, a non-limiting example of a regulatory agency is the U.S. Food and Drug Administration (FDA).

As used herein, "an effective amount" of a compound is an amount that is sufficient to negatively modulate or inhibit the activity of the desired target, i.e., SOS1 or KRas G12C. Such amount may be administered as a single dosage or may be administered according to a regimen, whereby it is effective.

As used herein, a "therapeutically effective amount" of a compound is an amount that is sufficient to ameliorate, or in some manner reduce a symptom or stop or reverse progression of a condition, or negatively modulate or inhibit the activity of SOS1 or KRas G12C. Such amount may be administered as a single dosage or may be administered according to a regimen, whereby it is effective.

As used herein, a "therapeutically effective amount of a combination" of two compounds is an amount that together synergistically increases the activity of the combination in comparison to the therapeutically effective amount of each compound in the combination, i.e., more than merely additive. Alternatively, in vivo, the therapeutically effective amount of the combination of a SOS1 inhibitor, or a pharmaceutically acceptable salt or a pharmaceutical composition thereof, and the KRas G12C inhibitor compound adagrasib or a pharmaceutically acceptable salt or a pharmaceutical composition thereof, results in an increased duration of overall survival ("OS") in subjects relative to treatment with only the KRas G12C inhibitor. In one embodiment, the therapeutically effective amount of the combination of a SOS1 inhibitor, or a pharmaceutically acceptable salt or a pharmaceutical composition thereof, and the KRas G12C inhibitor compound adagrasib or a pharmaceutically acceptable salt or a pharmaceutical composition thereof, results in an increased duration of progression-free survival ("PFS") in subjects relative to treatment with only the KRas G12C inhibitor. In one embodiment, the therapeutically effective amount of the combination of a SOS1 inhibitor, or a pharmaceutically acceptable salt or a pharmaceutical composition thereof, and the KRas G12C inhibitor compound adagrasib or a pharmaceutically acceptable salt or a pharmaceutical composition thereof, results in increased tumor regression in subjects relative to treatment with only the KRas G12C inhibitor. In one embodiment, the therapeutically effective amount of the combination of a SOS1 inhibitor, or a pharmaceutically acceptable salt or a pharmaceutical composition thereof, and the KRas G12C inhibitor compound adagrasib or a pharmaceutically acceptable salt or a pharmaceutical composition thereof, results in increased tumor growth inhibition in subjects relative to treatment with only the KRas G12C inhibitor. In one embodiment, the therapeutically effective amount of the combination of a SOS1 inhibitor, or a pharmaceutically acceptable salt or a pharmaceutical composition thereof, and the KRas G12C inhibitor compound adagrasib or a pharmaceutically acceptable salt or a pharmaceutical composition thereof, results in an improvement in the duration of stable disease in subjects compared to treatment with only the KRas G12C inhibitor. The amount of each compound in the combination may be the same or different than the therapeutically effective amount of each compound when administered alone as a monotherapy as long as the combination is synergistic. Such amounts may be administered as a single dosage or may be administered according to a regimen, whereby it is effective.

As used herein, "treatment" means any manner in which the symptoms or pathology of a condition, disorder or disease are ameliorated or otherwise beneficially altered. Treatment also encompasses any pharmaceutical use of the compositions herein.

As used herein, "amelioration" of the symptoms of a particular disorder by administration of a particular pharmaceutical composition refers to any lessening, whether permanent or temporary, lasting or transient that can be attributed to or associated with administration of the composition.

As used herein, the term "about" when used to modify a numerically defined parameter (e.g., the dose of a KRas inhibitor or a SOS1 inhibitor or a pharmaceutically acceptable salt thereof, or the length of treatment time with a combination therapy described herein) means that the parameter may vary by as much as 10% below or above the stated numerical value for that parameter. For example, a dose of about 5 mg/kg may vary between 4.5 mg/kg and 5.5 mg/kg. "About" when used at the beginning of a listing of parameters is meant to modify each parameter. For example, about 0.5 mg, 0.75 mg or 1.0 mg means about 0.5 mg, about 0.75 mg or about 1.0 mg. Likewise, about 5% or more, 10% or more, 15% or more, 20% or more, and 25% or more means about 5% or more, about 10% or more, about 15% or more, about 20% or more, and about 25% or more.

KRas G12C INHIBITOR COMPOUNDS

In one aspect of the invention, provided herein are methods of treating cancer in a subject in need thereof, comprising administering to the subject a therapeutically effective amount of a combination of a SOS1 inhibitor, or a pharmaceutically acceptable salt or a pharmaceutical composition thereof, and the KRas G12C inhibitor compound adagrasib or a pharmaceutically acceptable salt or a pharmaceutical composition thereof.

In one embodiment, the KRas G12C inhibitor is:

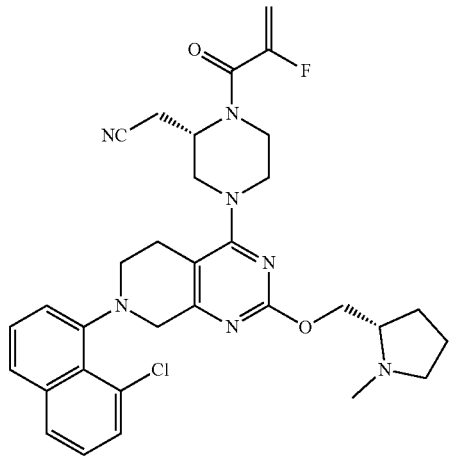 [SMILES: C=C(F)C(=O)N1CCN(c2nc(OC[C@@H]3CCCN3C)nc3c2CCN(c2cccc4cccc(Cl)c24)C3)C[C@@H]1CC#N]

(also referred to as adagrasib, MRTX849, and Example 478 in WO2019099524) or a pharmaceutically acceptable salt thereof.

The KRas G12C inhibitors used in the methods of the present invention may have one or more chiral center and may be synthesized as stereoisomeric mixtures, isomers of identical constitution that differ in the arrangement of their atoms in space. The compounds may be used as mixtures or the individual components/isomers may be separated using commercially available reagents and conventional methods for isolation of stereoisomers and enantiomers well-known to those skilled in the art, e.g., using CHIRALPAK® (Sigma-Aldrich) or CHIRALCEL® (Diacel Corp) chiral chromatographic HPLC columns according to the manufacturer's instructions. Alternatively, compounds of the present invention may be synthesized using optically pure, chiral reagents and intermediates to prepare individual isomers or enantiomers. Unless otherwise indicated, all chiral (enantiomeric and diastereomeric) and racemic forms are within the scope of the invention. Unless otherwise indicated, whenever the specification, including the claims, refers to compounds of the invention, the term "compound" is to be understood to encompass all chiral (enantiomeric and diastereomeric) and racemic forms.

In one embodiment, the KRas G12C inhibitor compound adagrasib used in the methods include salts of the above compounds, for instance salts formed with inorganic acids such as hydrochloric acid, hydrobromic acid, sulfuric acid, phosphoric acid, nitric acid, salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid, and salts formed from quaternary ammoniums of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

Methods for manufacturing the KRas G12C inhibitors disclosed herein are known. For example, commonly owned published international PCT application numbers WO2017201161, and WO 2019099524 describe general reaction schemes for preparing compounds including adagrasib and also provide detailed synthetic routes for the preparation of these compounds.

SOS1 Inhibitor Compounds

In one embodiment, the SOS1 inhibitor is a compound selected from (R)-2-methyl-3-(1-((4-methyl-7-morpholinopyrido[3,4-d]pyridazin-1-yl)amino)ethyl)benzonitrile, 3-((R)-1-((7-((S)-hexahydropyrazino[2,1-c][1,4]oxazin-8(1H)-yl)-4-methylpyrido[3,4-d]pyridazin-1-yl)amino)ethyl)-2-methylbenzonitrile, (R)-3-(1-((7-(3-(dimethylamino)-3-methylazetidin-1-yl)-4-methylpyrido[3,4-d]pyridazin-1-yl)amino)ethyl)-2-methylbenzonitrile, (R)-2-methyl-3-(1-((4-methyl-7-(4-methylpiperazin-1-yl)pyrido[3,4-d]pyridazin-1-yl)amino)ethyl)benzonitrile, (R)-3-(1-((7-(4-ethylpiperazin-1-yl)-4-methylpyrido[3,4-d]pyridazin-1-yl)amino)ethyl)-2-methylbenzonitrile, (R)-2-methyl-3-(1-((4-methyl-7-(piperazin-1-yl)pyrido[3,4-d]pyridazin-1-yl)amino)ethyl)benzonitrile, 3-((R)-1-((7-((S)-3-(dimethylamino)pyrrolidin-1-yl)-4-methylpyrido[3,4-d]pyridazin-1-yl)amino)ethyl)-2-methylbenzonitrile, (R)-3-(1-((6-fluoro-4-methyl-7-(4-methylpiperazin-1-yl)phthalazin-1-yl)amino)ethyl)-2-methylbenzonitrile, or a pharmaceutically acceptable salt thereof; or selected from the compounds described in U.S. provisional patent applications 62/951,812, 62/975,645, 63/044,802, 62/980,790 and 63/057,563 (and corresponding international applications and publications including PCT/US20/06603 and U.S. Ser. No. 17/127,582) as described in greater detail herein.

In another embodiment, the SOS1 inhibitor is BI1701963.

In another embodiment the SOS1 inhibitor is a compound of the formula:

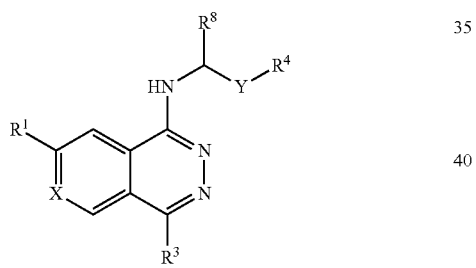

or a pharmaceutically acceptable salt thereof, wherein: $R^1$ is hydrogen, hydroxyl, C1-C6 alkyl, alkoxy, —N($R^6$)$_2$, —N$R^6$C(O)$R^6$, —C(O)N($R^6$)$_2$, —SO$_2$alkyl, —SO$_2$N$R^6$alkyl, cycloalkyl, -Q-heterocyclyl, aryl, or heteroaryl, wherein the cycloalkyl, the heterocyclyl, the aryl, and the heteroaryl are each optionally substituted with one or more $R^2$; each Q is independently a bond, O, or N$R^6$; X is N or C$R^7$; each $R^2$ is independently hydroxy, halogen, cyano, hydroxyalkyl, haloalkyl, alkoxy, —N($R^6$)$_2$, —SO$_2$alkyl, —NRC(O)C1-C3 alkyl, —C(O)cycloalkyl, —C(O)heretocyclyl or aryl, wherein the cycloalkyl, the heterocyclyl or the aryl are each optionally substituted with one or more $R^{11}$; $R^3$ is hydrogen, C1-C6 alkyl, alkoxy, —N($R^{10}$)$_2$, cycloalkyl, haloalkyl, heterocyclyl, aryl, or heteroaryl, wherein the C1-C6 alkyl, the cycloalkyl, the heterocyclyl, the aryl, and the heteroaryl are each optionally substituted with one or more $R^9$; Y is a bond or heteroarylene; $R^4$ is aryl or heteroaryl, each optionally substituted with one or more $R^5$; each $R^5$ is independently hydroxy, halogen, cyano, hydroxyalkyl, alkoxy, C1-C3 alkyl, haloalkyl, —N($R^6$)$_2$, -L-N($R^6$)$_2$ or —SO$_2$alkyl; L is C1-C3 alkylene; each $R^6$ is independently hydrogen, C1-C3 alkyl, haloalkyl, or cycloalkyl; $R^7$ is hydrogen, cyano, or alkoxy; $R^8$ is C1-C2 alkyl or halo-C1-C2 alkyl; each $R^9$ is independently hydroxy, halogen, amino, cyano, alkoxy, or C1-C3 alkyl; each $R^{10}$ is independently hydrogen, C1-C3 alkyl or cycloalkyl; and each $R^{11}$ is independently C1-C3 alkyl or haloalkyl. These compounds include, but are not limited to, compounds such as:

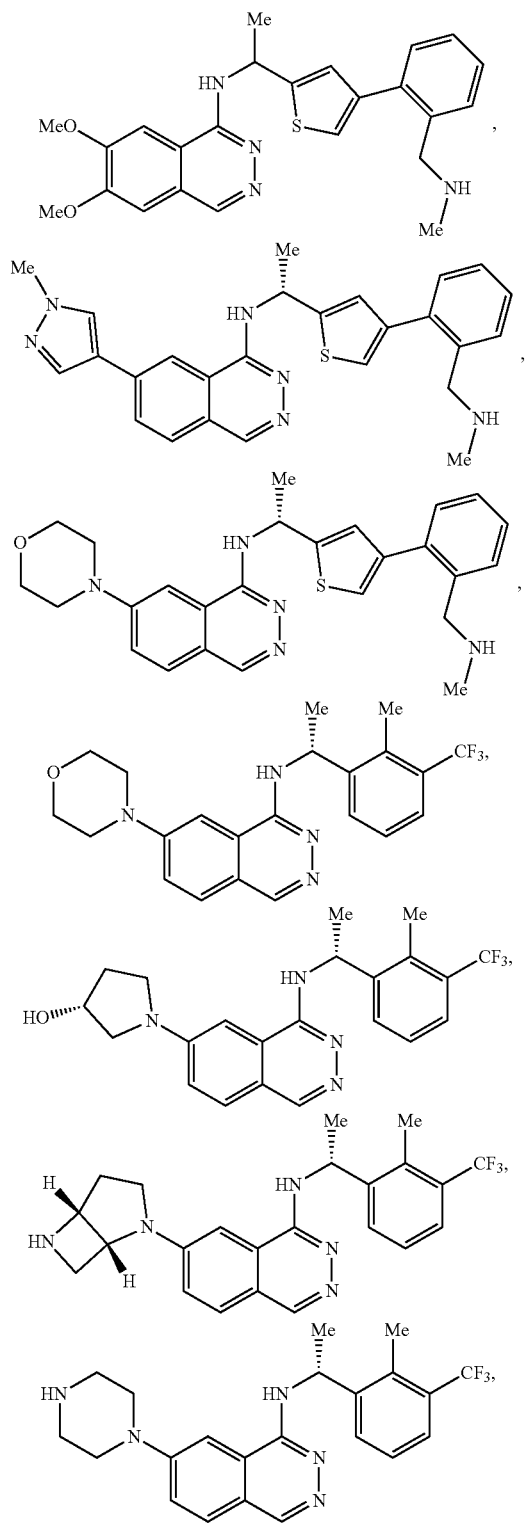

-continued
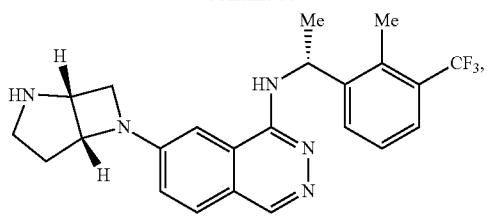
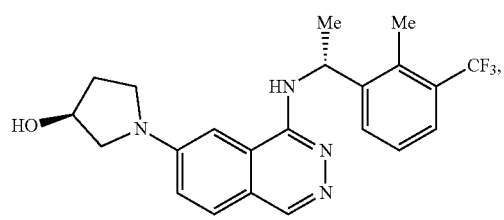
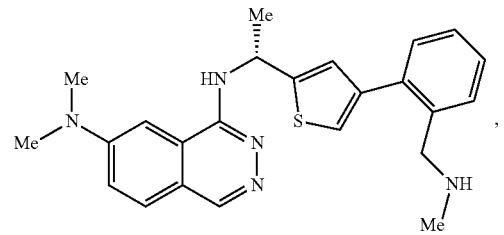
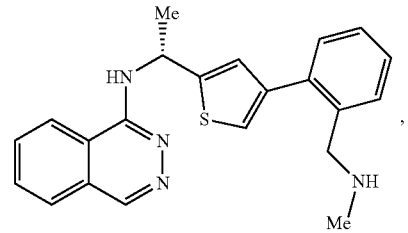
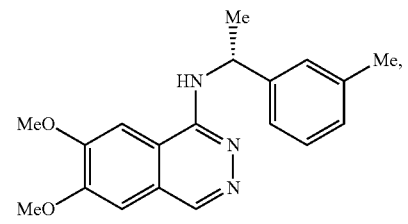
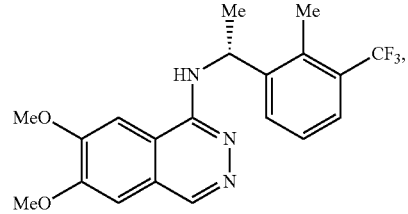
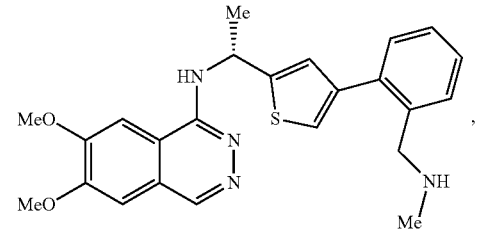
-continued
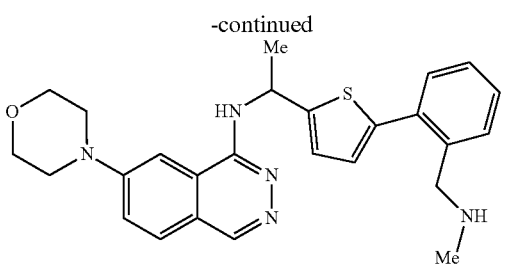
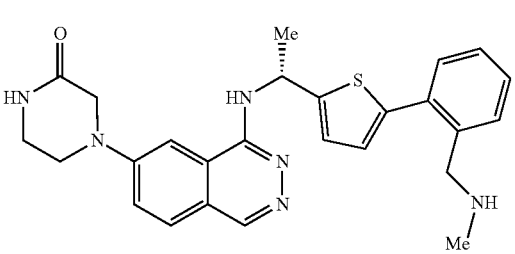
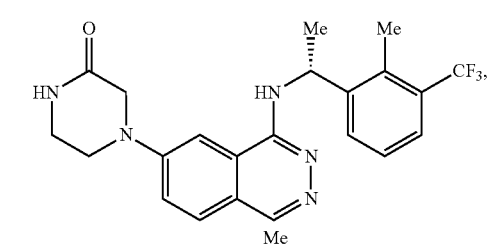
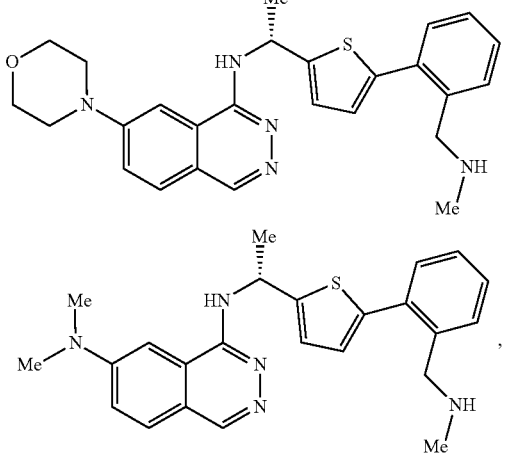
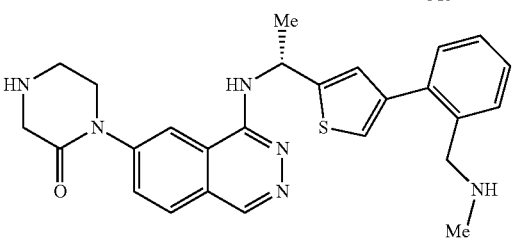
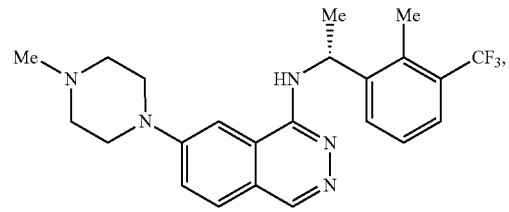

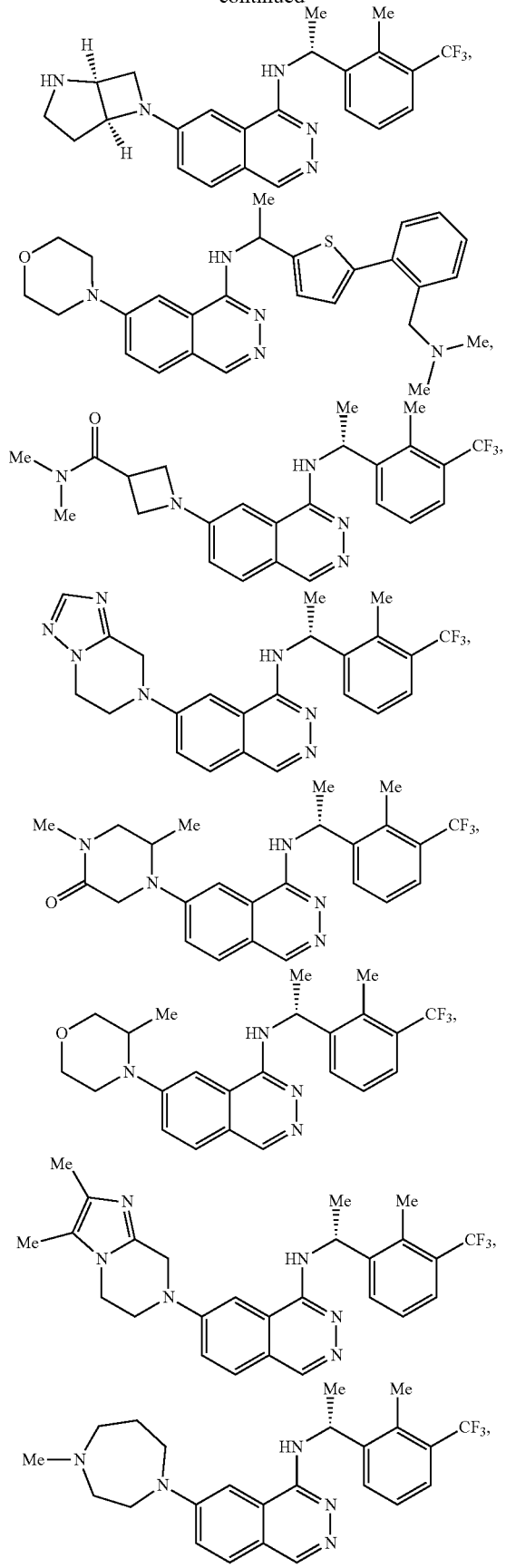
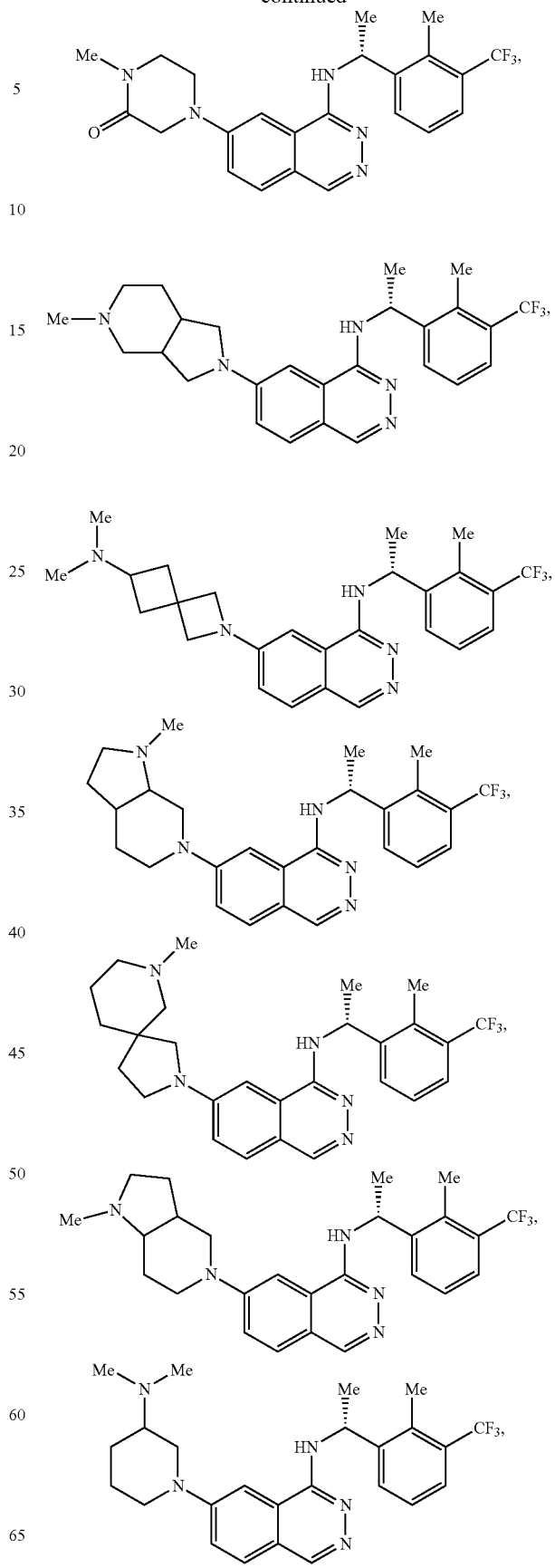

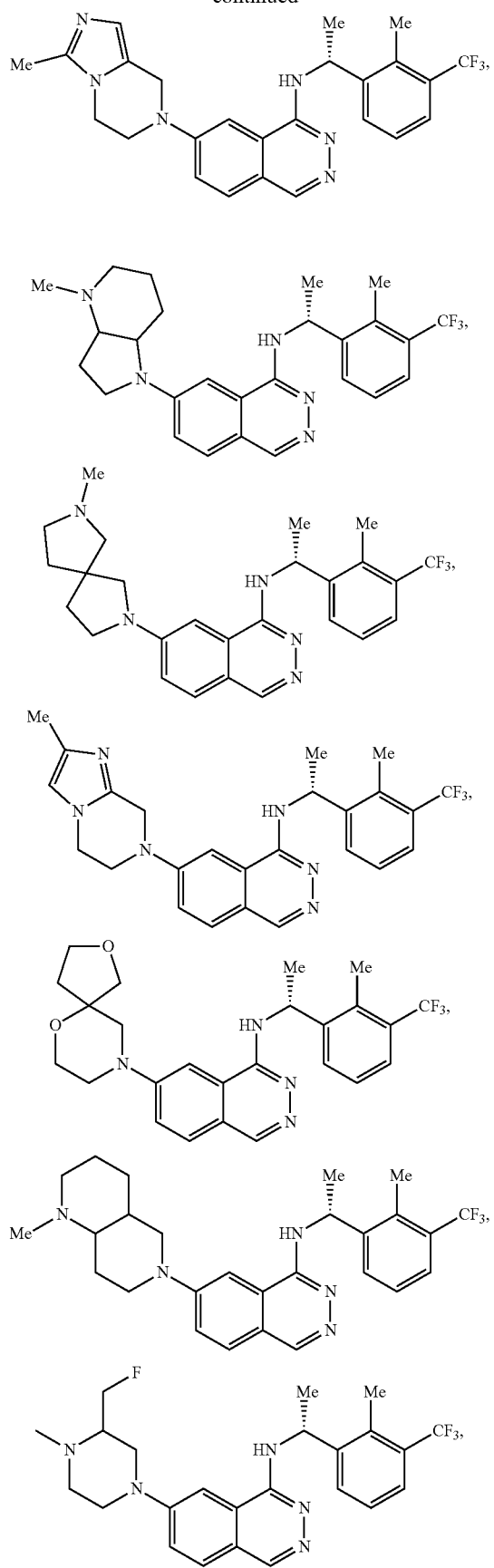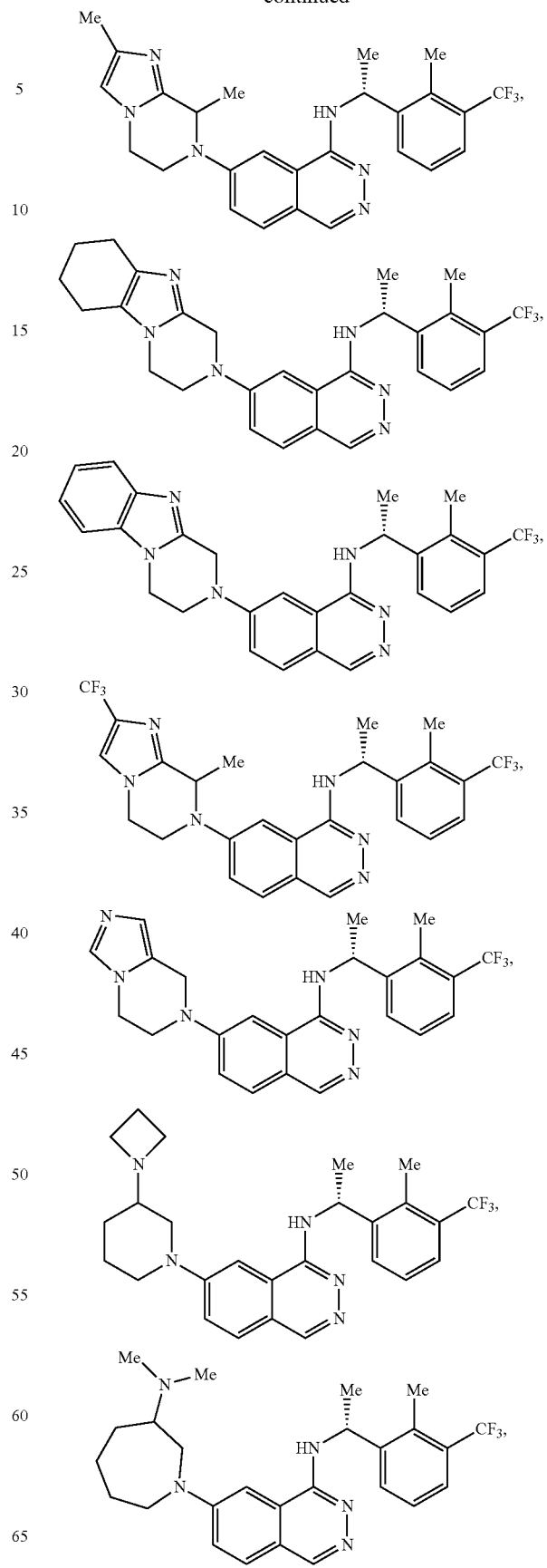

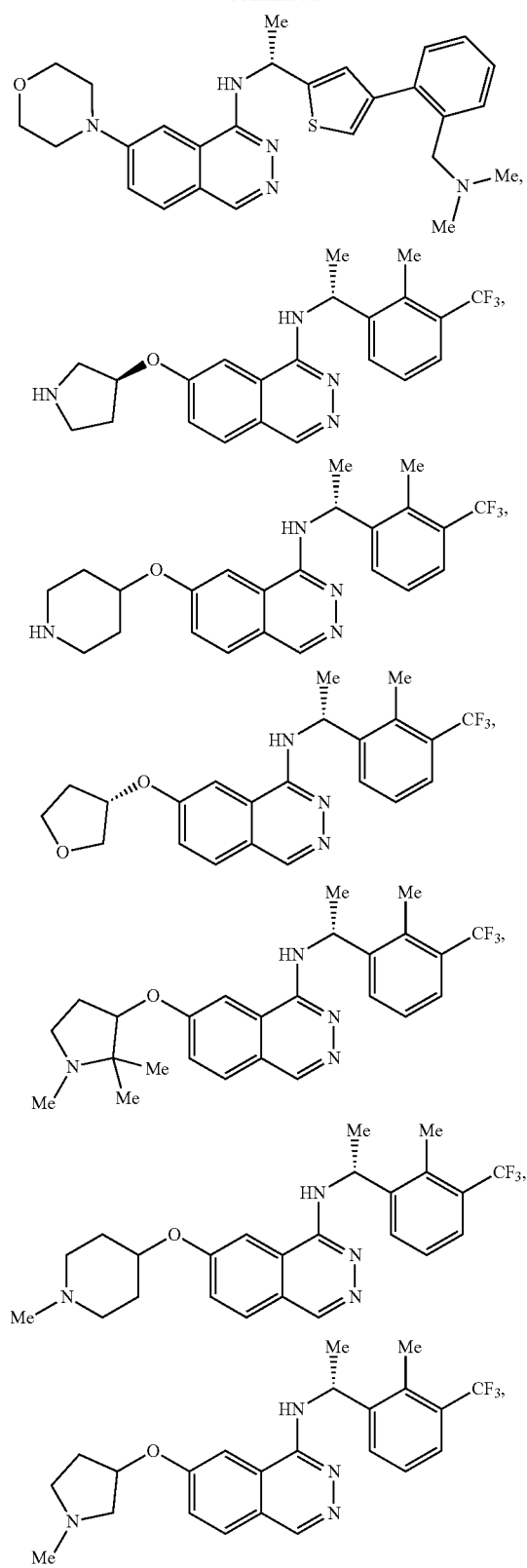
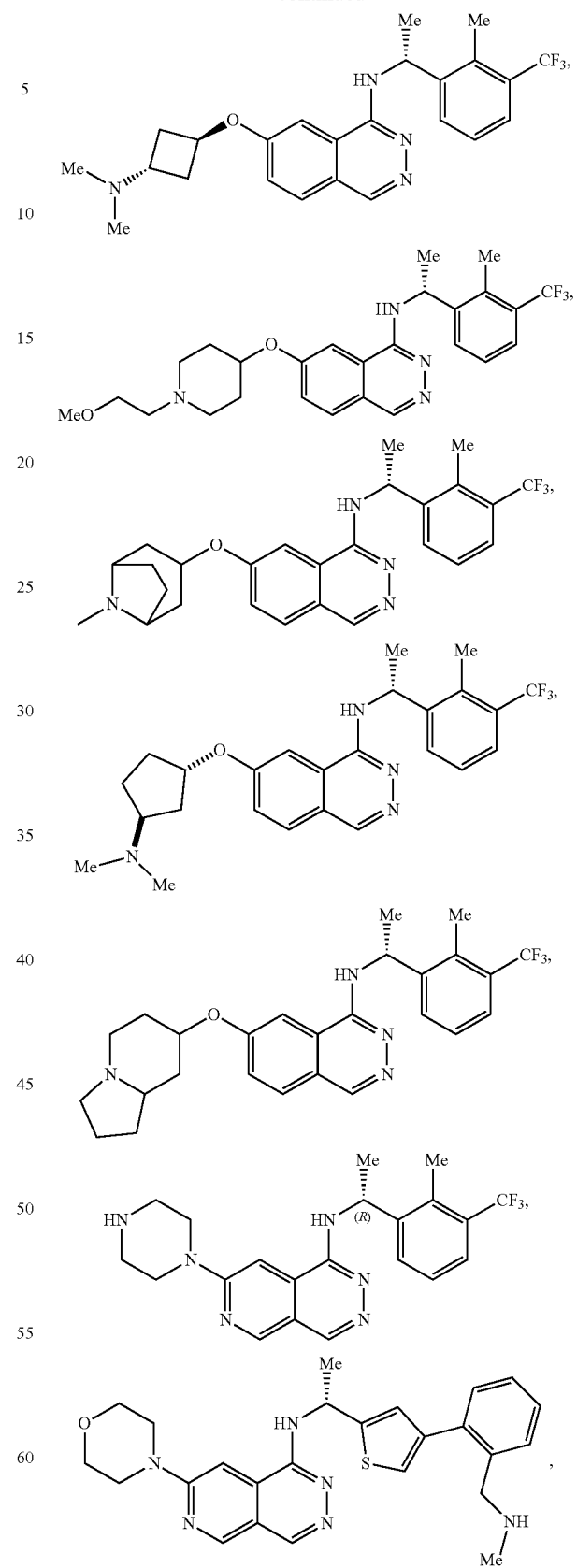

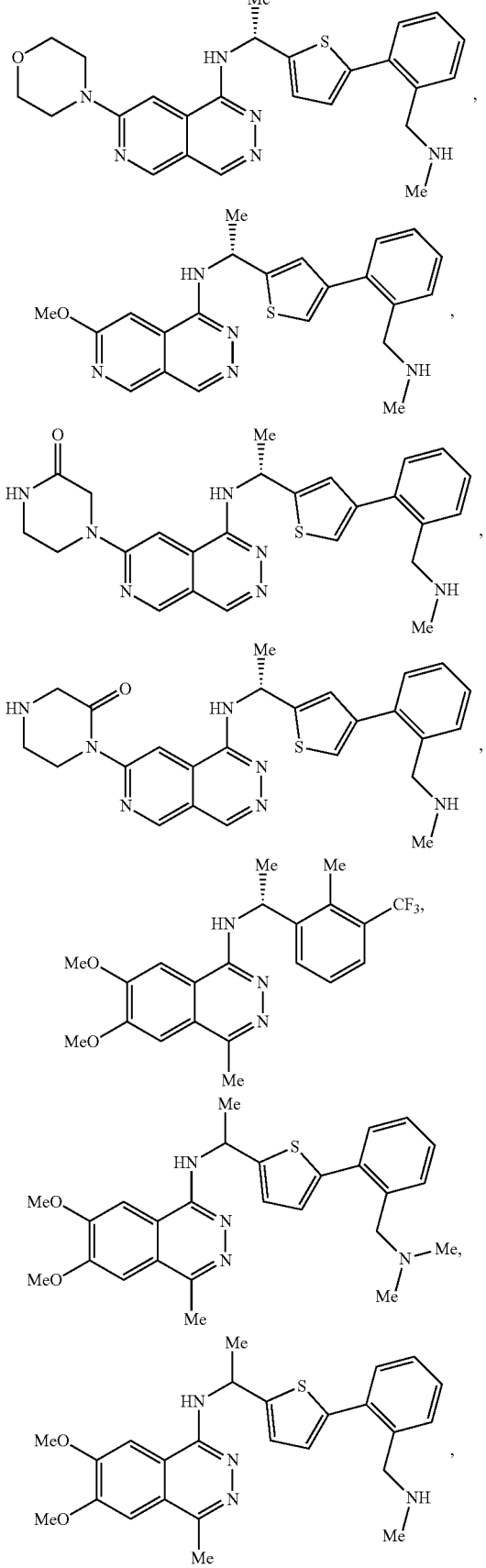
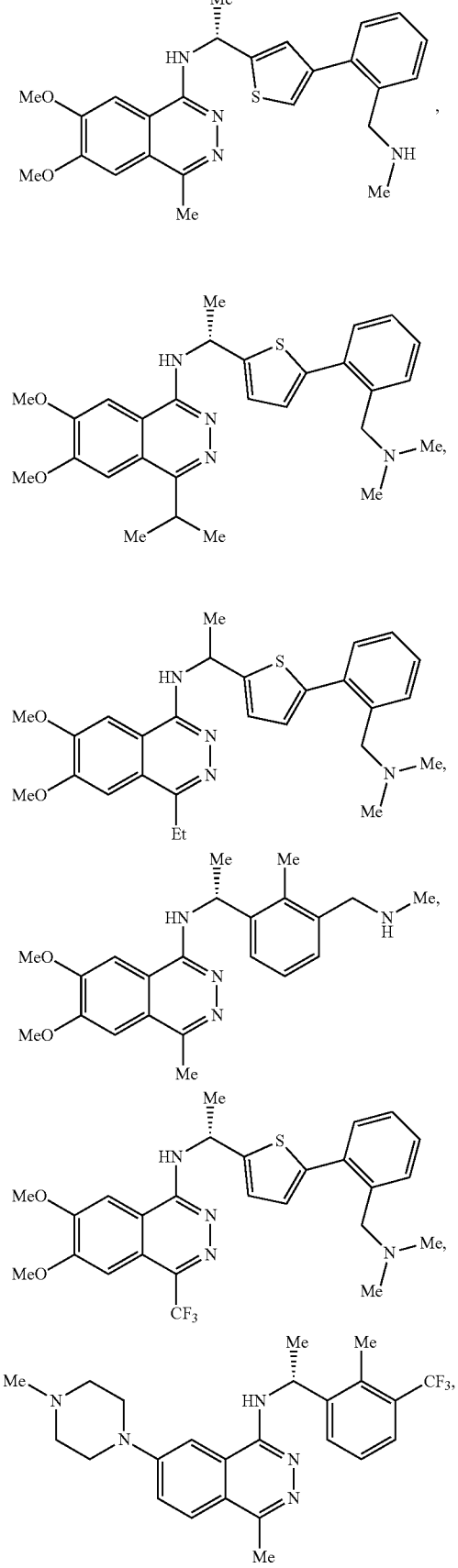

-continued

33
-continued
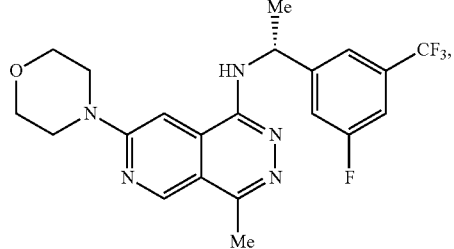
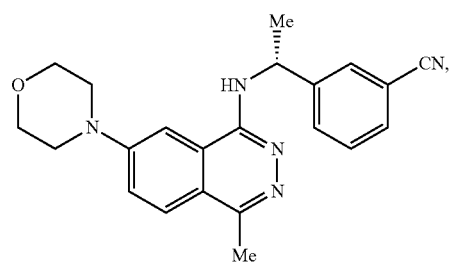
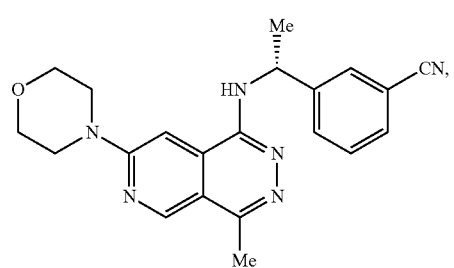
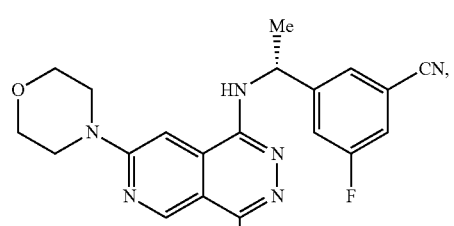
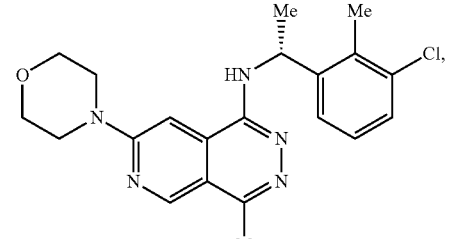
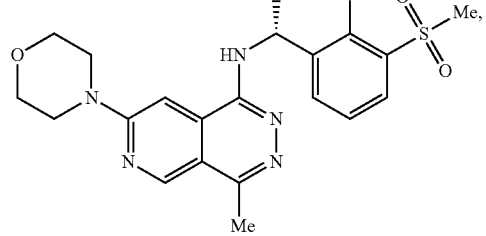
34
-continued
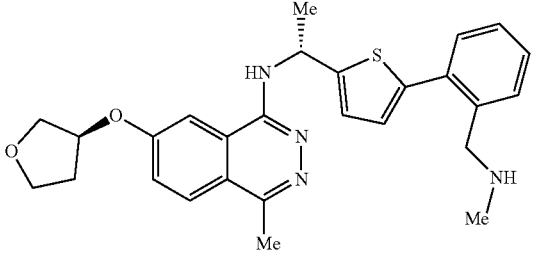
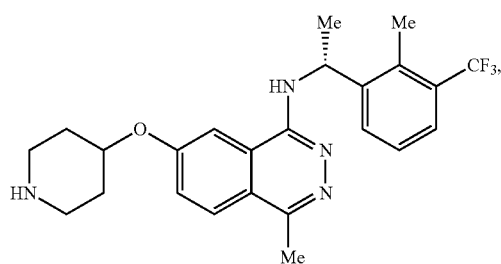
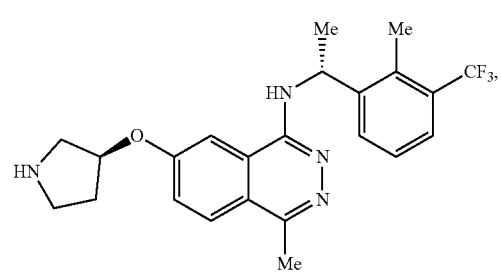
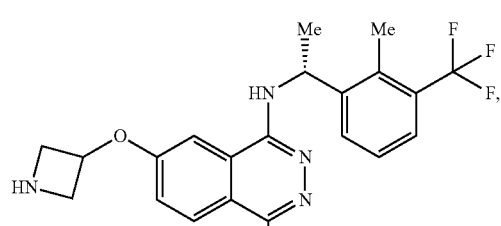
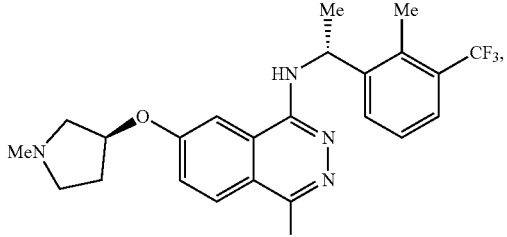
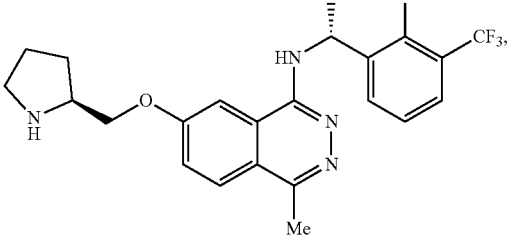

35
-continued
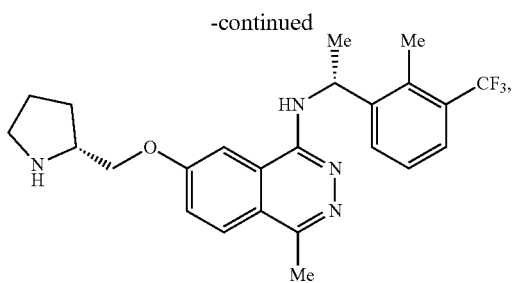
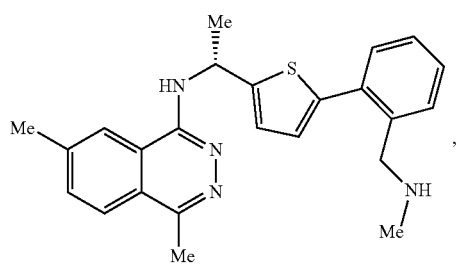
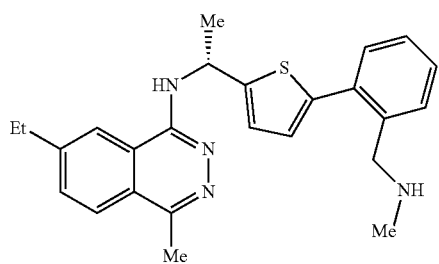
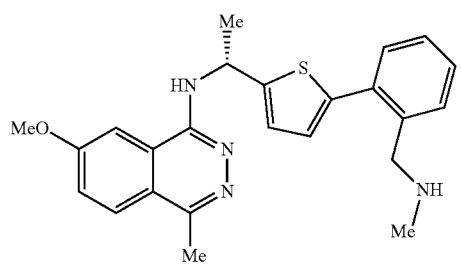
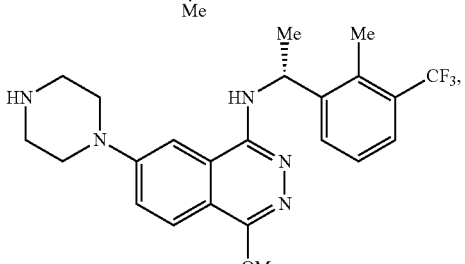
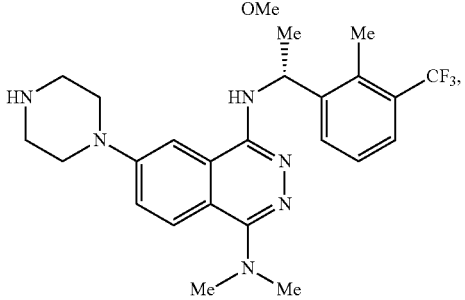
36
-continued
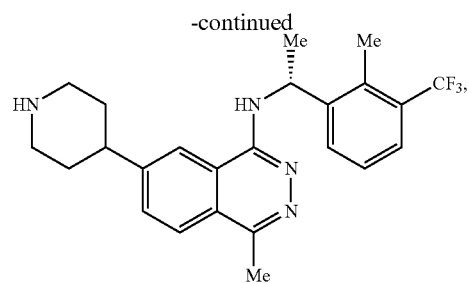
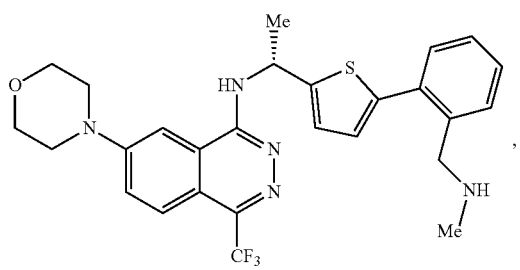
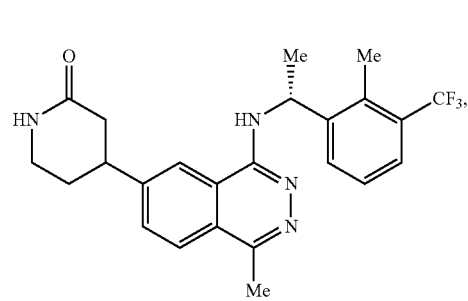
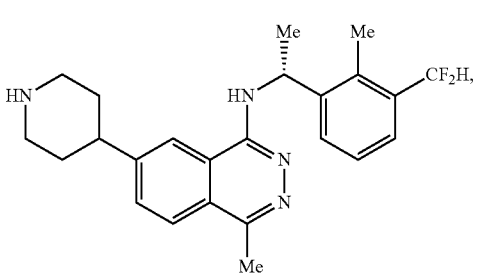
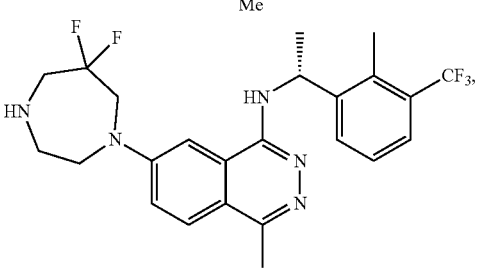
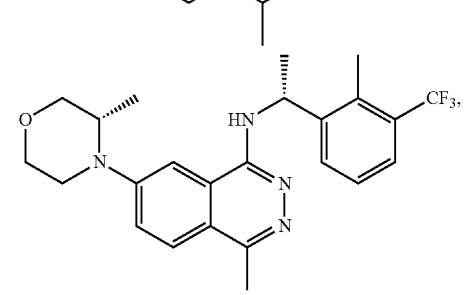

-continued
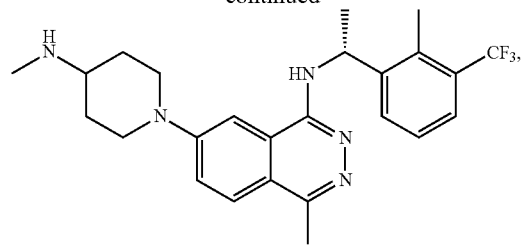
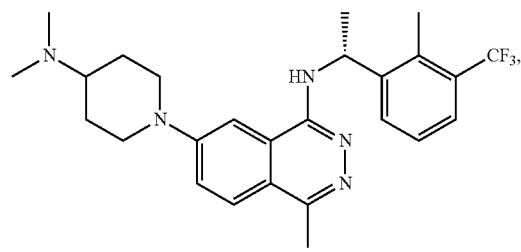
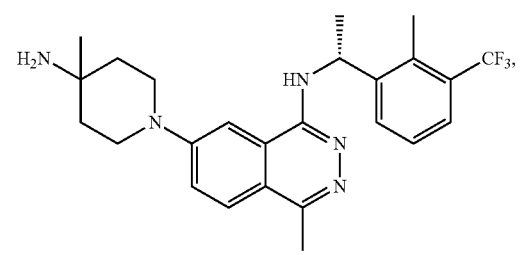
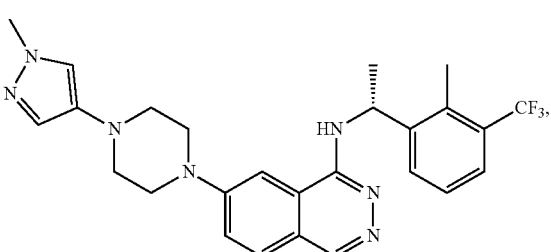
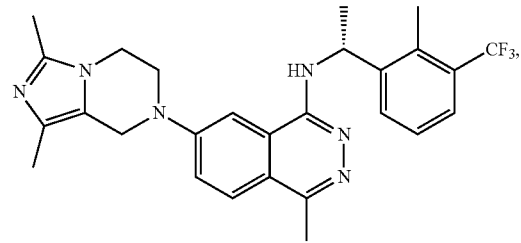
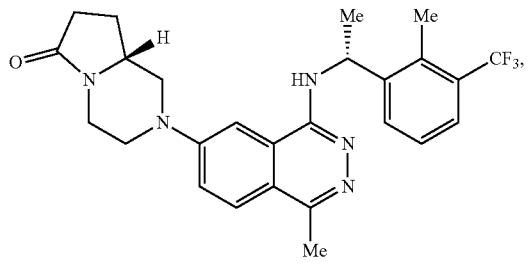
-continued
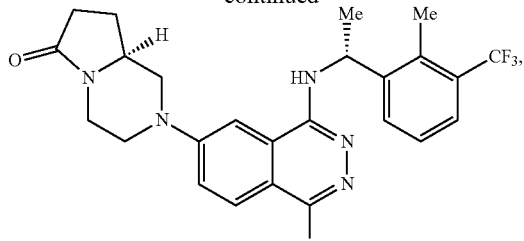
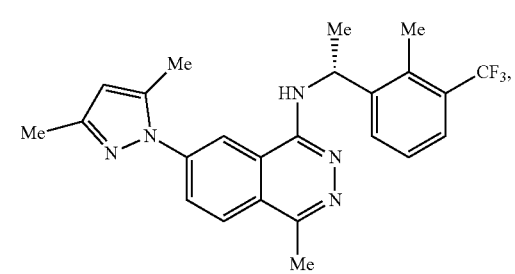
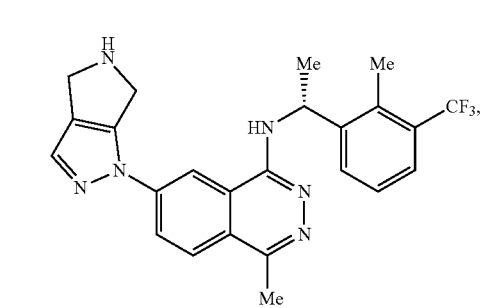
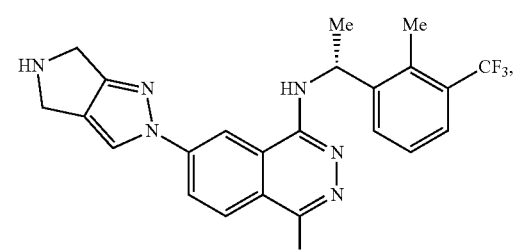
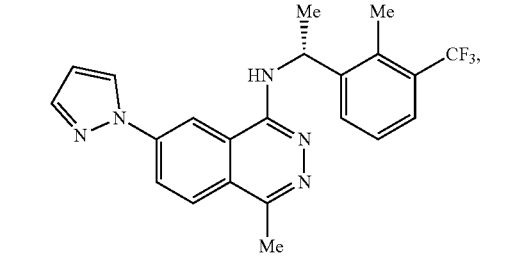
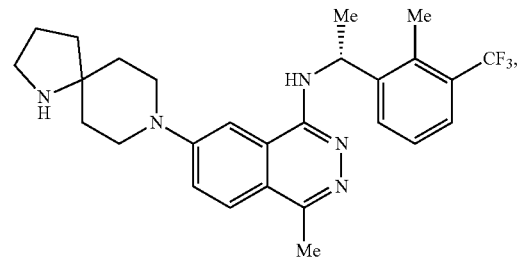

39
-continued
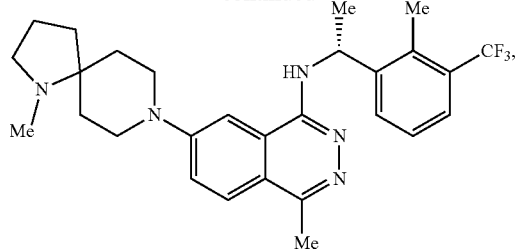
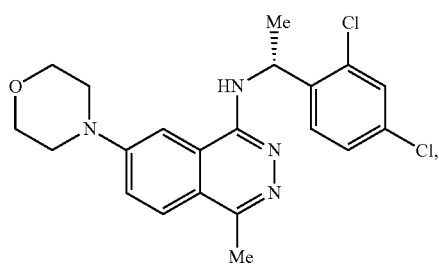
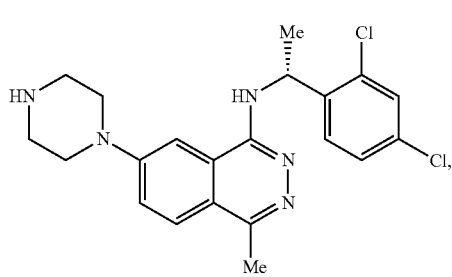
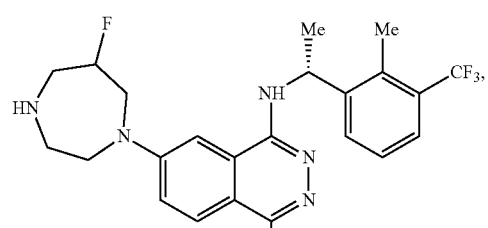
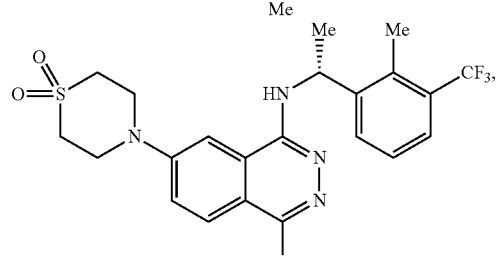
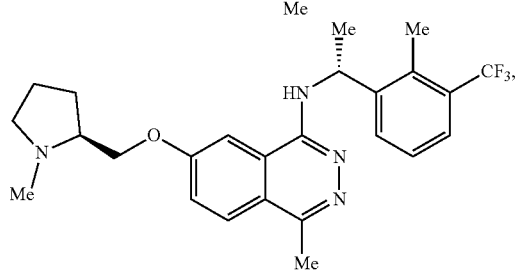
40
-continued
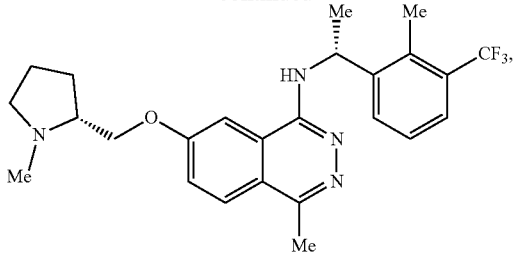
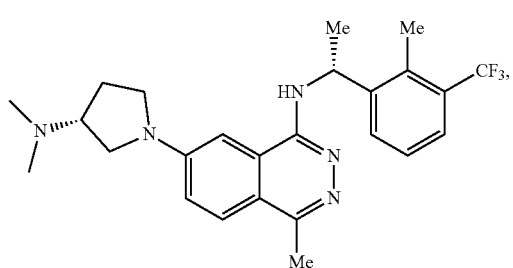
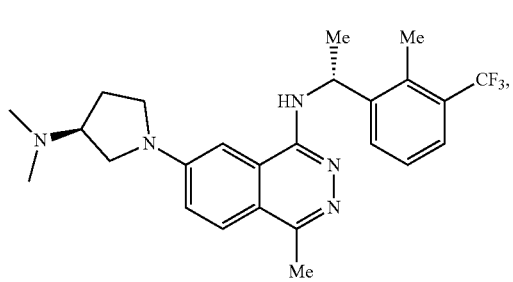
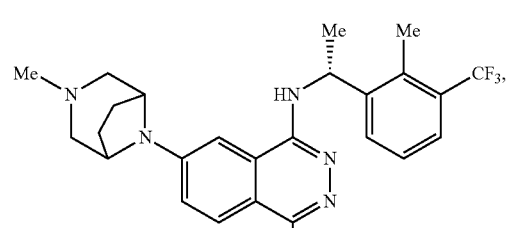
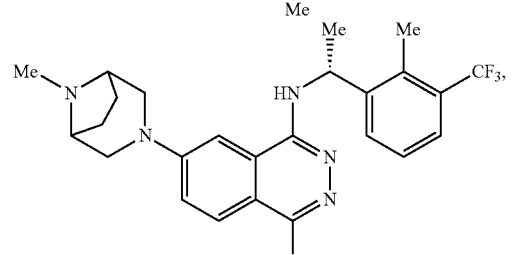
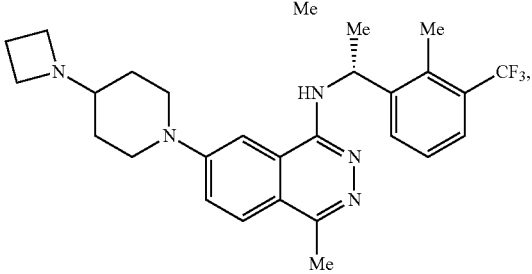

41
-continued
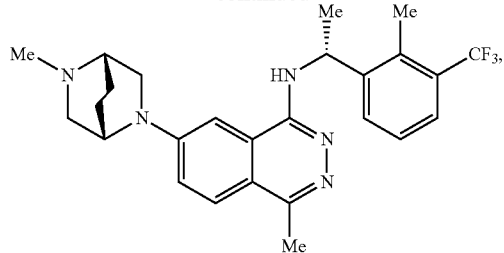
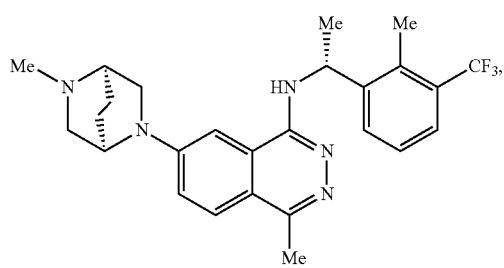
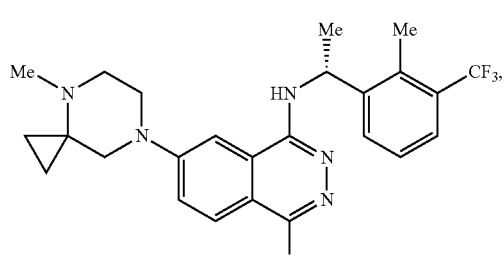
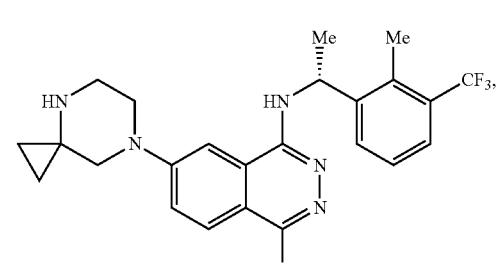
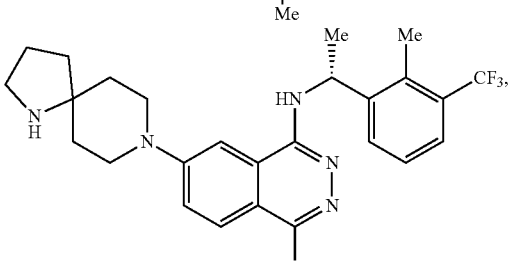
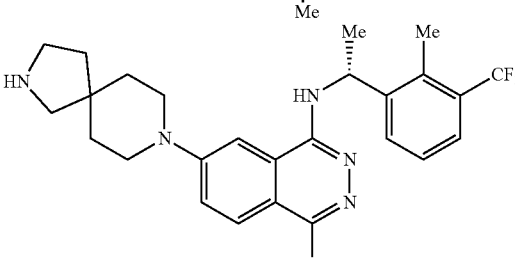
42
-continued
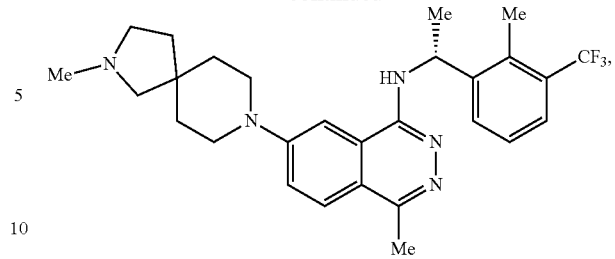
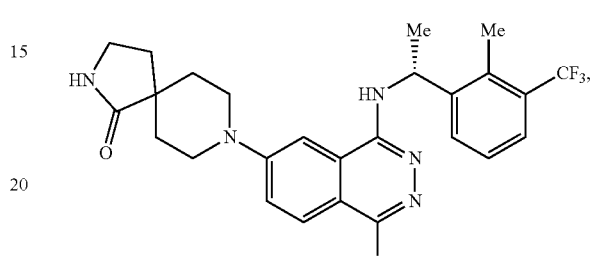
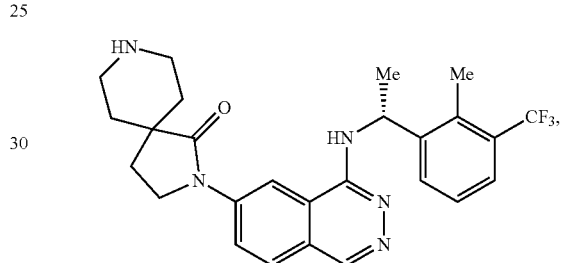
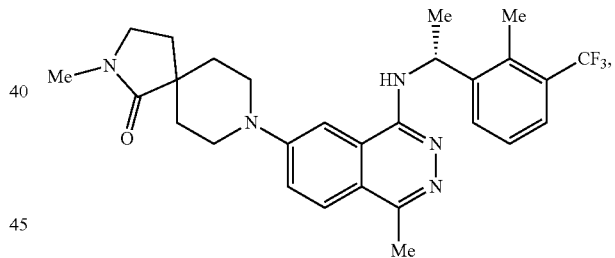
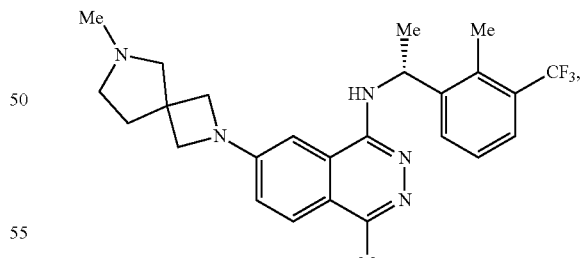
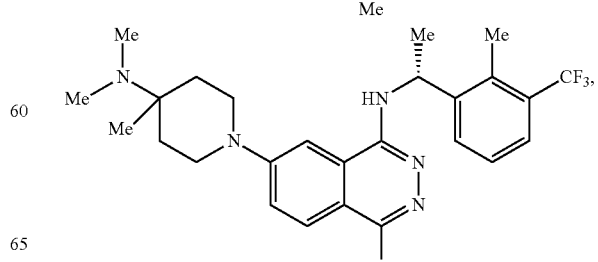

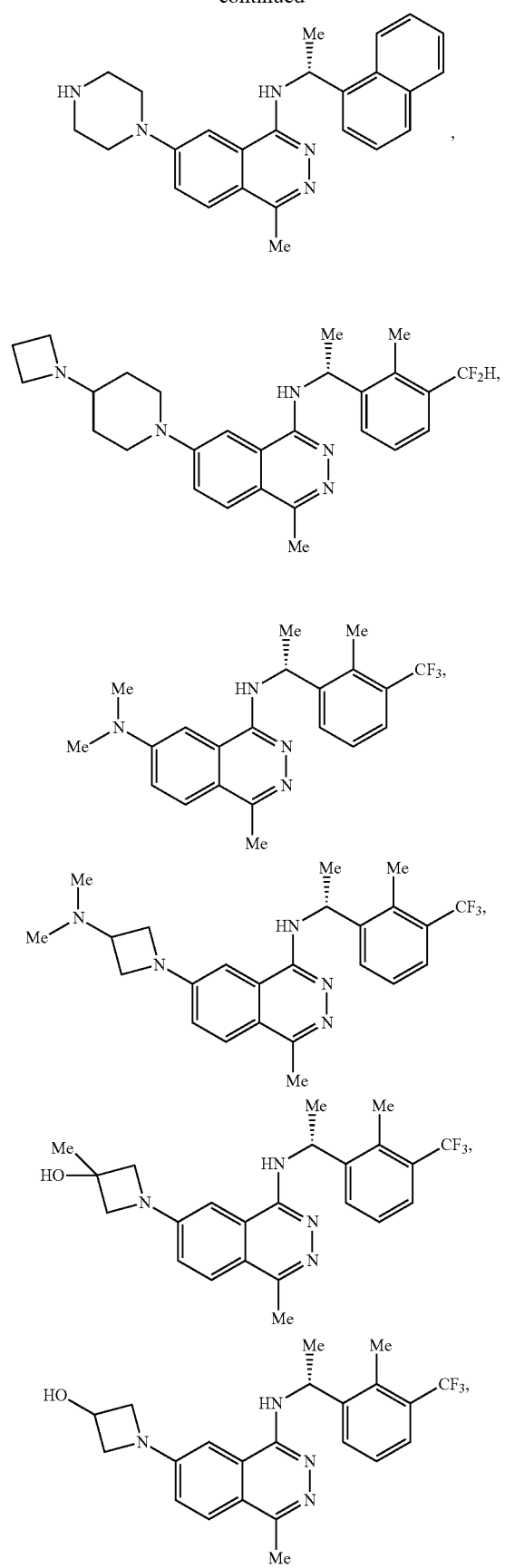

-continued
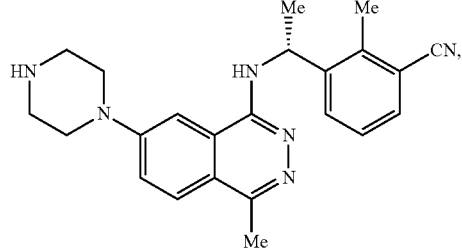
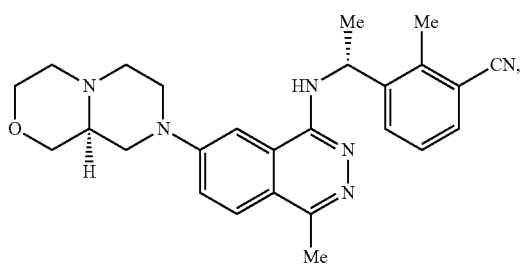
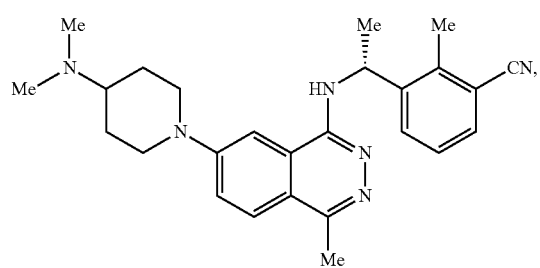
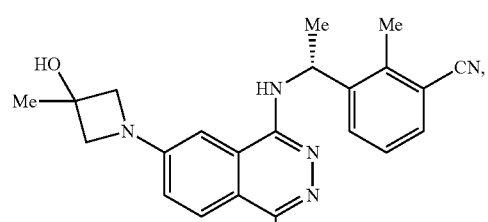
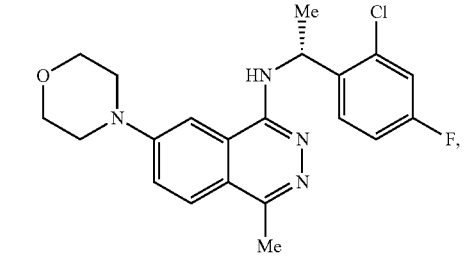
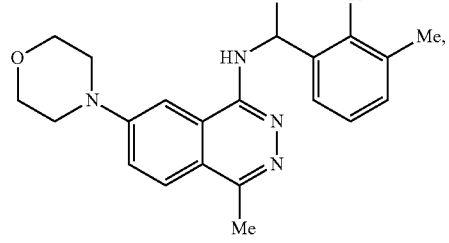
-continued
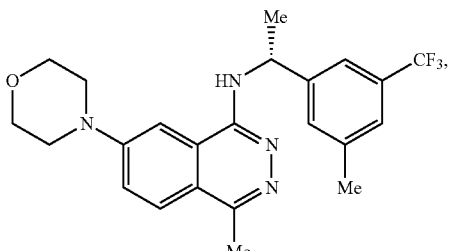
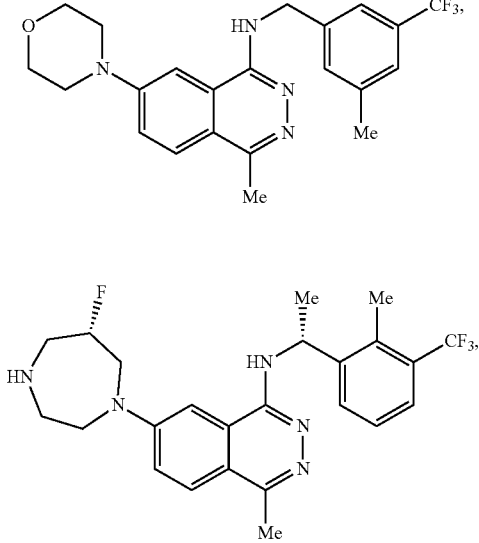
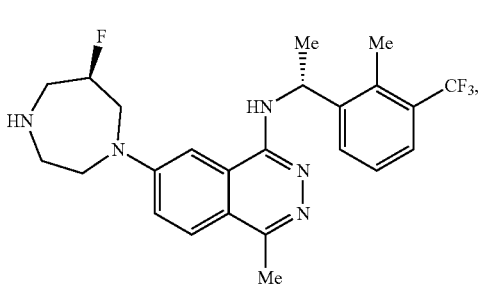
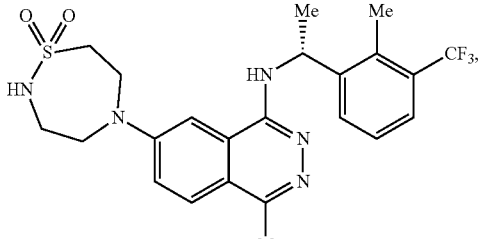
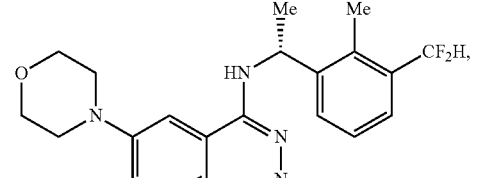
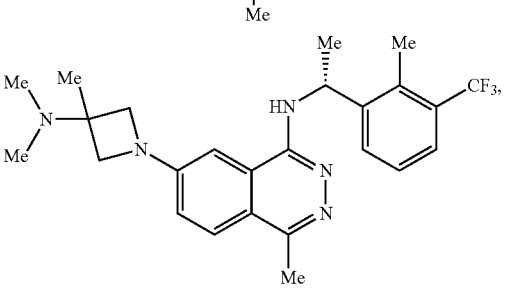

-continued

49
-continued
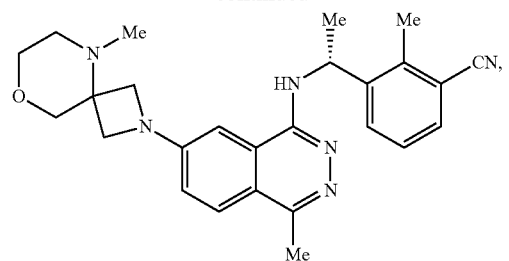
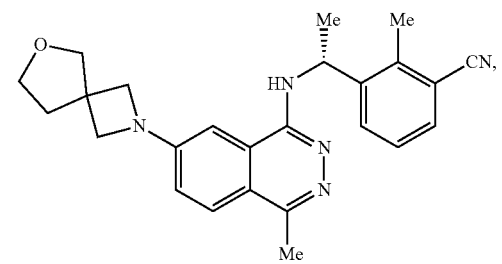
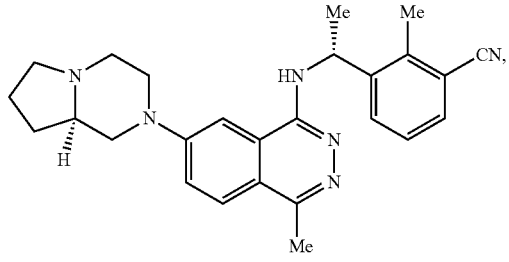
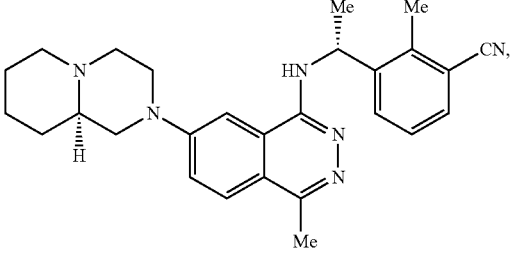
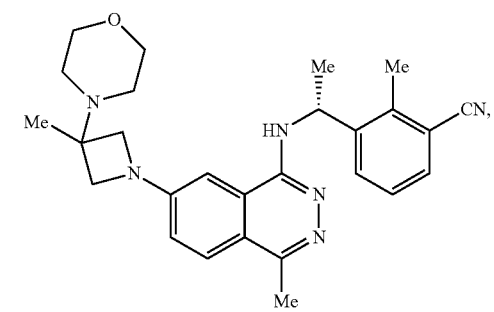
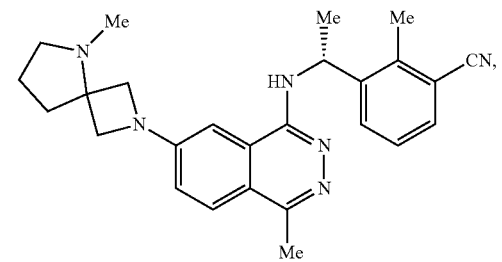
50
-continued
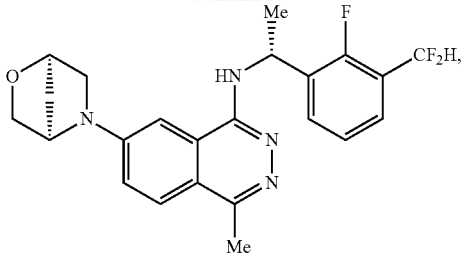
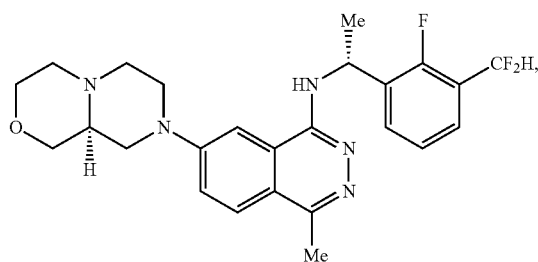
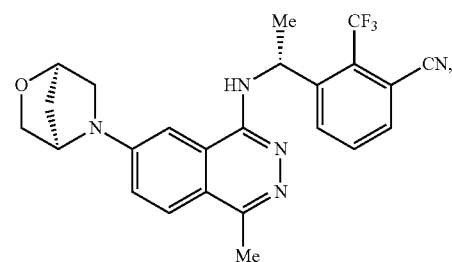
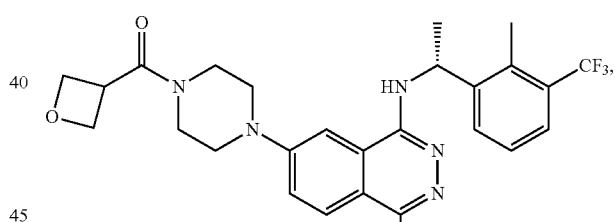
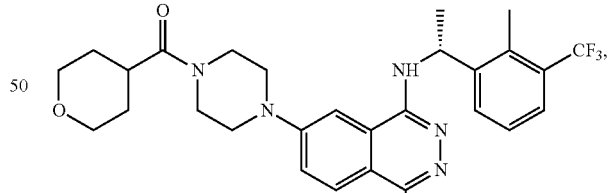
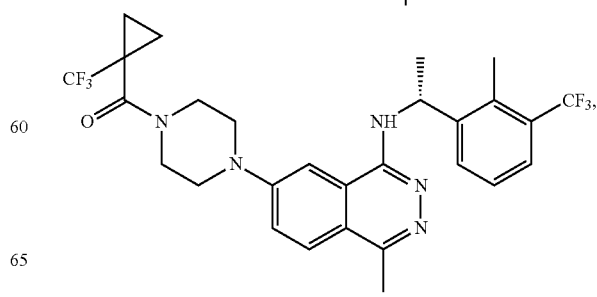

51
-continued
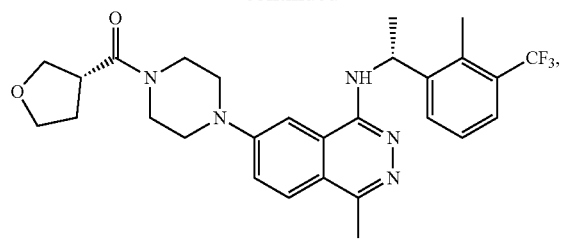
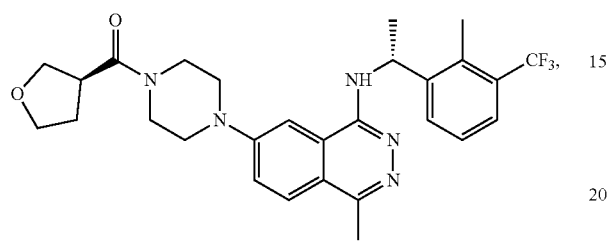
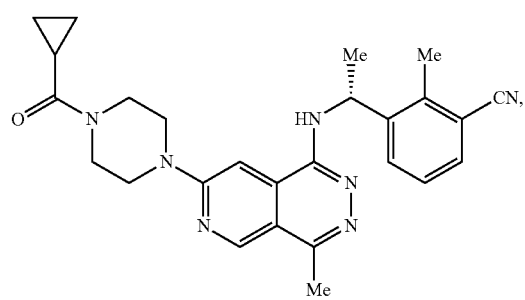
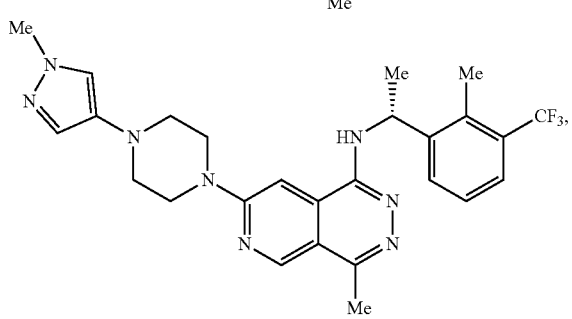
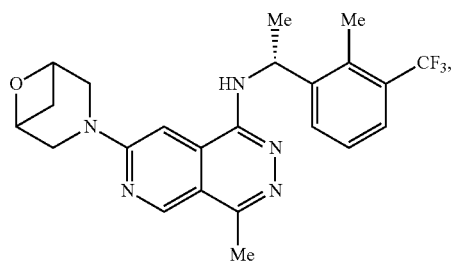
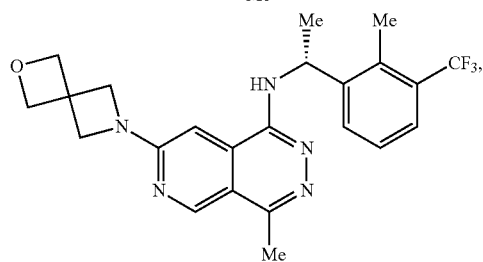
52
-continued
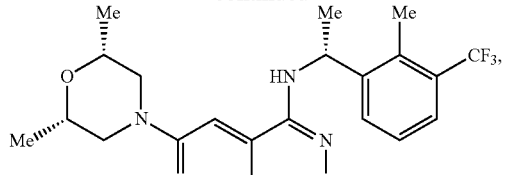
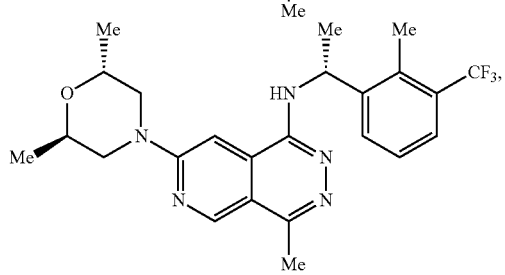
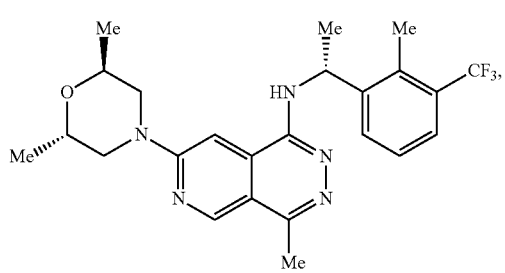
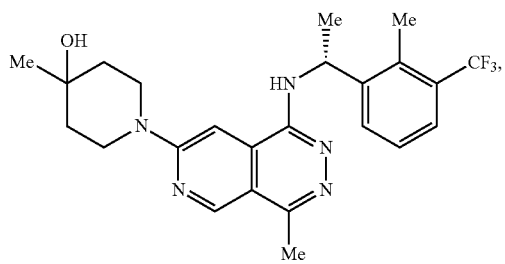
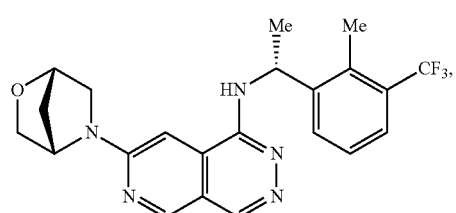
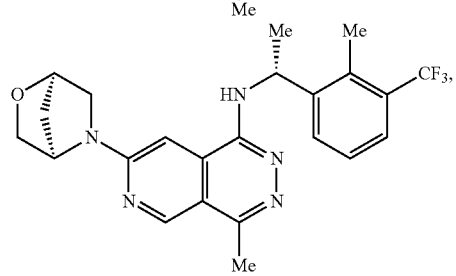

53
-continued
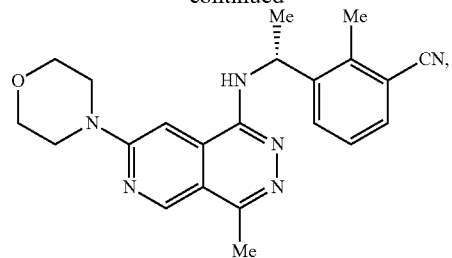
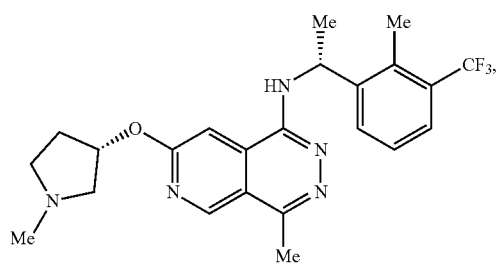
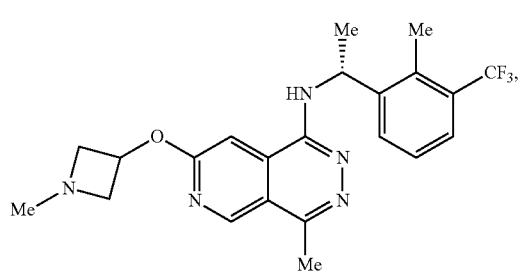
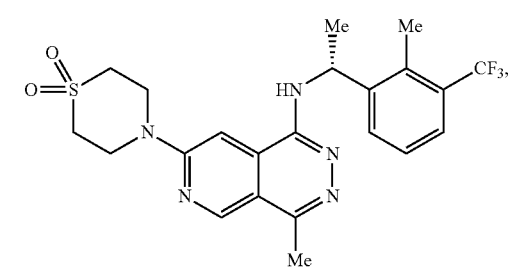
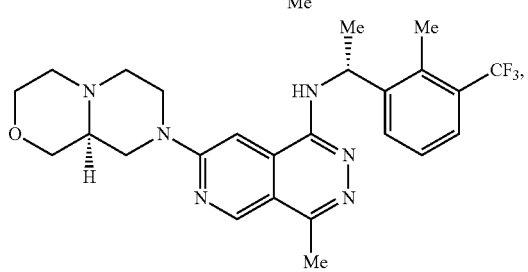
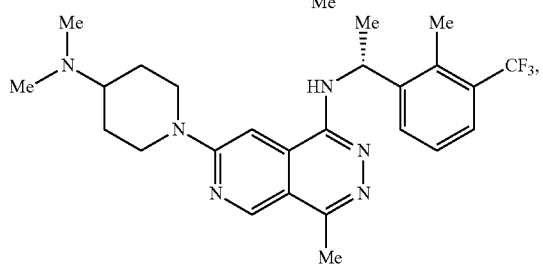
54
-continued
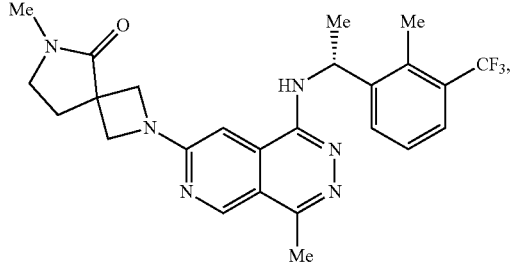
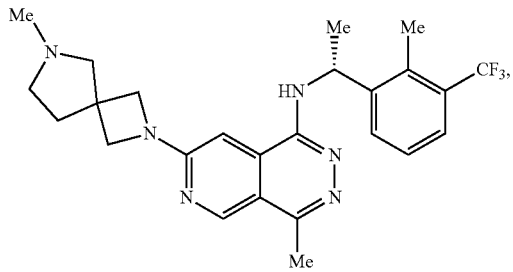
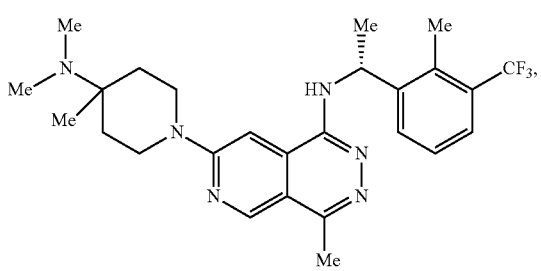
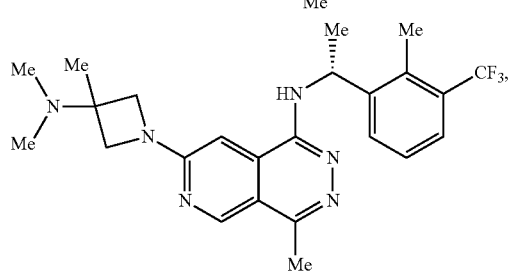
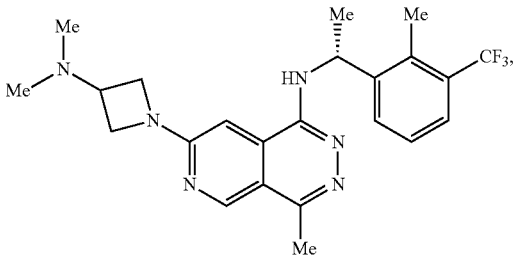
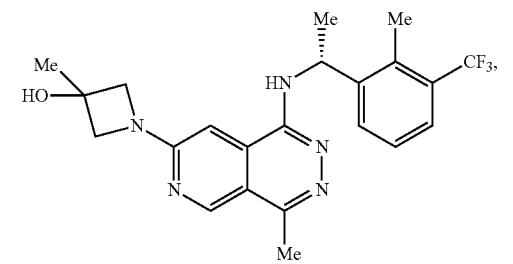

55
-continued
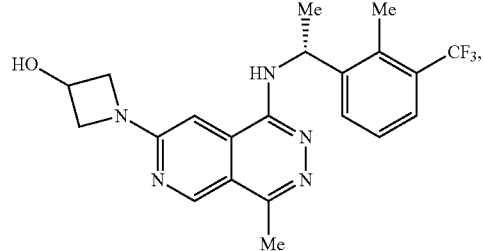
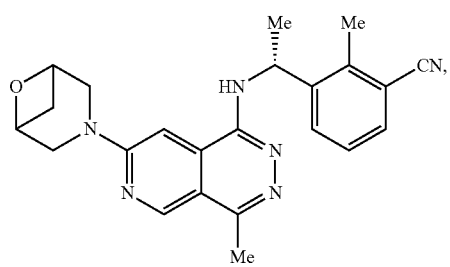
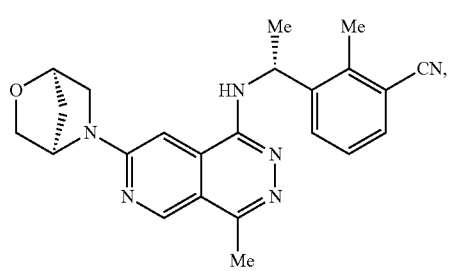
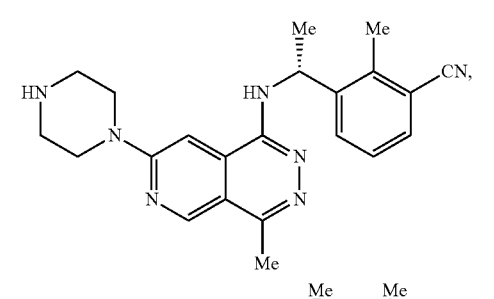
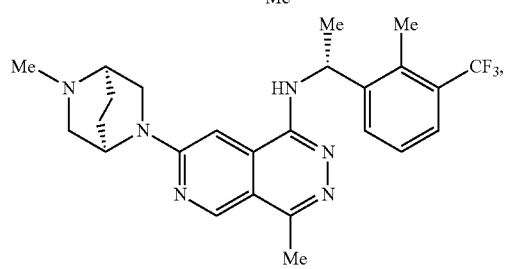
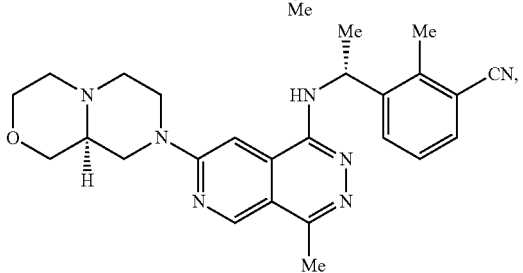
56
-continued
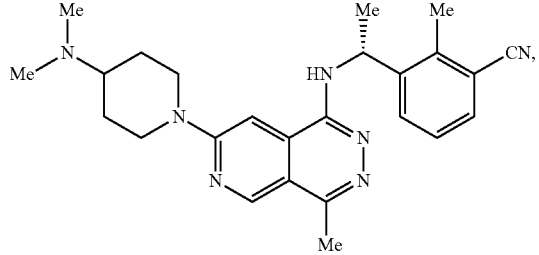
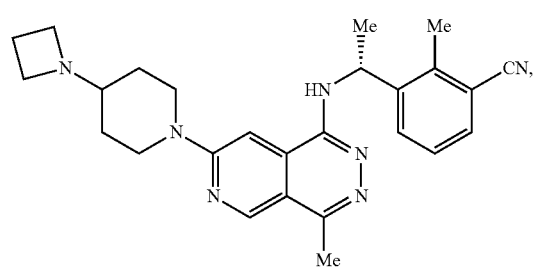
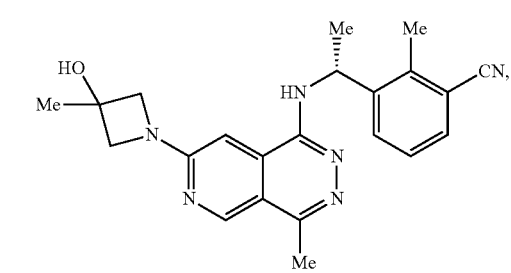
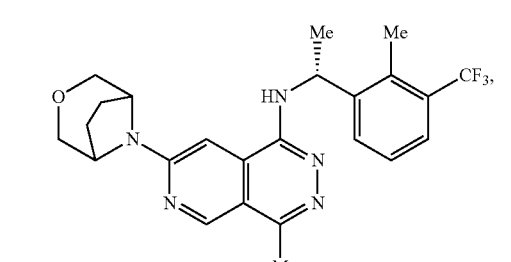
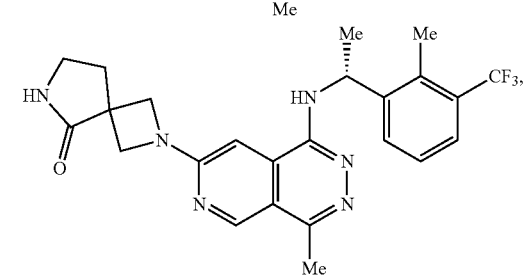
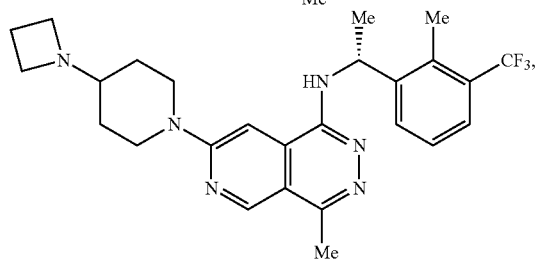

57
-continued
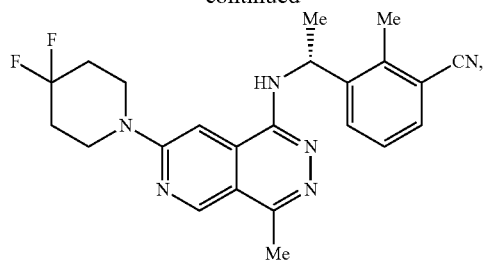
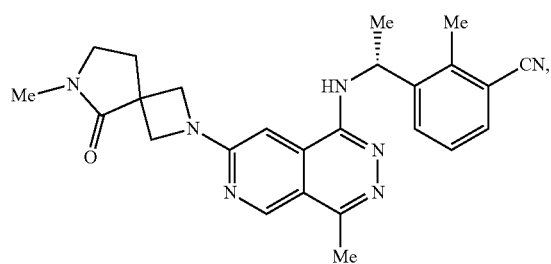
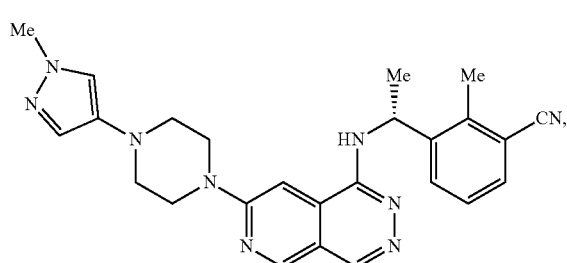
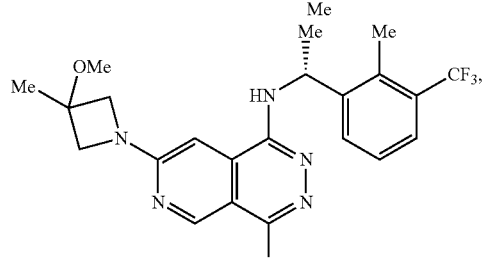
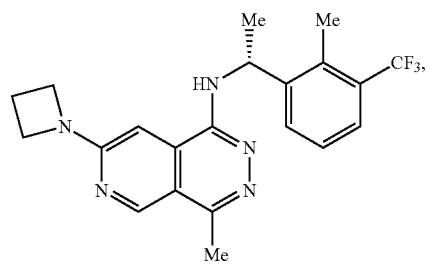
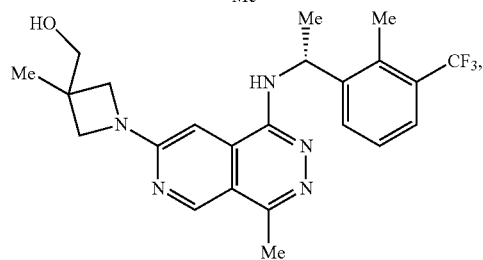
58
-continued
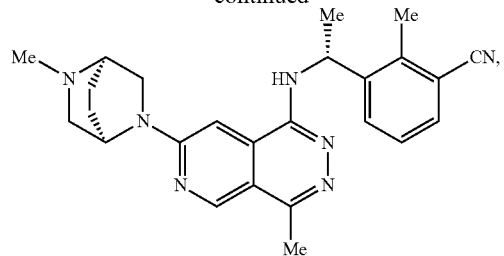
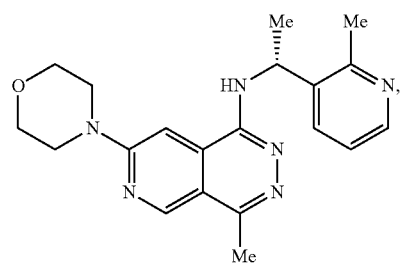
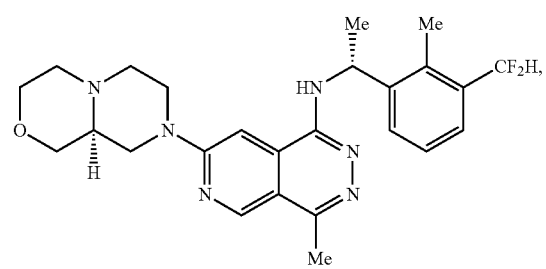
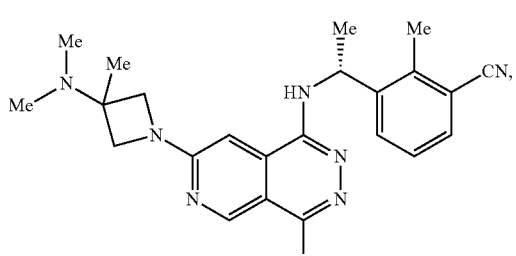
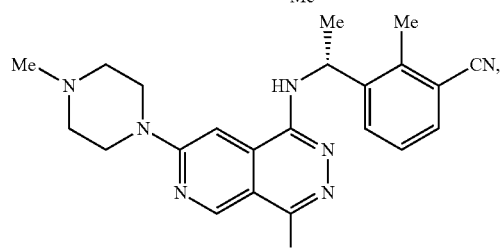
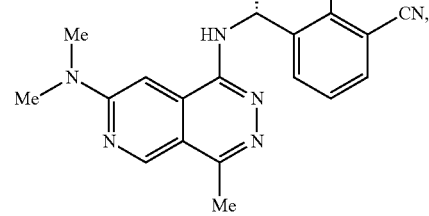

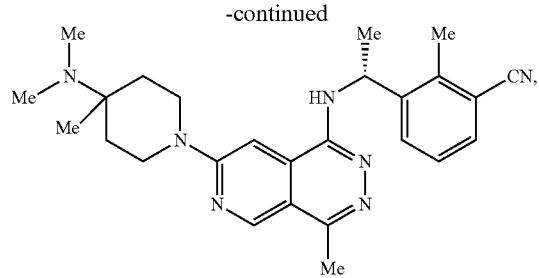
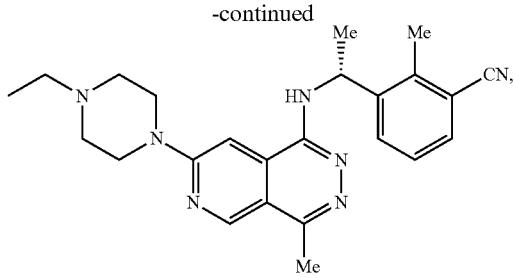
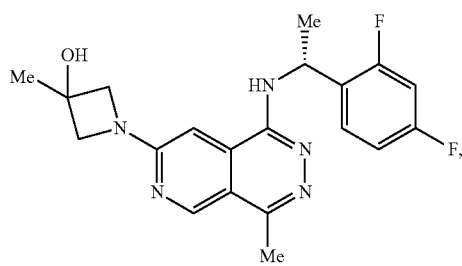
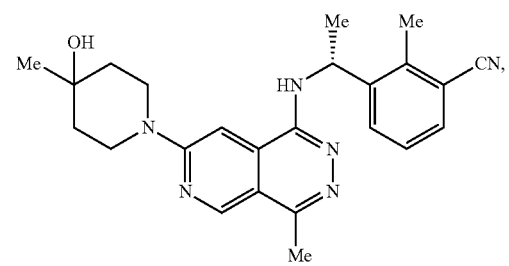
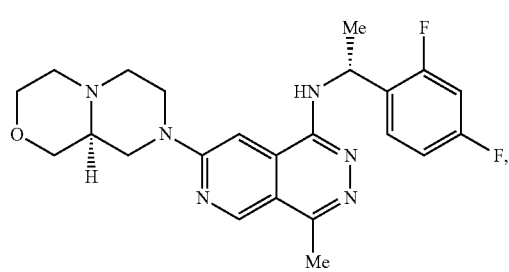
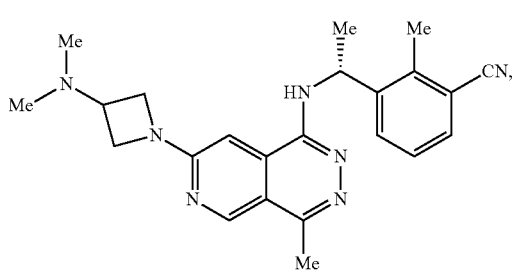
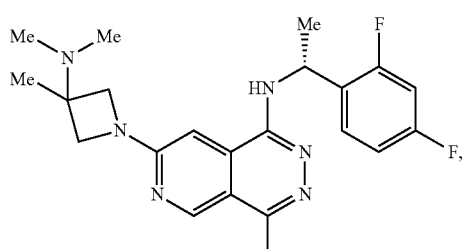
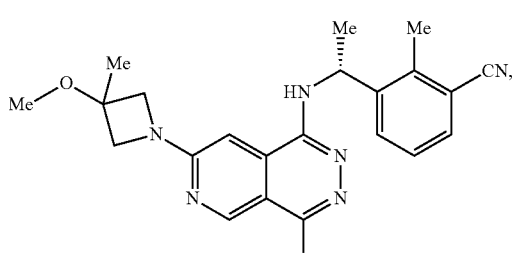
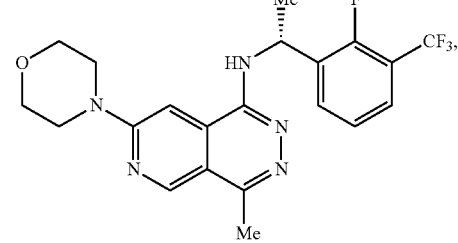
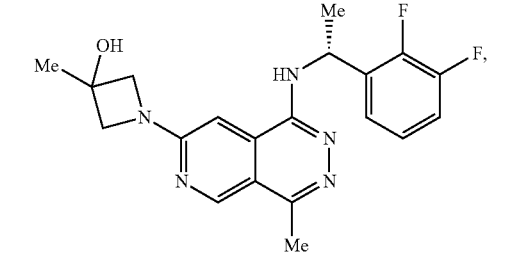
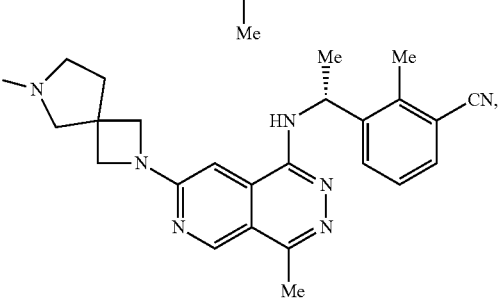
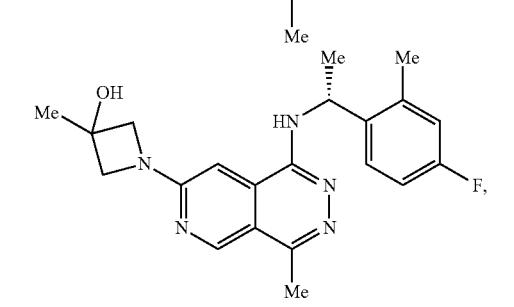

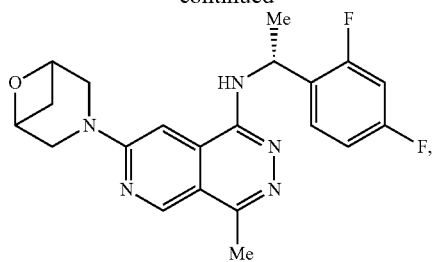
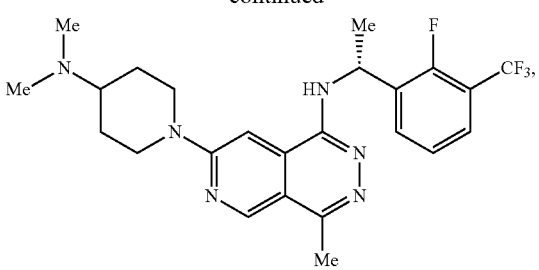
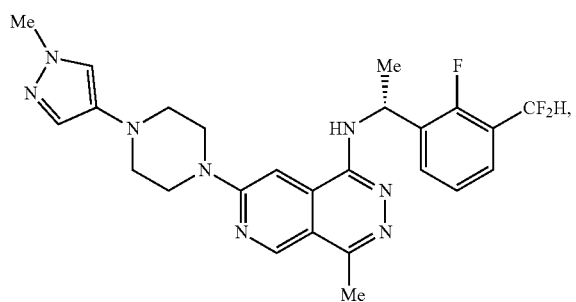
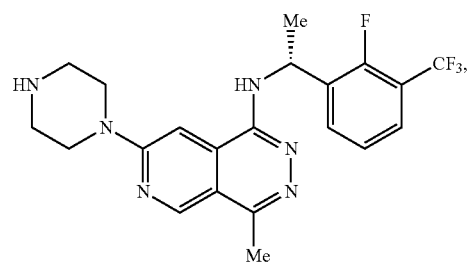
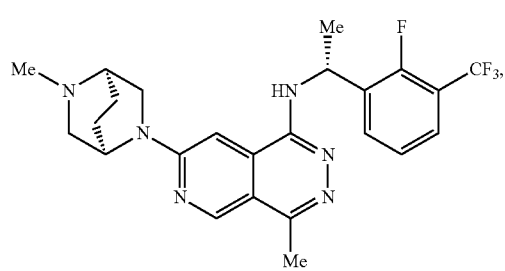
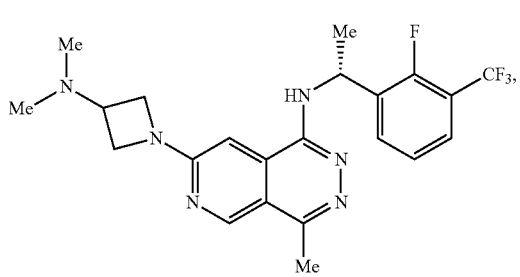
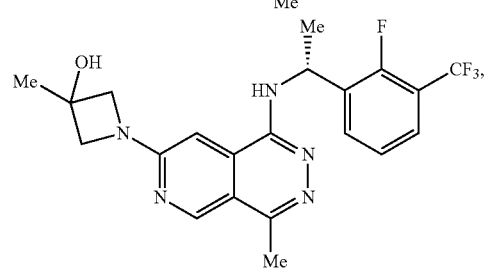
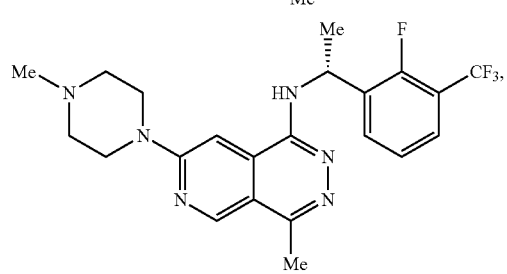
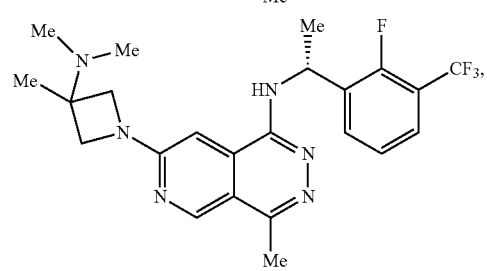
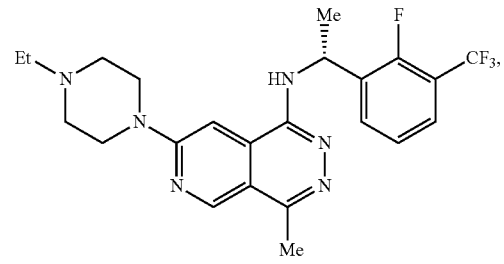
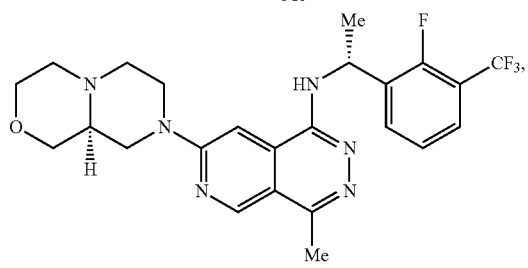
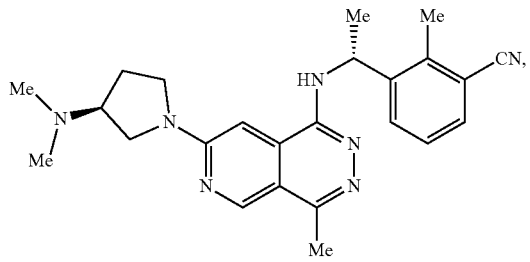

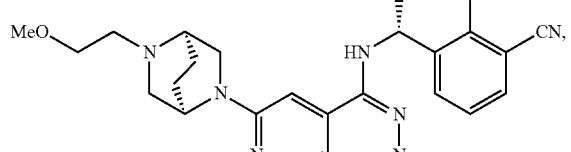
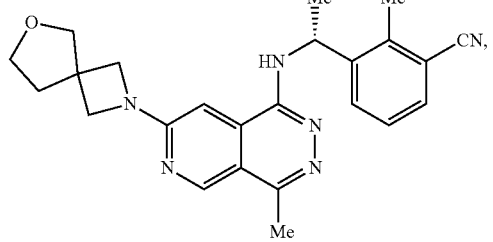
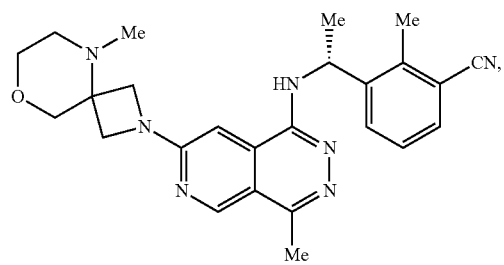
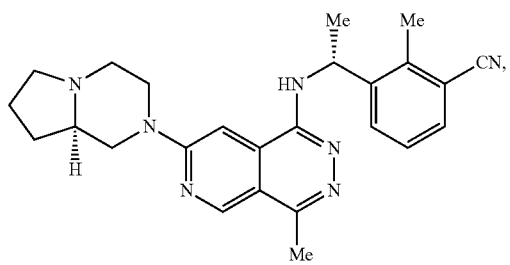
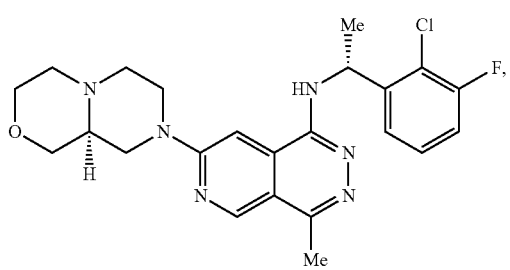
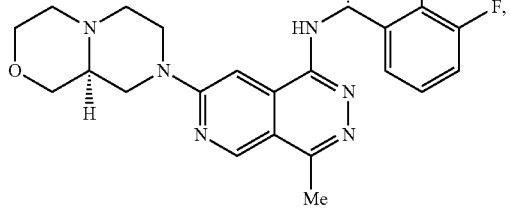
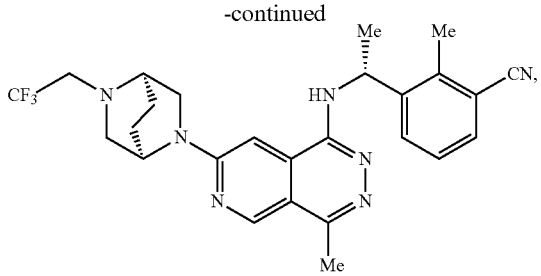
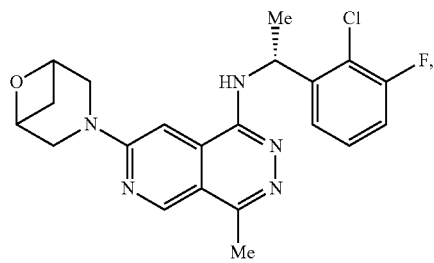
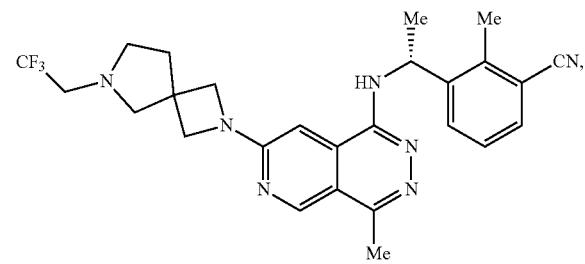
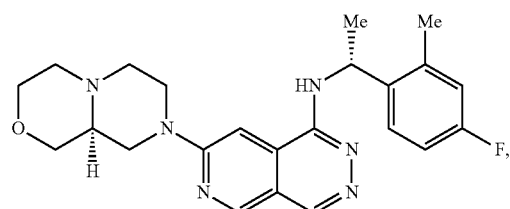
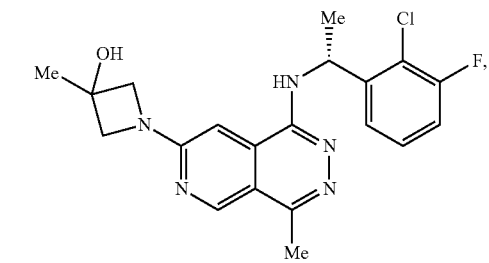
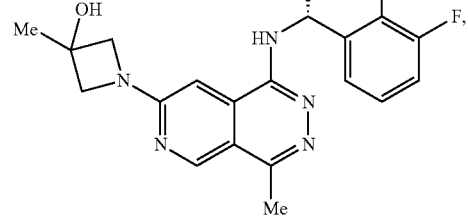

65
-continued
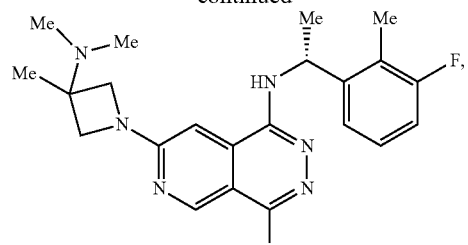
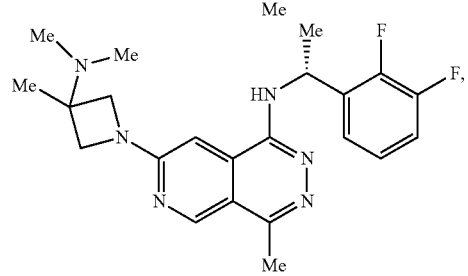
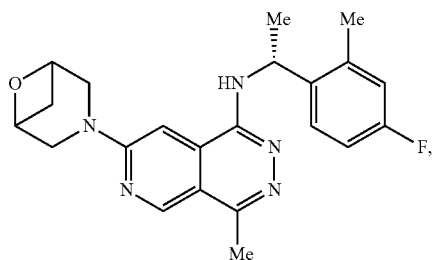
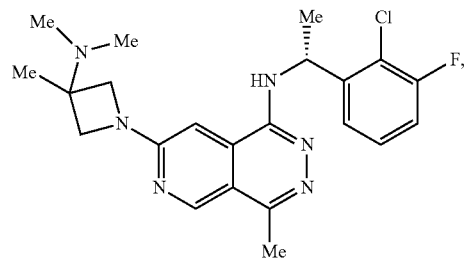
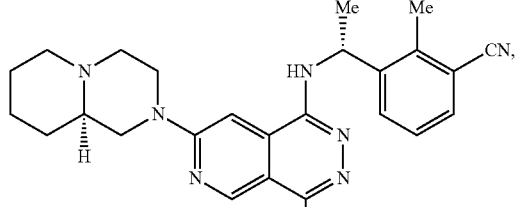
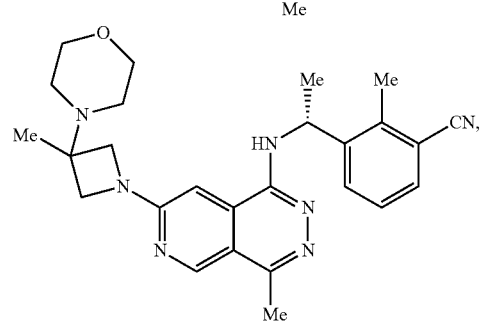
66
-continued
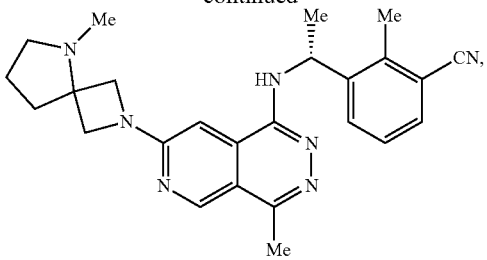
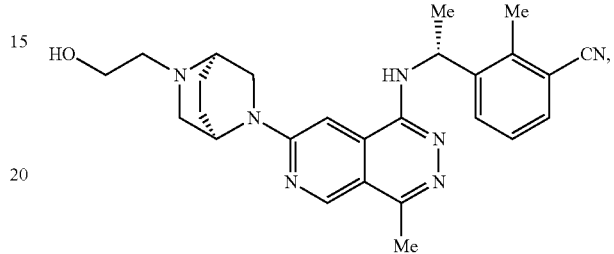
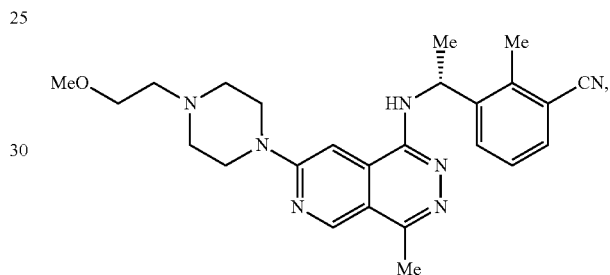
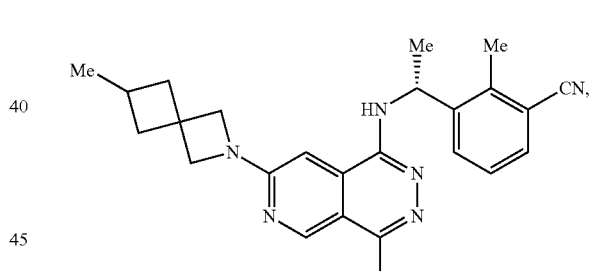
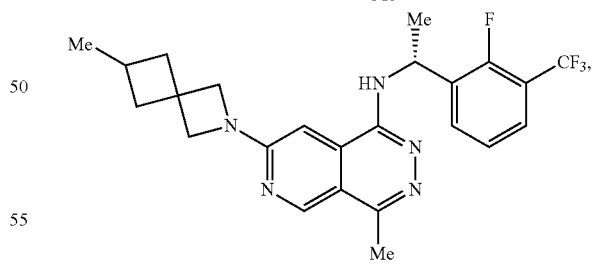
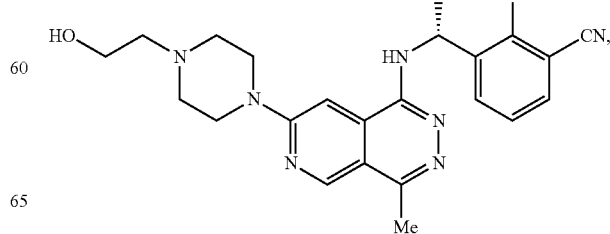

67
-continued
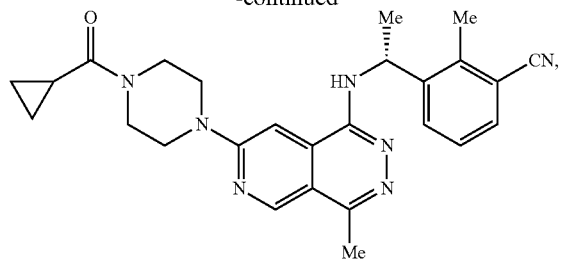
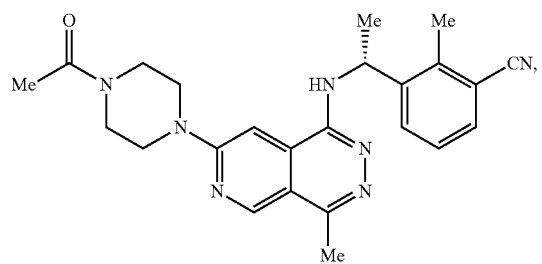
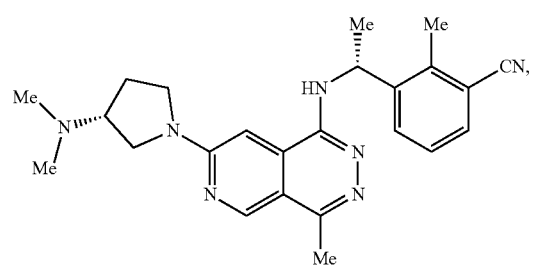
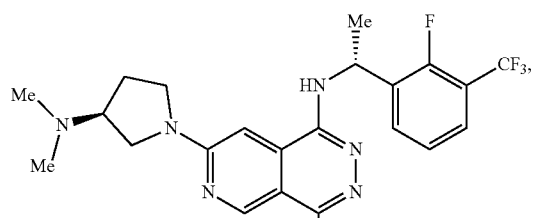
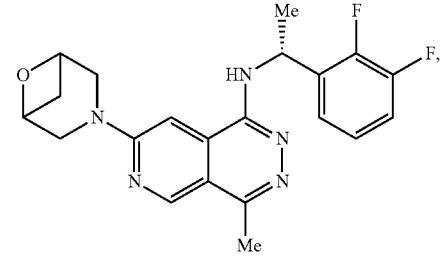
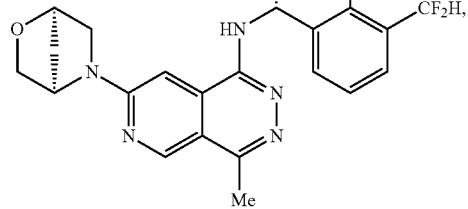
68
-continued
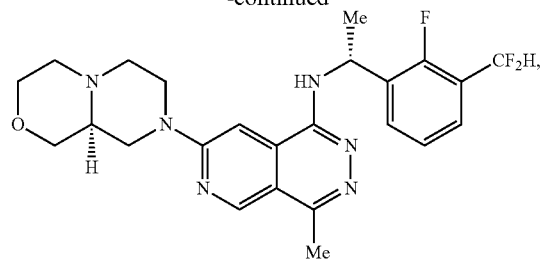
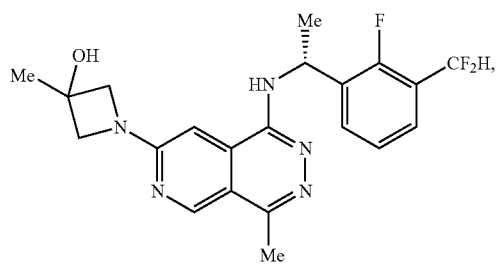
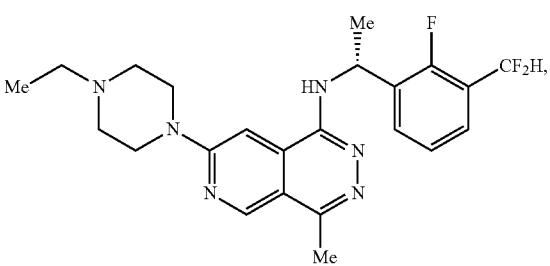
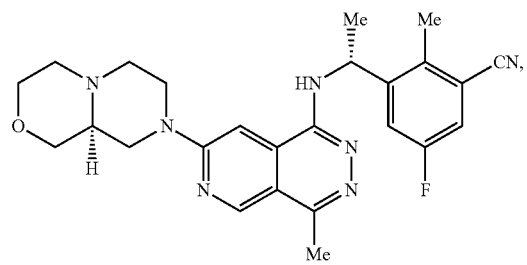
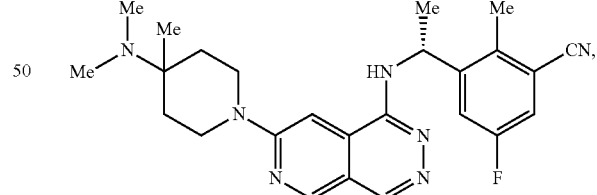
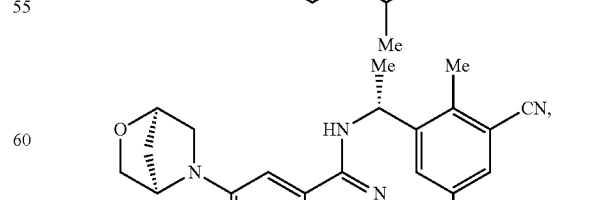
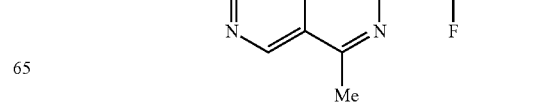

-continued
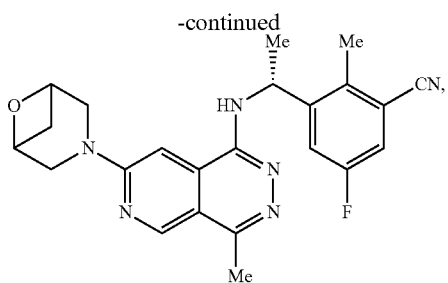
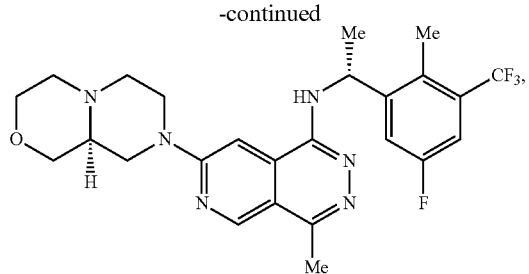
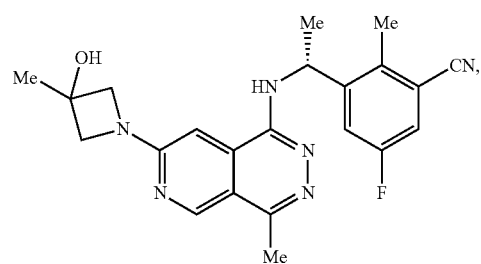
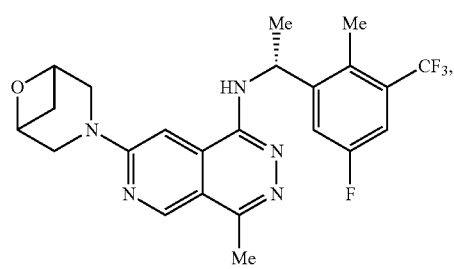
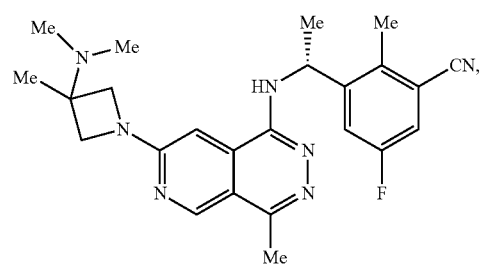
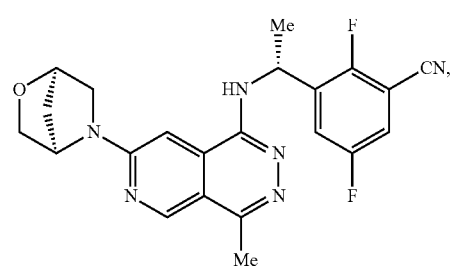
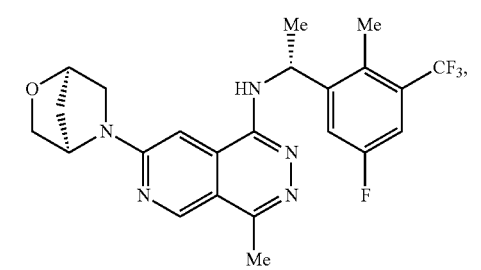
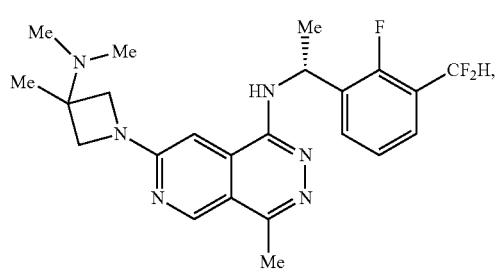
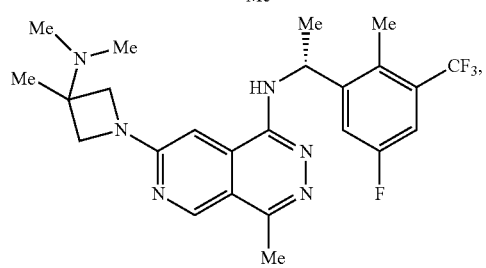
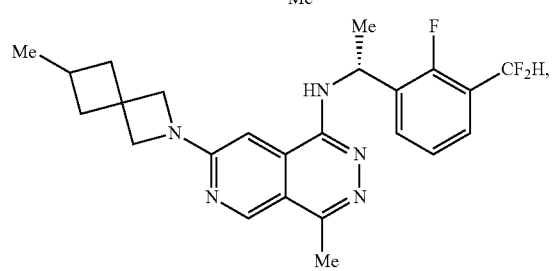
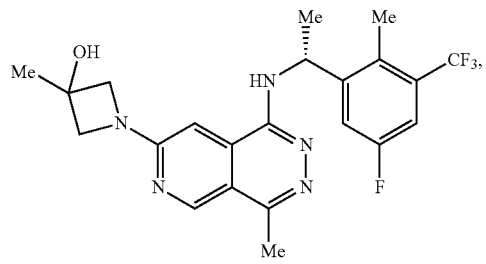
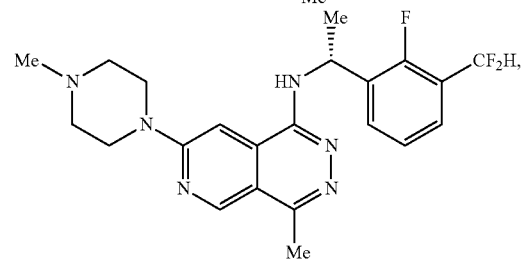

-continued
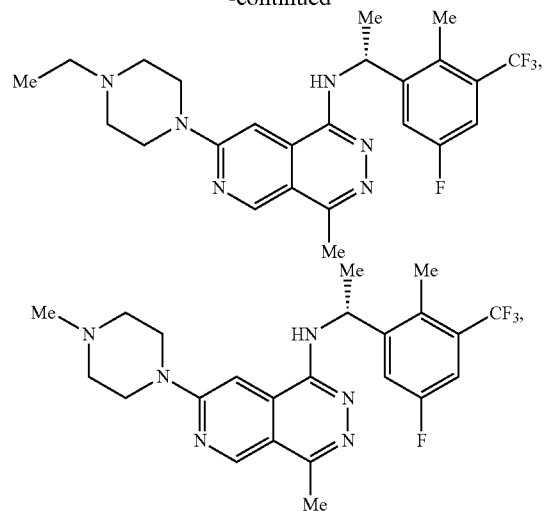
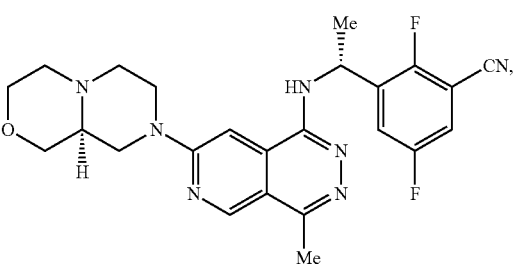
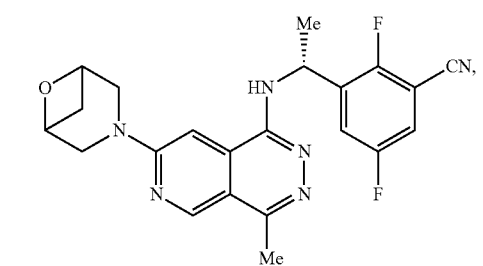
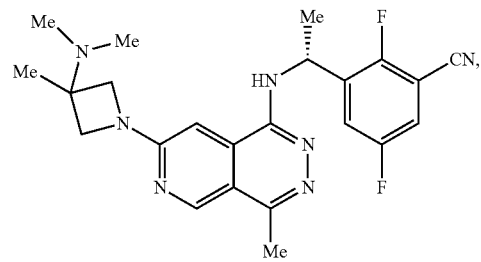
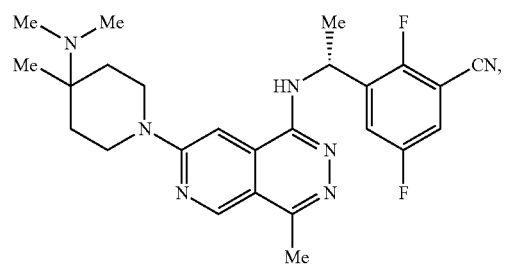
-continued
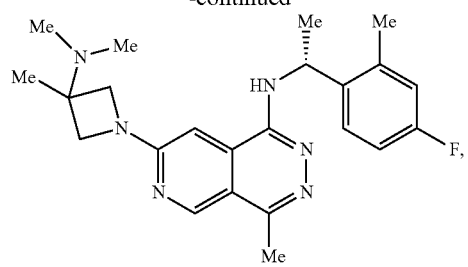
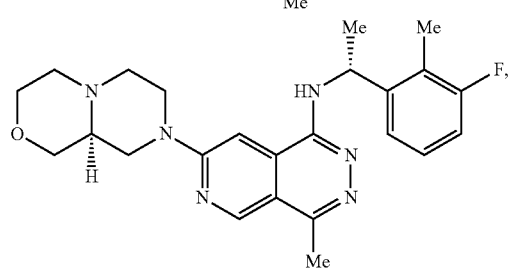
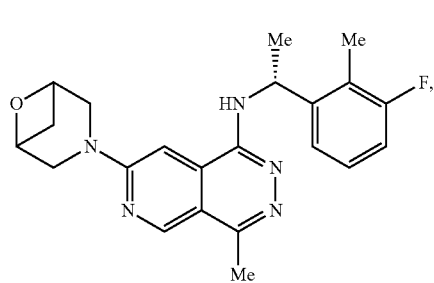
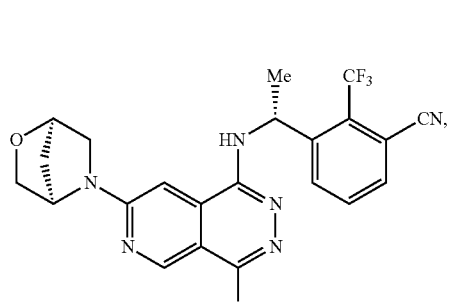
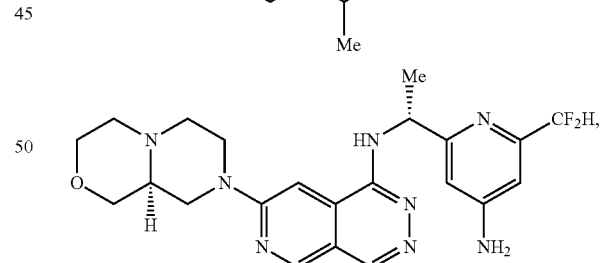
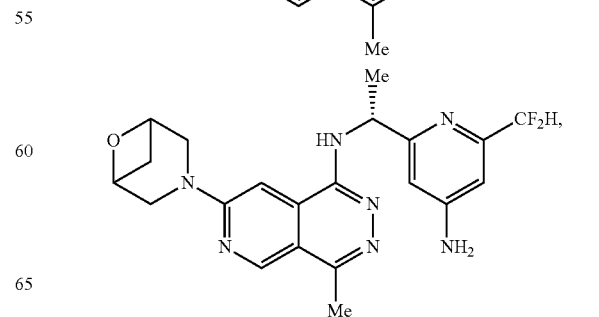

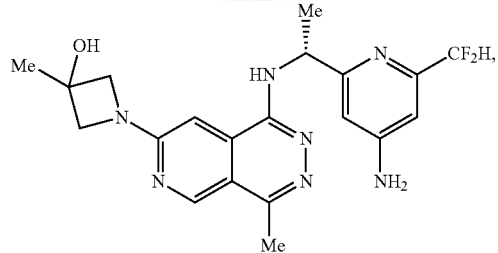
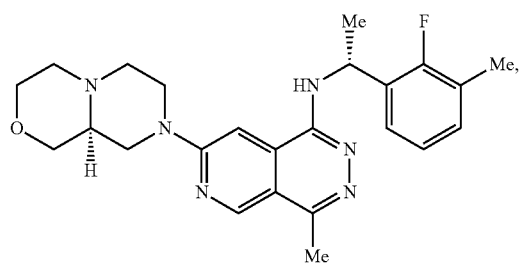
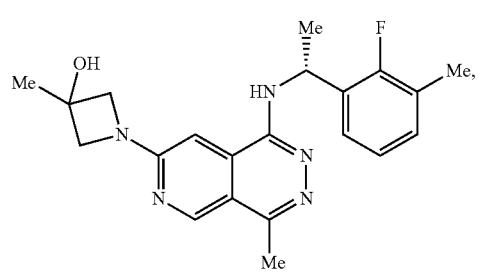
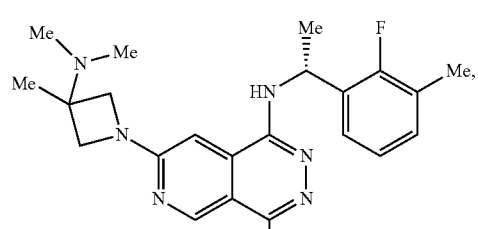
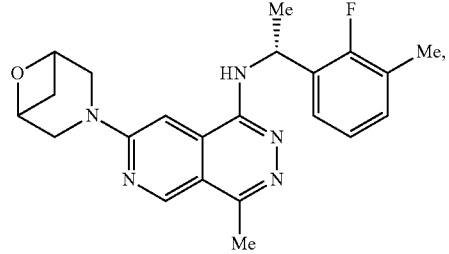
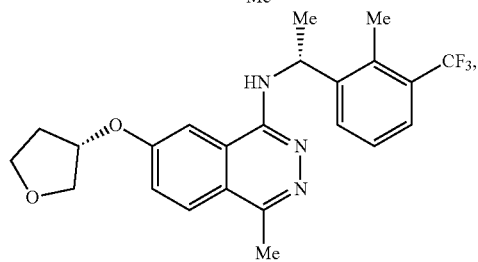
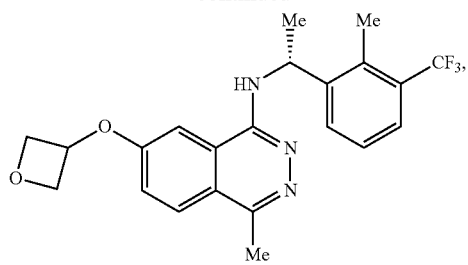
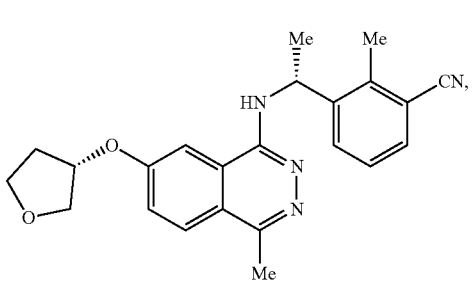
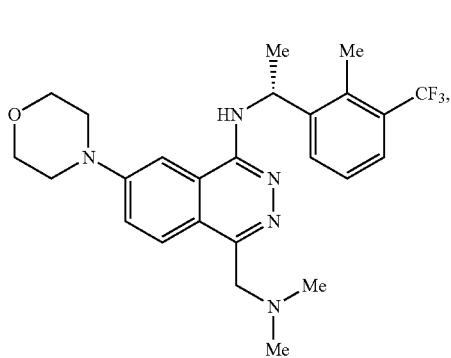
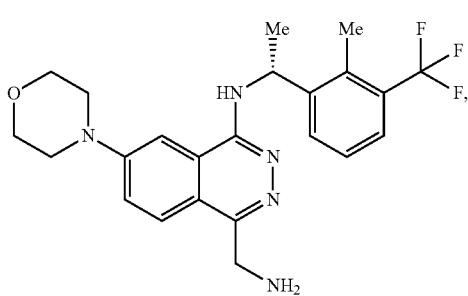
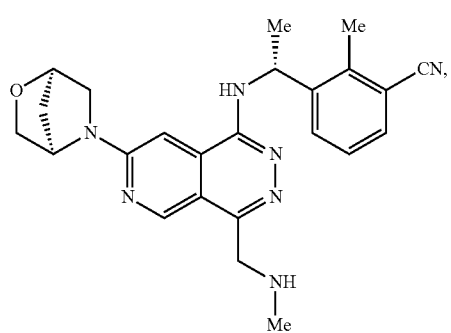

75
-continued
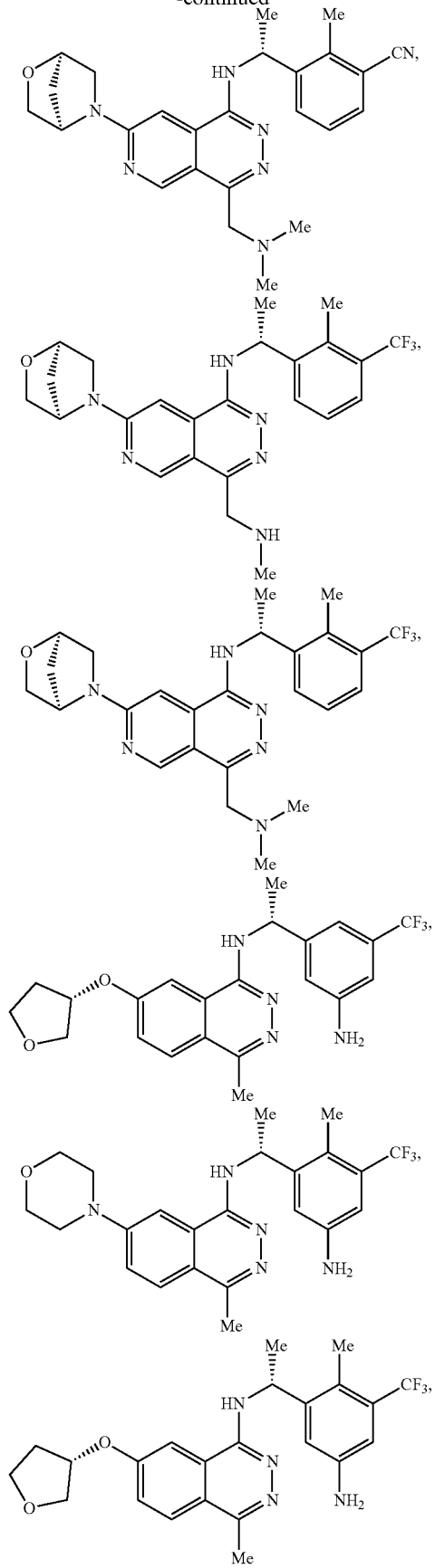
76
-continued
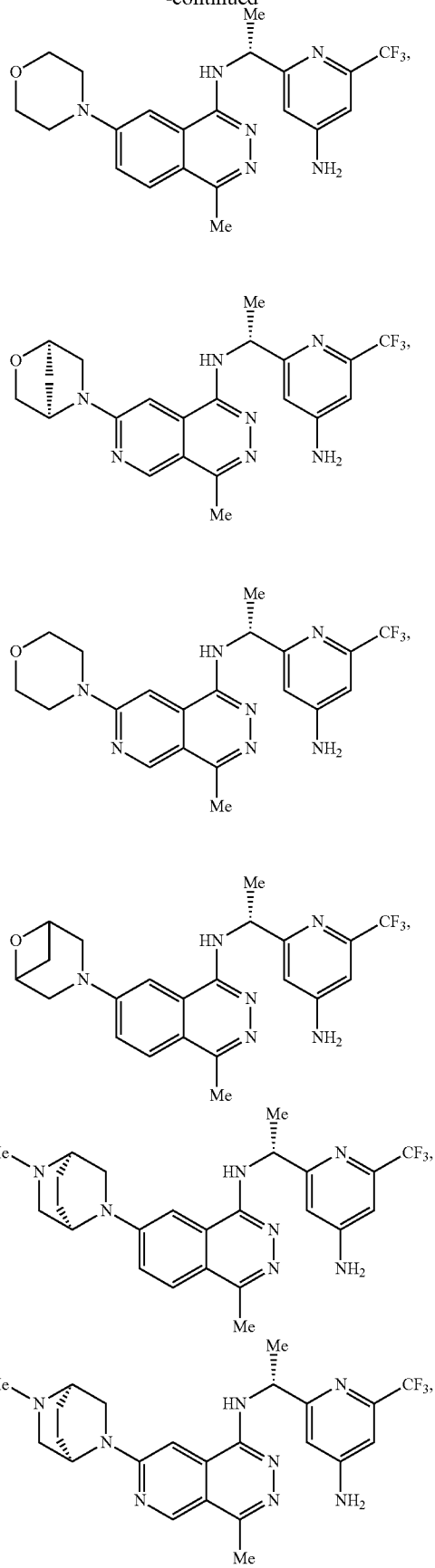

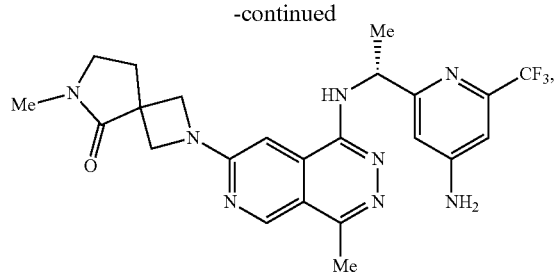
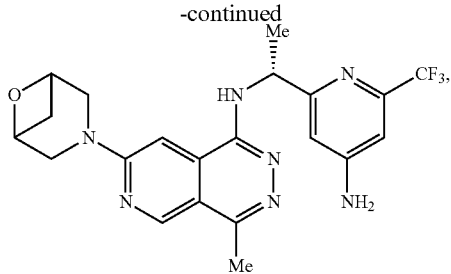
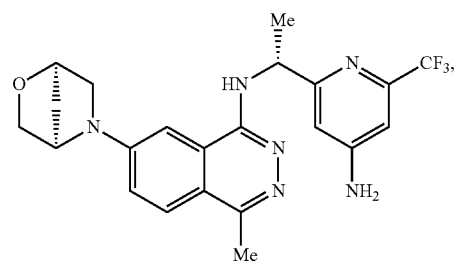
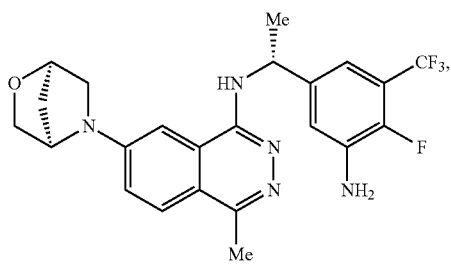
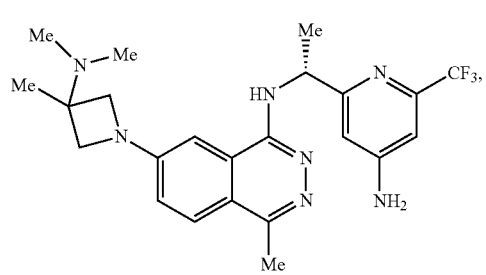
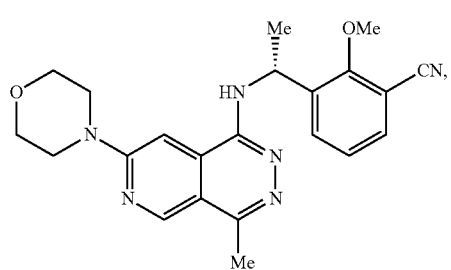
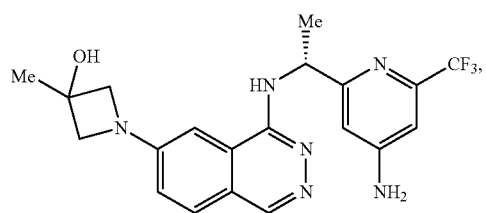
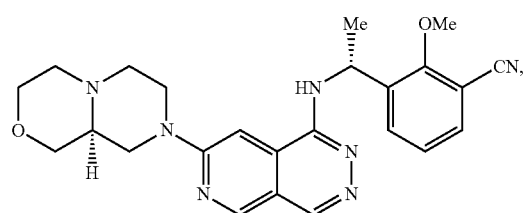
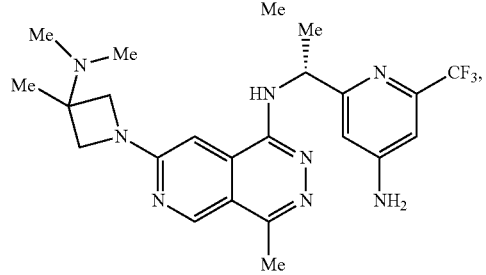
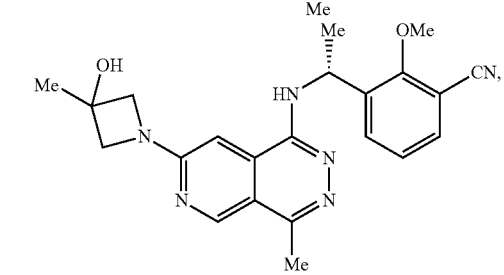
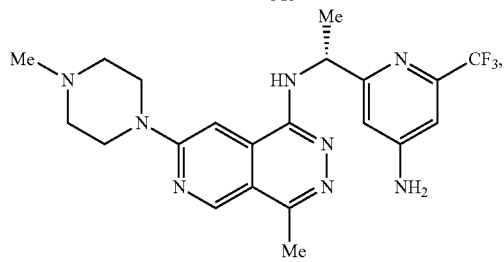
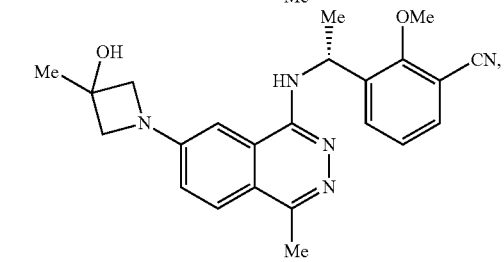

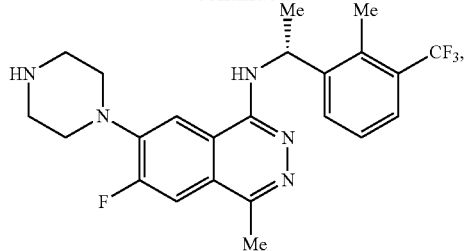
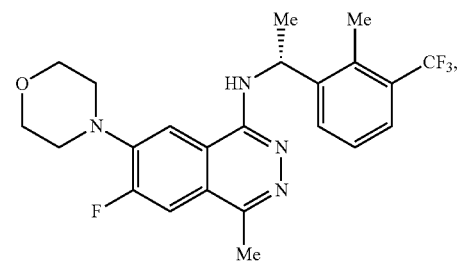
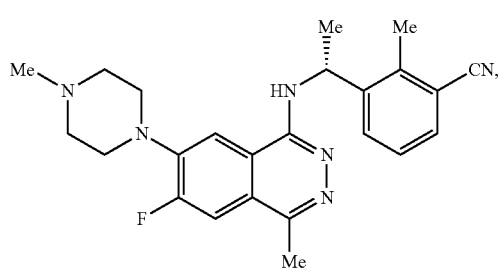
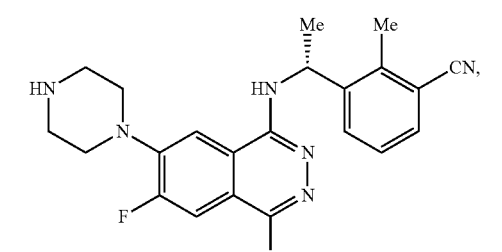
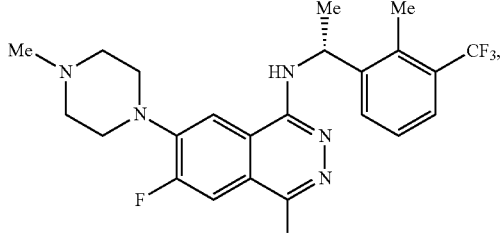
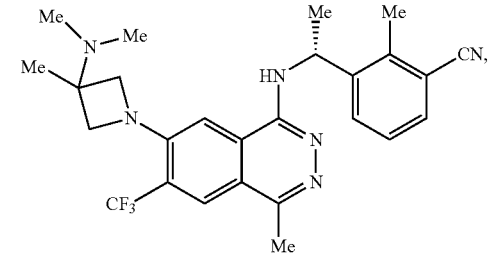
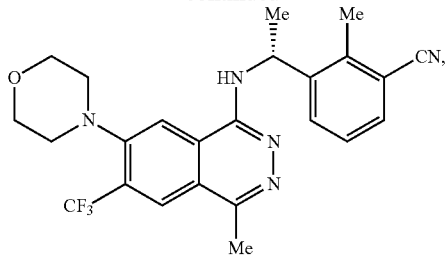
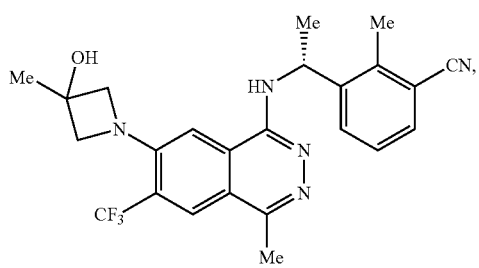
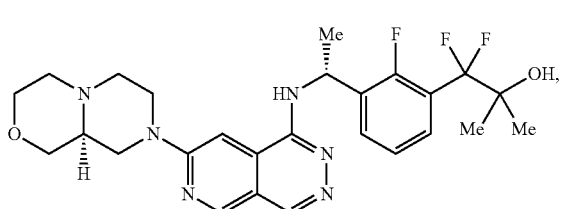
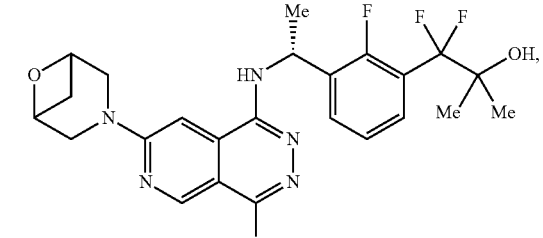
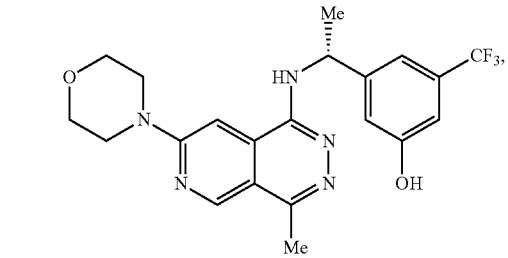

-continued

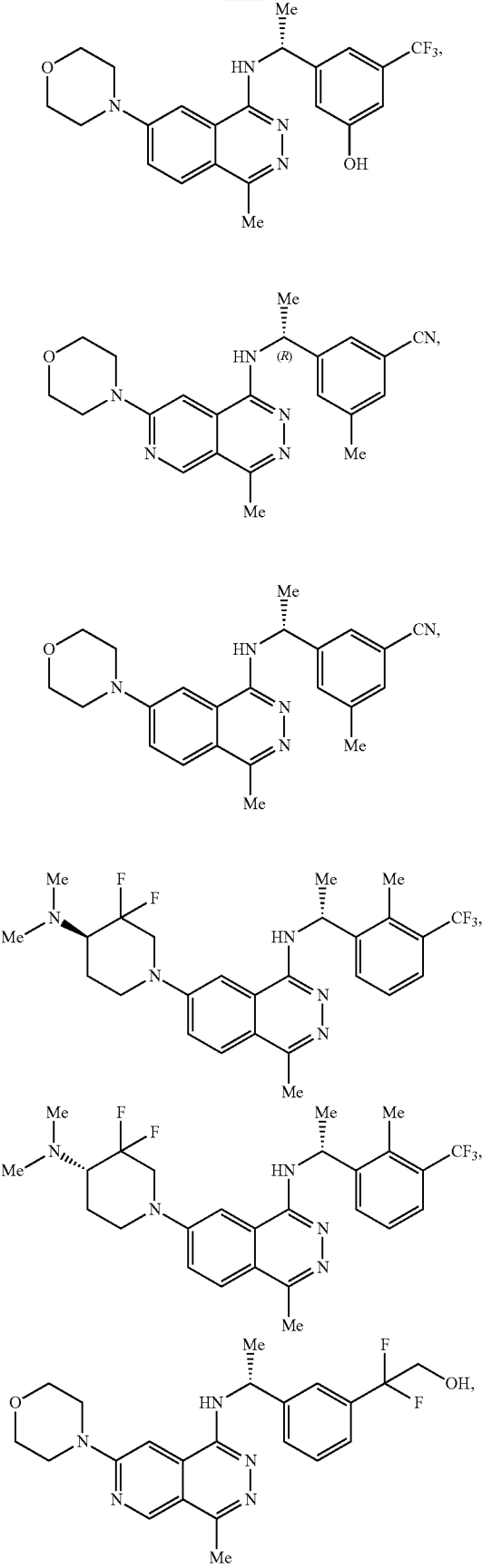

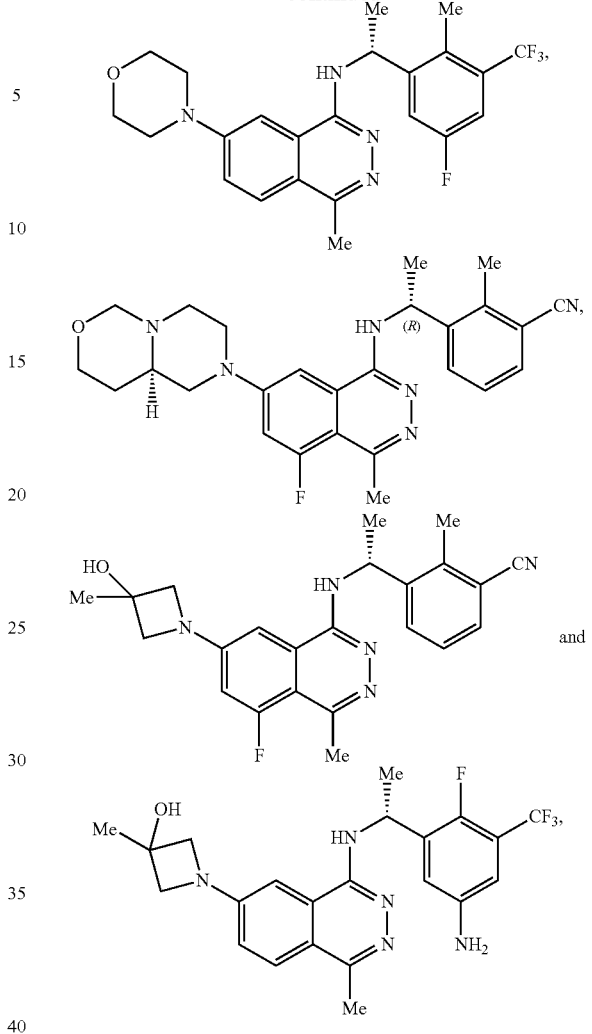

and pharmaceutically acceptable salts thereof.

In another embodiment the SOS1 inhibitor is a compound of the formula:

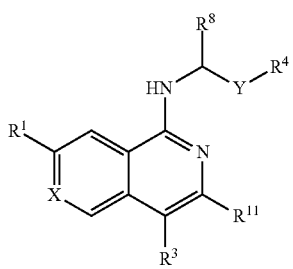

or a pharmaceutically acceptable salt thereof, wherein: $R^1$ is hydrogen, hydroxy, C1-C6 alkyl, alkoxy, —$N(R^6)_2$, —$NR^6C(O)R^6$, —$C(O)N(R^6)_2$, —$SO_2$alkyl, —$SO_2NR^6$alkyl, cycloalkyl, -Q-heterocyclyl, aryl, or heteroaryl, wherein the cycloalkyl, the heterocyclyl, the aryl, and the heteroaryl are each optionally substituted with one or more $R^2$; each Q is independently a bond or O; X is N or $CR^7$; each $R^2$ is independently hydroxy, halogen, cyano, hydroxyalkyl, alkoxy, —$N(R^6)_2$, —$SO_2$alkyl, —$NR^6C(O)R^6$, C1-C3 alkyl, haloalkyl, cycloalkyl or aryl; $R^3$ is hydrogen, halogen, cyano, C1-C6 alkyl, alkoxy, —N(R$^{10}$)$_2$, —NR$^{10}$C(O)NR$^{10}$, —C(O)N(R$^{10}$)$_2$, —SO$_2$alkyl, —SO$_2$NR$^{10}$alkyl, —SO$_2$N(R$^{10}$)$_2$, cycloalkyl, haloalkyl, heterocyclyl, aryl, or heteroaryl, wherein the C1-C6 alkyl, cycloalkyl, the heterocyclyl, the aryl, and the heteroaryl are each optionally substituted with one or more R$^9$; Y is a bond or heteroarylene; R$^4$ is aryl or heteroaryl, each optionally substituted with one or more R$^5$; each R$^5$ is independently hydroxy, halogen, cyano, hydroxyalkyl, alkoxy, C1-C3 alkyl, haloalkyl or -L-N(R$^6$)$_2$; L is C1-C3 alkylene; each R$^6$ is independently hydrogen, C1-C3 alkyl or cycloalkyl; R$^7$ is hydrogen or alkoxy; R$^8$ is C1-C2 alkyl or halo-C1-C2 alkyl; each R$^9$ is independently hydroxy, halogen, amino, cyano, alkoxy, or C1-C6 alkyl; each R$^{10}$ is independently hydrogen, C1-C3 alkyl or cycloalkyl; and R$^{11}$ is hydrogen, C1-C3 alkyl, cycloalkyl, or haloalkyl. These compounds include, but are not limited to, compounds such as:

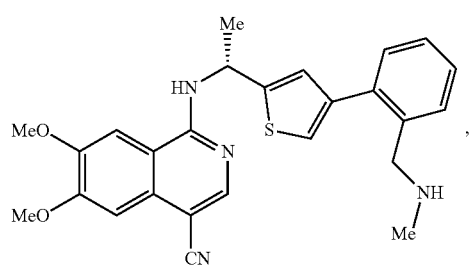

,

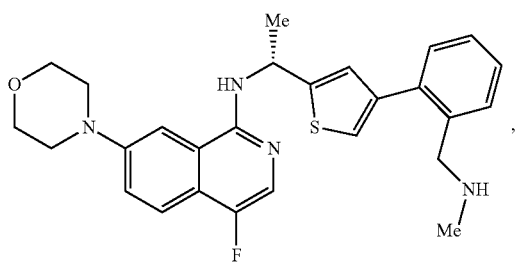

,

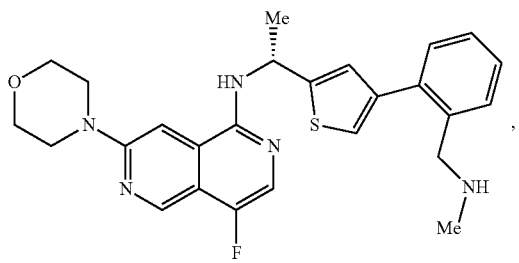

,

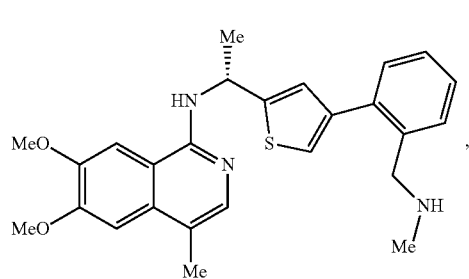

,

-continued

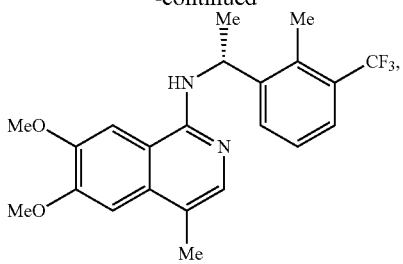

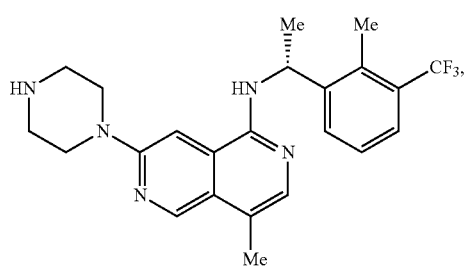

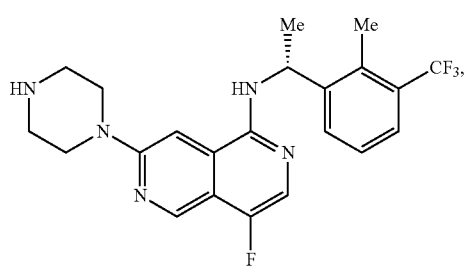

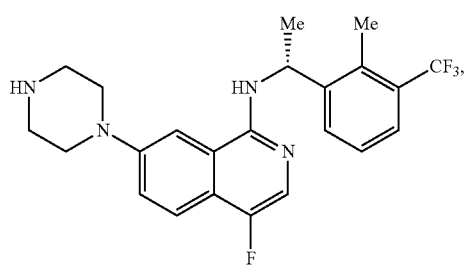

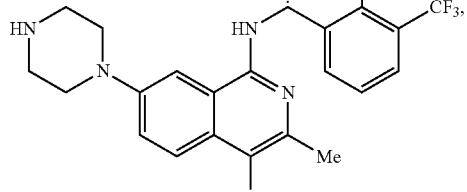

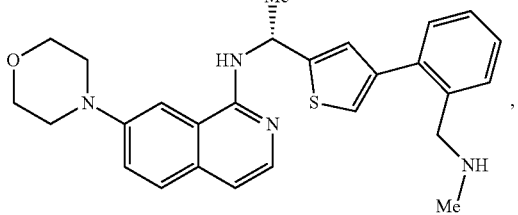

,

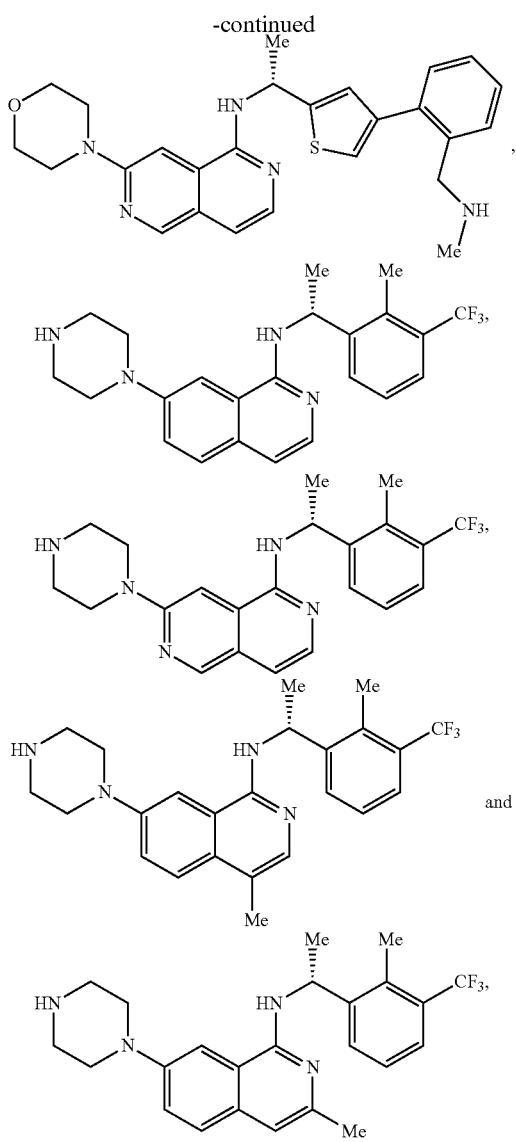

and pharmaceutically acceptable salts thereof.

In another embodiment the SOS1 inhibitor is a compound of the formula:

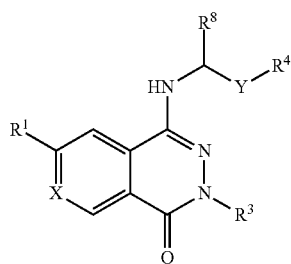

or a pharmaceutically acceptable salt thereof, wherein: $R^1$ is hydrogen, hydroxyl, C1-C6 alkyl, alkoxy, —N($R^6$)$_2$, —N$R^6$C(O)$R^6$, —C(O)N($R^6$)$_2$, —SO$_2$alkyl, —SO$_2$N$R^6$alkyl, -Q-heterocyclyl, aryl, or heteroaryl, wherein the cycloalkyl, the heterocyclyl, the aryl, or the heteroaryl are each optionally substituted with one or more $R^2$; each Q is independently a bond, O or N$R^6$; X is N or C$R^7$; with the proviso that when X is N, $R^1$ is not hydroxyl; each $R^2$ is independently hydroxy, halogen, cyano, hydroxyalkyl, haloalkyl, alkoxy, —N($R^6$)$_2$, —SO$_2$alkyl, —N$R^6$C(O)C1-C3 alkyl, —C(O)cycloalkyl, —C(O)heretocyclyl or aryl, wherein the cycloalkyl, the heterocyclyl or the aryl are each optionally substituted with one or more $R^9$; $R^3$ is hydrogen, C1-C3 alkyl, C1-C3 haloalkyl, or cycloalkyl; Y is a bond or heteroarylene; $R^4$ is aryl or heteroaryl, each optionally substituted with one or more $R^5$; each $R^5$ is independently hydroxy, halogen, cyano, hydroxyalkyl, alkoxy, C1-C4 alkyl, haloalkyl, —N($R^6$)$_2$, -L-N($R^6$)$_2$ or —SO$_2$alkyl; L is C1-C3 alkylene; each $R^6$ is independently hydrogen, C1-C3 alkyl, haloalkyl or cycloalkyl; $R^7$ is hydrogen, cyano or alkoxy; $R^8$ is C1-C2 alkyl or halo-C1-C2 alkyl; and each $R^9$ is independently C1-C3 alkyl or haloalkyl. These compounds include, but are not limited to, compounds such as:

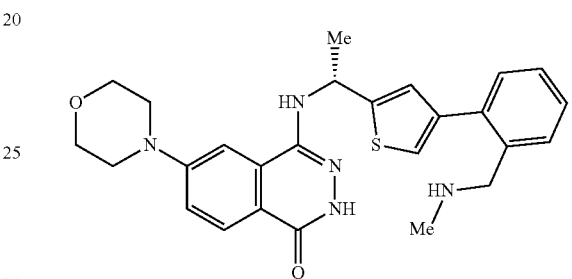

,

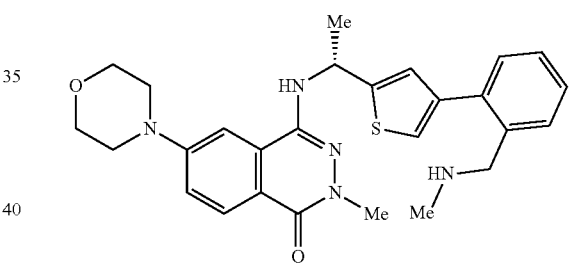

,

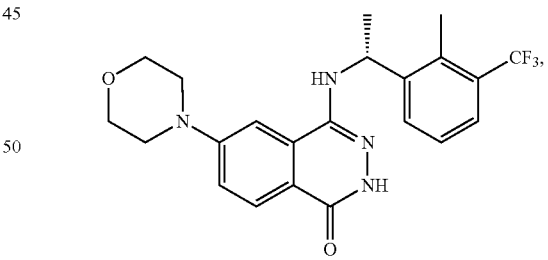

,

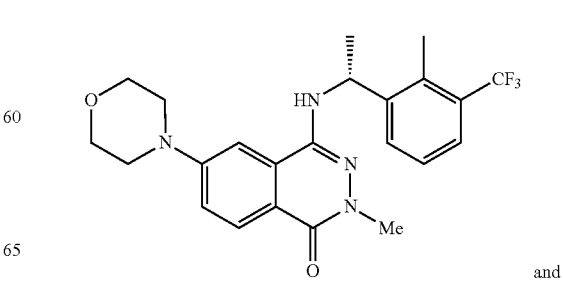

and

-continued

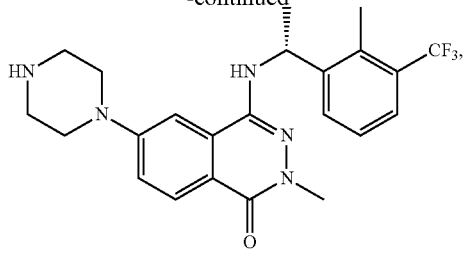

and pharmaceutically acceptable salts thereof.

In another embodiment, the SOS1 inhibitor is a compound selected from:

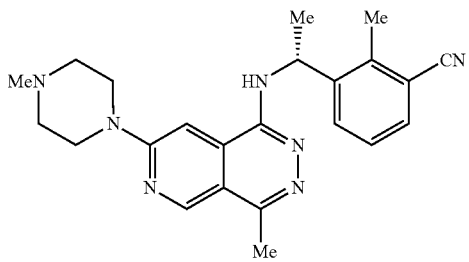 [SMILES: Cc1c(C#N)cccc1[C@@H](C)Nc1nnc(C)c2cnc(N3CCN(C)CC3)cc12]

(R)-2-methyl-3-(1-((4-methyl-7-morpholinopyrido[3,4-d]pyridazin-1-yl)amino)ethyl)benzonitrile,

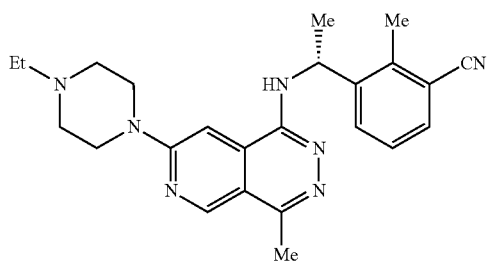 [SMILES: CCN1CCN(c2cc3c(N[C@H](C)c4cccc(C#N)c4C)nnc(C)c3cn2)CC1]

3-((R)-1-((7-((S)-hexahydropyrazino[2,1-c][1,4]oxazin-8(1H)-yl)-4-methylpyrido[3,4-d]pyridazin-1-yl)amino)ethyl)-2-methylbenzonitrile,

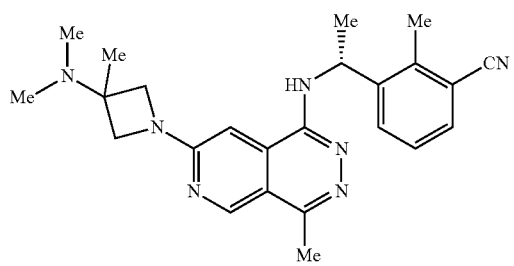

(R)-3-(1-((7-(3-(dimethylamino)-3-methylazetidin-1-yl)-4-methylpyrido[3,4-d]pyridazin-1-yl)amino)ethyl)-2-methylbenzonitrile, and

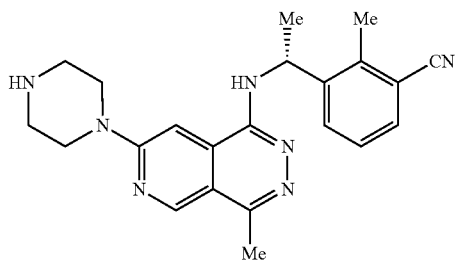 [SMILES: Cc1c(C#N)cccc1[C@@H](C)Nc1nnc(C)c2cnc(N3CCNCC3)cc12]

(R)-2-methyl-3-(1-((4-methyl-7-(4-methylpiperazin-1-yl)pyrido[3,4-d]pyridazin-1-yl)amino)ethyl)benzonitrile,

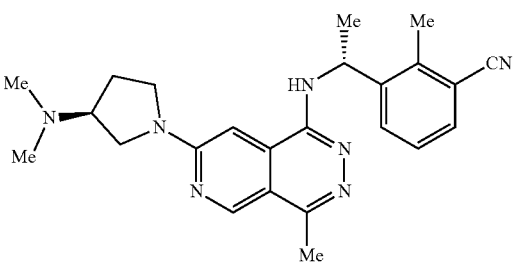 [SMILES: Cc1c(C#N)cccc1[C@@H](C)Nc1nnc(C)c2cnc(N3CC[C@H](N(C)C)C3)cc12]

(R)-3-(1-((7-(4-ethylpiperazin-1-yl)-4-methylpyrido[3,4-d]pyridazin-1-yl)amino)ethyl)-2-methylbenzonitrile, (R)-2-methyl-3-(1-((4-methyl-7-(piperazin-1-yl)pyrido[3,4-d]pyridazin-1-yl)amino)ethyl)benzonitrile, and 3-((R)-1-((7-((S)-3-(dimethylamino)pyrrolidin-1-yl)-4-methylpyrido[3,4-d]pyridazin-1-yl)amino)ethyl)-2-methylbenzonitrile,

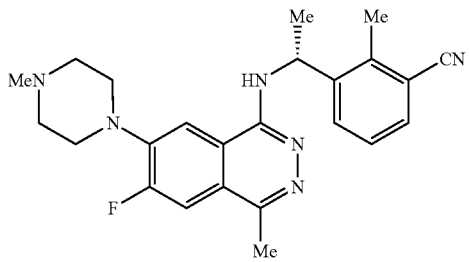

(R)-3-(1-((6-fluoro-4-methyl-7-(4-methylpiperazin-1-yl)phthalazin-1-yl)amino)ethyl)-2-methylbenzonitrile, and pharmaceutically acceptable salts thereof.

The SOS1 inhibitors used in the methods of the present invention may have one or more chiral center and may be synthesized as stereoisomeric mixtures, isomers of identical constitution that differ in the arrangement of their atoms in space. The compounds may be used as mixtures or the individual components/isomers may be separated using commercially available reagents and conventional methods for isolation of stereoisomers and enantiomers well-known to those skilled in the art, e.g., using CHIRALPAK® (Sigma-Aldrich) or CHIRALCEL® (Diacel Corp) chiral chromatographic HPLC columns according to the manufacturer's instructions. Alternatively, compounds of the present invention may be synthesized using optically pure, chiral reagents and intermediates to prepare individual isomers or enantiomers. Unless otherwise indicated, all chiral (enantiomeric and diastereomeric) and racemic forms are within the scope of the invention. Unless otherwise indicated, whenever the specification, including the claims, refers to compounds of the invention, the term "compound" is to be understood to encompass all chiral (enantiomeric and diastereomeric) and racemic forms.

In one embodiment, the SOS1 inhibitor compound includes its salts, for instance salts formed with inorganic acids such as hydrochloric acid, hydrobromic acid, sulfuric acid, phosphoric acid, nitric acid, salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid, and salts formed from quaternary ammoniums of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

Methods for manufacturing the SOS1 inhibitors disclosed herein are known. For example, commonly owned application Nos. 62/951,812, 62/975,645, 63/044,802, 62/980,790 and 63/057,563, and corresponding international applications and publications PCT/US2020/066003 (WO21/127429), PCT/US2021/019184 (WO 2021/173524) and PCT/US2021/043309 (WO 2022/026465), describe general reaction schemes for preparing compounds and also provide detailed synthetic routes for the preparation of these compounds.

Pharmaceutical Compositions

The SOS1 inhibitors and the KRas G12C compound adagrasib or pharmaceutically acceptable salts thereof may be formulated into pharmaceutical compositions.

In another aspect, the invention provides pharmaceutical compositions comprising a SOS1 inhibitor, or a pharmaceutically acceptable salt thereof, and the KRas G12C inhibitor adagrasib, or a pharmaceutically acceptable salt thereof and a pharmaceutically acceptable carrier, excipient, or diluent that may be used in the methods disclosed herein. The SOS1 inhibitor, or a pharmaceutically acceptable salt thereof, and KRas G12C inhibitor, or a pharmaceutically acceptable salt thereof may be independently formulated by any method well known in the art and may be prepared for administration by any route, including, without limitation, parenteral, oral, sublingual, transdermal, topical, intranasal, intratracheal, or intrarectal. In certain embodiments, SOS1 inhibitor, or a pharmaceutically acceptable salt thereof, and KRas G12C inhibitor, or a pharmaceutically acceptable salt thereof, are administered intravenously in a hospital setting. In one embodiment, administration may be by the oral route.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

As used herein, the term "pharmaceutically acceptable salt" refers to salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The active compound is included in the pharmaceutically acceptable carrier or diluent in an amount sufficient to deliver to a patient a therapeutically effective amount without causing serious toxic effects in the patient treated. In one embodiment, a dose of the active compound for all of the above-mentioned conditions is in the range from about 0.01 to 300 mg/kg, for example 0.1 to 100 mg/kg per day, and as a further example 0.5 to about 25 mg per kilogram body weight of the recipient per day. A typical topical dosage will range from 0.01-3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The pharmaceutical compositions comprising a SOS1 inhibitor, or a pharmaceutically acceptable salt or a pharmaceutical composition thereof and a KRas G12C inhibitor, or a pharmaceutically acceptable salt or a pharmaceutical composition thereof, may be used in the methods of use described herein.

Co-Administration

The SOS1 inhibitor, or a pharmaceutically acceptable salt thereof, and the KRas G12C inhibitor, or a pharmaceutically acceptable salt thereof, can be formulated into separate or individual dosage forms which can be co-administered one after the other. Another option is that if the route of administration is the same (e.g. oral) two active compounds can be formulated into a single form for co-administration, both methods of co-administration, however, being part of the same therapeutic treatment or regimen.

The pharmaceutical compositions comprising a SOS1 inhibitor, or a pharmaceutically acceptable salt thereof, and/or a KRas G12C inhibitor, or a pharmaceutically acceptable salt thereof, for use in the methods may be for simultaneous, separate or sequential use. In one embodiment, the SOS1 inhibitor or a pharmaceutically acceptable salt thereof, is administered prior to administration of the KRas G12C inhibitor compound adagrasib or a pharmaceutically acceptable salt thereof. In another embodiment, the SOS1 inhibitor, or a pharmaceutically acceptable salt thereof, is administered after administration of the KRas G12C inhibitor compound adagrasib or a pharmaceutically acceptable salt thereof. In another embodiment, the SOS1 inhibitor, or a pharmaceutically acceptable salt thereof, is administered at about the same time as administration of the KRas G12C inhibitor compound adagrasib or a pharmaceutically acceptable salt thereof.

Separate administration of each inhibitor, at different times and by different routes, in some cases would be advantageous. Thus, the components in the combination i.e. the KRas G12C inhibitor compound adagrasib or a pharmaceutically acceptable salt thereof and the SOS1 inhibitor, or a pharmaceutically acceptable salt thereof, need not be necessarily administered at essentially the same time or in any order.

Oncology drugs are typically administered at the maximum tolerated dose ("MTD"), which is the highest dose of drug that does not cause unacceptable side effects. In one embodiment, the KRas G12C inhibitor, or a pharmaceutically acceptable salt or a pharmaceutical composition thereof and the SOS1 inhibitor, or a pharmaceutically acceptable salt or a pharmaceutical composition thereof, are each dosed at their respective MTDs. In one embodiment, the KRas G12C inhibitor, or a pharmaceutically acceptable salt or a pharmaceutical composition thereof, is dosed at its MTD and the SOS1 inhibitor, or a pharmaceutically acceptable salt or a pharmaceutical composition thereof, is dosed in an amount less than its MTD. In one embodiment, the KRas G12C inhibitor, or a pharmaceutically acceptable salt or a pharmaceutical composition thereof, is dosed at an amount less than its MTD and the SOS1 inhibitor, or a pharmaceutically acceptable salt or a pharmaceutical composition thereof, is dosed at its MTD. In one embodiment, the KRas G12C inhibitor, or a pharmaceutically acceptable salt or a pharmaceutical composition thereof and the SOS1 inhibitor, or a pharmaceutically acceptable salt or a pharmaceutical composition thereof are each dosed at less than their respective MTDs. The administration can be so timed that the peak pharmacokinetic effect of one compound coincides with the peak pharmacokinetic effect of the other.

In one embodiment, a single dose of KRas G12C inhibitor compound adagrasib or a pharmaceutically acceptable salt or a pharmaceutical composition thereof, is administered per day (i.e., in about 24 hour intervals) (i.e., QD). In another embodiment, two doses of the KRas G12C inhibitor compound adagrasib or a pharmaceutically acceptable salt or a pharmaceutical composition thereof, are administered per day (i.e., BID). In another embodiment, three doses of the KRas G12C inhibitor compound adagrasib or a pharmaceutically acceptable salt or a pharmaceutical composition thereof, are administered per day (i.e., TID).

In one embodiment, the SOS1 inhibitor, or a pharmaceutically acceptable salt or a pharmaceutical composition thereof, is administered QD. In another embodiment the SOS1 inhibitor, or a pharmaceutically acceptable salt or a pharmaceutical composition thereof, are administered BID. In another embodiment, the SOS1 inhibitor, or a pharmaceutically acceptable salt or a pharmaceutical composition thereof, of the invention are administered TID.

In one embodiment, a single dose of KRas G12C inhibitor compound adagrasib or a pharmaceutically acceptable salt or a pharmaceutical composition thereof, and SOS1 inhibitor, or a pharmaceutically acceptable salt or a pharmaceutical composition thereof are each administered once daily.

Examples of SOS1 inhibitors suitable for the provided compositions and methods include those mentioned herein, for example (R)-2-methyl-3-(1-((4-methyl-7-morpholinopyrido[3,4-d]pyridazin-1-yl)amino)ethyl)benzonitrile, 3-((R)-1-((7-((S)-hexahydropyrazino[2,1-c][1,4]oxazin-8 (1H)-yl)-4-methylpyrido[3,4-d]pyridazin-1-yl)amino) ethyl)-2-methylbenzonitrile, (R)-3-(1-((7-(3-(dimethylamino)-3-methylazetidin-1-yl)-4-methylpyrido[3,4-d] pyridazin-1-yl)amino)ethyl)-2-methylbenzonitrile, (R)-2-methyl-3-(1-((4-methyl-7-(4-methylpiperazin-1-yl)pyrido [3,4-d]pyridazin-1-yl)amino)ethyl)benzonitrile, (R)-3-(1-((7-(4-ethylpiperazin-1-yl)-4-methylpyrido[3,4-d] pyridazin-1-yl)amino)ethyl)-2-methylbenzonitrile, (R)-2-methyl-3-(1-((4-methyl-7-(piperazin-1-yl)pyrido[3,4-d] pyridazin-1-yl)amino)ethyl)benzonitrile, 3-((R)-1-((7-((S)-3-(dimethylamino)pyrrolidin-1-yl)-4-methylpyrido[3,4-d] pyridazin-1-yl)amino)ethyl)-2-methylbenzonitrile, and (R)-3-(1-((6-fluoro-4-methyl-7-(4-methylpiperazin-1-yl) phthalazin-1-yl)amino)ethyl)-2-methylbenzonitrile, or a pharmaceutically acceptable salt thereof, or a SOS1 inhibitor such as BI1701963.

Combination Therapies

In one aspect of the invention, provided herein are methods of treating cancer in a subject in need thereof, comprising administering to the subject a therapeutically effective amount of a combination of a SOS1 inhibitor, or a pharmaceutically acceptable salt or a pharmaceutical composition thereof, and the KRasKRas G12C inhibitor compound adagrasib or a pharmaceutically acceptable salt or a pharmaceutical composition thereof. In one embodiment, the cancer is a KRas G12C-associated cancer. In one embodiment, the KRas G12C-associated cancer is lung cancer.

In yet another aspect, the invention provides a method for inhibiting KRas G12C activity in a cell, comprising contacting the cell in which inhibition of KRas G12C activity is desired with an effective amount of a combination of the KRas G12C inhibitor adagrasib:

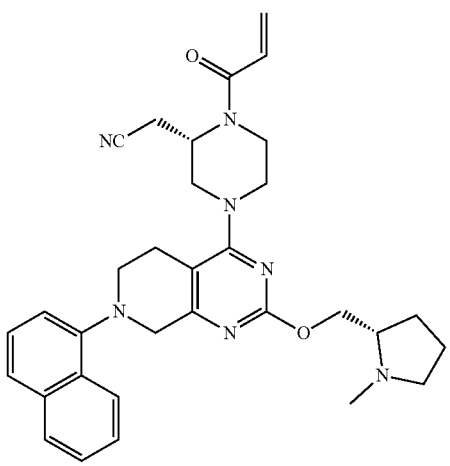 [SMILES: C=CC(=O)N1CCN(c2nc(OC[C@@H]3CCCN3C)nc3c2CCN(c2cccc4ccccc24)C3)C[C@@H]1CC#N]

or a pharmaceutically acceptable salt thereof, and a SOS1 inhibitor.

In one embodiment, the SOS1 inhibitor has the following structure:

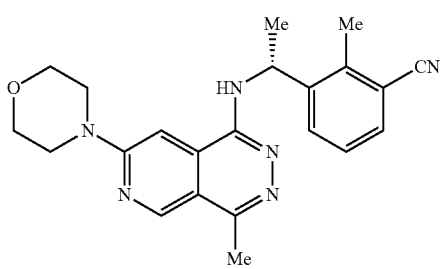 [SMILES: Cc1c(C#N)cccc1[C@@H](C)Nc1nnc(C)c2cnc(N3CCOCC3)cc12]

or a pharmaceutically acceptable salt thereof.

In yet another aspect, the method also comprises contacting the cell with a compound having the following structure:

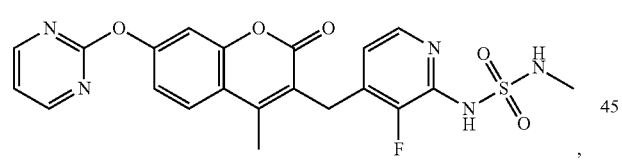

or a pharmaceutically acceptable salt thereof.

In yet another aspect, the invention provides for methods for increasing the sensitivity of a cancer cell to a KRas G12C inhibitor, comprising contacting the cancer cell with an effective amount of a combination of the KRas G12C inhibitor compound adagrasib or a pharmaceutically acceptable salt or a pharmaceutical composition thereof, and a SOS1 inhibitor, or a pharmaceutically acceptable salt or a pharmaceutical composition thereof, wherein the SOS1 inhibitor synergistically increases the sensitivity of the cancer cell to the KRas G12C inhibitor. In one embodiment, the contacting is in vitro. In one embodiment, the contacting is in vivo. In one embodiment, the method comprises administering to a subject undergoing KRas G12C treatment with an effective amount of a combination the KRas G12C inhibitor adagrasib or a pharmaceutically acceptable salt thereof, and a SOS1 inhibitor, wherein the SOS1 inhibitor synergistically increases the sensitivity of the cancer cell to the KRas G12C inhibitor.

In one embodiment, the method for increasing the sensitivity of a cancer cell to a KRas G12C inhibitor, comprises contacting the cancer cell with a therapeutically effective amount of a combination of the KRas G12C inhibitor compound adagrasib or a pharmaceutically acceptable salt or a pharmaceutical composition thereof, and a SOS1 inhibitor having the following structure:

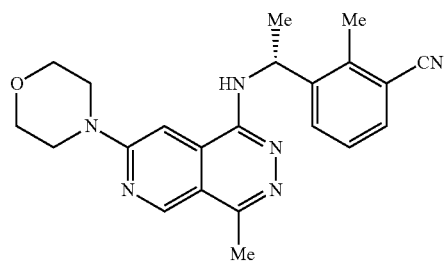 [SMILES: Cc1c(C#N)cccc1[C@@H](C)Nc1nnc(C)c2cnc(N3CCOCC3)cc12]

or a pharmaceutically acceptable salt thereof or a pharmaceutically acceptable salt or a pharmaceutical composition thereof.

In yet another embodiment, the method for increasing the sensitivity of a cancer cell to a KRas G12C inhibitor also comprises contacting the cancer cell with a compound having the following structure:

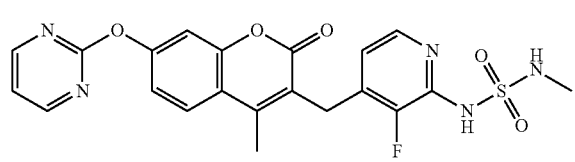

or a pharmaceutically acceptable salt thereof.

In one embodiment, the combination therapy comprises a combination of a compound having the formula:

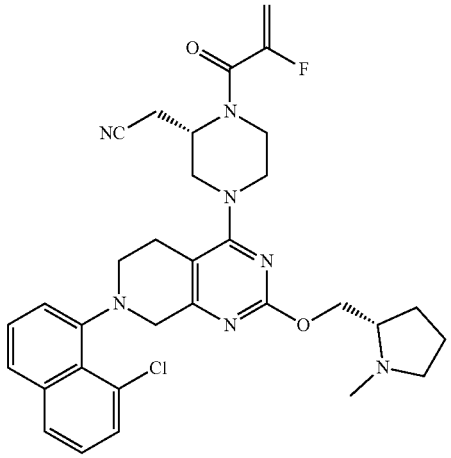 [SMILES: C=C(F)C(=O)N1CCN(c2nc(OC[C@@H]3CCCN3C)nc3c2CCN(c2cccc4cccc(Cl)c24)C3)C[C@@H]1CC#N]

(adagrasib) or a pharmaceutically acceptable salt thereof, and a SOS1 inhibitor.

In one such embodiment, the SOS1 inhibitor is:

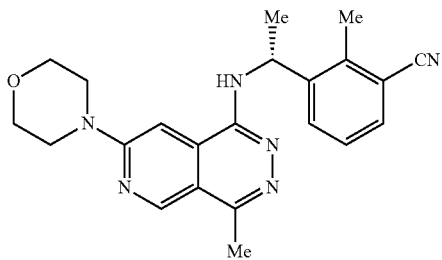 [SMILES: Cc1c(C#N)cccc1[C@@H](C)Nc1nnc(C)c2cnc(N3CCOCC3)cc12]

(R)-2-methyl-3-(1-((4-methyl-7-morpholinopyrido[3,4-d]pyridazin-1-yl)amino)ethyl)benzonitrile.

In another such embodiment, the SOS1 inhibitor is:

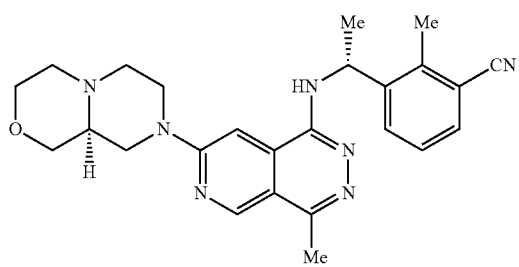 [SMILES: Cc1c(C#N)cccc1[C@@H](C)Nc1nnc(C)c2cnc(N3CCN4CCOC[C@@H]4C3)cc12]

3-((R)-1-((7-((S)-hexahydropyrazino[2,1-c][1,4]oxazin-8(1H)-yl)-4-methylpyrido[3,4-d]pyridazin-1-yl)amino)ethyl)-2-methylbenzonitrile.

In yet another such embodiment, the SOS1 inhibitor is:

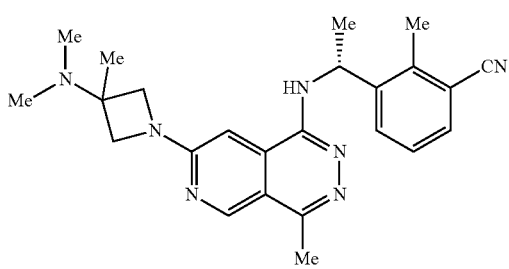 [SMILES: Cc1c(C#N)cccc1[C@@H](C)Nc1nnc(C)c2cnc(N3CC(C)(N(C)C)C3)cc12]

(R)-3-(1-((7-(3-(dimethylamino)-3-methylazetidin-1-yl)-4-methylpyrido[3,4-d]pyridazin-1-yl)amino)ethyl)-2-methylbenzonitrile.

In still another such embodiment, the SOS1 inhibitor is:

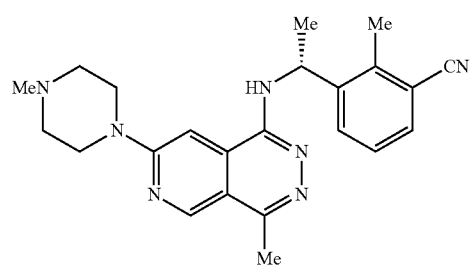 [SMILES: Cc1c(C#N)cccc1[C@@H](C)Nc1nnc(C)c2cnc(N3CCN(C)CC3)cc12]

(R)-2-methyl-3-(1-((4-methyl-7-(4-methylpiperazin-1-yl)pyrido[3,4-d]pyridazin-1-yl)amino)ethyl)benzonitrile.

In another embodiment, the SOS1 inhibitor is:

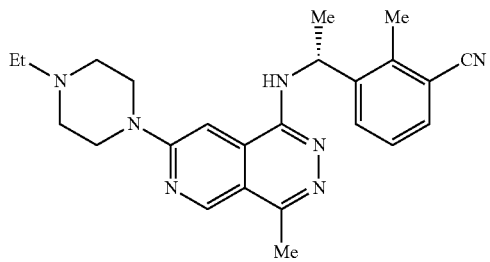 [SMILES: CCN1CCN(c2cc3c(N[C@H](C)c4cccc(C#N)c4C)nnc(C)c3cn2)CC1]

(R)-3-(1-((7-(4-ethylpiperazin-1-yl)-4-methylpyrido[3,4-d]pyridazin-1-yl)amino)ethyl)-2-methylbenzonitrile.

In another embodiment, the SOS1 inhibitor is:

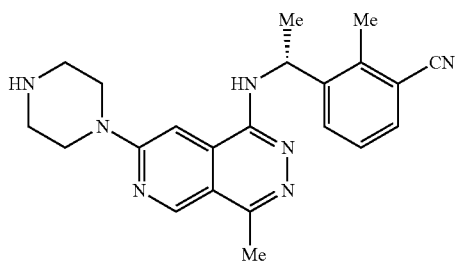 [SMILES: Cc1c(C#N)cccc1[C@@H](C)Nc1nnc(C)c2cnc(N3CCNCC3)cc12]

(R)-2-methyl-3-(1-((4-methyl-7-(piperazin-1-yl)pyrido[3,4-d]pyridazin-1-yl)amino)ethyl)benzonitrile.

In another embodiment, the SOS1 inhibitor is:

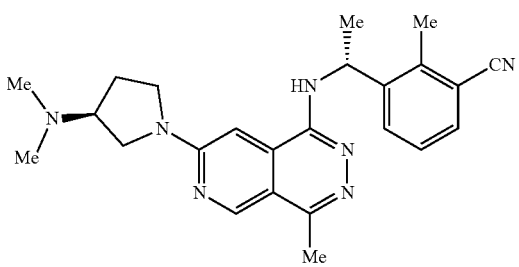 [SMILES: Cc1c(C#N)cccc1[C@@H](C)Nc1nnc(C)c2cnc(N3CC[C@H](N(C)C)C3)cc12]

3-((R)-1-((7-((S)-3-(dimethylamino)pyrrolidin-1-yl)-4-methylpyrido[3,4-d]pyridazin-1-yl)amino)ethyl)-2-methylbenzonitrile.

In another embodiment, the SOS1 inhibitor is:

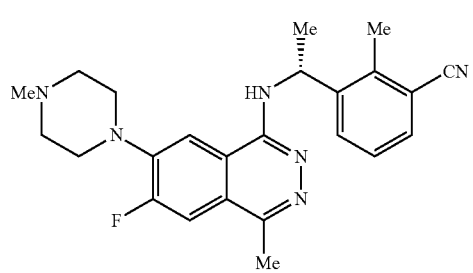 [SMILES: Cc1c(C#N)cccc1[C@@H](C)Nc1nnc(C)c2cc(F)c(N3CCN(C)CC3)cc12]

(R)-3-(1-((6-fluoro-4-methyl-7-(4-methylpiperazin-1-yl)phthalazin-1-yl)amino)ethyl)-2-methylbenzonitrile.

In still yet another embodiment, the SOS1 inhibitor is BI1701963.

In yet another embodiment, the invention provides a therapeutically effective combination of:
the SOS1 inhibitor (R)-2-methyl-3-(1-((4-methyl-7-morpholinopyrido[3,4-d]pyridazin-1-yl)amino)ethyl)benzonitrile (also known as MRTX0902), having the formula:

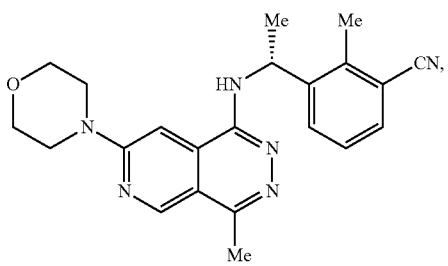 [SMILES: Cc1c(C#N)cccc1[C@@H](C)Nc1nnc(C)c2cnc(N3CCOCC3)cc12]

or a pharmaceutically acceptable salt thereof; and
a KRas G12C inhibitor compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (also known as MRTX849, and also known as adagrasib).

In another embodiment, the invention provides a therapeutically effective combination of:
the SOS1 inhibitor (R)-2-methyl-3-(1-((4-methyl-7-morpholinopyrido[3,4-d]pyridazin-1-yl)amino)ethyl)benzonitrile (also known as MRTX0902), having the formula:

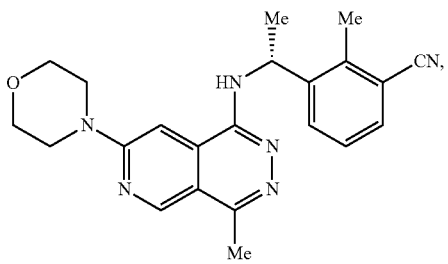 [SMILES: Cc1c(C#N)cccc1[C@@H](C)Nc1nnc(C)c2cnc(N3CCOCC3)cc12]

or a pharmaceutically acceptable salt thereof;
a KRas G12C inhibitor compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (also known as MRTX849, and also known as adagrasib); and
the MEK inhibitor [[3-fluoro-2-(methylsulfamoylamino)pyridin-4-yl]methyl]-4-methyl-7-pyrimidin-2-yloxychromen-2-one (also known as VS-6766) which has the following structure:

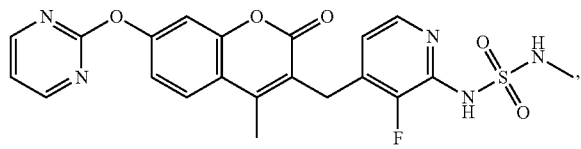 [SMILES: CNS(=O)(=O)Nc1nccc(Cc2c(C)c3ccc(Oc4ncccn4)cc3oc2=O)c1F]

or a pharmaceutically acceptable salt thereof.

As used herein, the term "contacting" refers to the bringing together of indicated moieties in an in vitro system or an in vivo system. For example, "contacting" a cancer cell includes the administration of a combination provided herein to an individual or subject, such as a human, having KRas G12C, as well as, for example, introducing a combination provided herein into a sample containing a cellular or purified preparation containing KRas G12C.

By negatively modulating the activity of KRas G12C, the methods described herein are designed to inhibit undesired cellular proliferation resulting from enhanced KRas G12C activity within the cell. The degree of covalent modification of KRas G12C may be monitored in vitro using well known methods, including those described in published international PCT application numbers WO2017201161 and WO2019099524. In addition, the inhibitory activity of combination in cells may be monitored, for example, by measuring the inhibition of KRas G12C activity of the amount of phosphorylated ERK to assess the effectiveness of treatment and dosages may be adjusted accordingly by the attending medical practitioner.

The compositions and methods provided herein may be used for the treatment of a KRas G12C-associated cancer in a subject in need thereof, comprising administering to said subject a therapeutically effective amount of a combination of a SOS1 inhibitor, or a pharmaceutically acceptable salt or a pharmaceutical composition thereof, and the KRas G12C inhibitor compound adagrasib or a pharmaceutically acceptable salt or a pharmaceutical composition thereof, wherein the SOS1 inhibitor synergistically increases the sensitivity of the KRas G12C-associated cancer to the KRas G12C inhibitor. In one embodiment, the KRas G12C-associated cancer is lung cancer.

In one embodiment, the therapeutically effective amount of the combination of a SOS1 inhibitor, or a pharmaceutically acceptable salt or a pharmaceutical composition thereof, and the KRas G12C inhibitor compound adagrasib or a pharmaceutically acceptable salt or a pharmaceutical composition thereof, results in an increased duration of overall survival ("OS") in subjects relative to treatment with only the KRas G12C inhibitor. In one embodiment, the therapeutically effective amount of the combination of a SOS1 inhibitor, or a pharmaceutically acceptable salt or a pharmaceutical composition thereof, and the KRas G12C inhibitor compound adagrasib or a pharmaceutically acceptable salt or a pharmaceutical composition thereof, results in an increased duration of progression-free survival ("PFS") in subjects relative to treatment with only the KRas G12C inhibitor. In one embodiment, the therapeutically effective amount of the combination of a SOS1 inhibitor, or a pharmaceutically acceptable salt or a pharmaceutical composition thereof, and the KRas G12C inhibitor compound adagrasib or a pharmaceutically acceptable salt or a pharmaceutical composition thereof, results in increased tumor regression in subjects relative to treatment with only the KRas G12C inhibitor. In one embodiment, the therapeutically effective amount of the combination of a SOS1 inhibitor, or a pharmaceutically acceptable salt or a pharmaceutical composition thereof, and the KRas G12C inhibitor compound adagrasib or a pharmaceutically acceptable salt or a pharmaceutical composition thereof, results in increased tumor growth inhibition in subjects relative to treatment with only the KRas G12C inhibitor. In one embodiment, the therapeutically effective amount of the combination of a SOS1 inhibitor, or a pharmaceutically acceptable salt or a pharmaceutical composition thereof, and the KRas G12C inhibitor compound adagrasib or a pharmaceutically acceptable salt or a pharmaceutical composition thereof, results in an improvement in the duration of stable disease in subjects compared to treatment with only the KRas G12C inhibitor adagrasib. In one embodiment, the SOS1 inhibitor is selected from (R)-2-methyl-3-(1-((4-methyl-7-morpholinopyrido[3,4-d]pyridazin-1-yl)amino)ethyl)benzonitrile, 3-((R)-1-((7-((S)-hexahydropyrazino[2,1-c][1,4]oxazin-8(1H)-yl)-4-methylpyrido[3,4-d]pyridazin-1-yl)amino)ethyl)-2-methylbenzonitrile, (R)-3-(1-((7-(3-(dimethylamino)-3-methylazetidin-1-yl)-4-methylpyrido[3,4-d]pyridazin-1-yl)amino)ethyl)-2-methylbenzonitrile, (R)-2-methyl-3-(1-((4-methyl-7-(4-methylpiperazin-1-yl)pyrido[3,4-d]pyridazin-1-yl)amino)ethyl)benzonitrile, (R)-3-(1-((7-(4-ethylpiperazin-1-yl)-4-methylpyrido[3,4-d]pyridazin-1-yl)amino)ethyl)-2-methylbenzonitrile, (R)-2-methyl-3-(1-((4-methyl-7-(piperazin-1-yl)pyrido[3,4-d]pyridazin-1-yl)amino)ethyl)benzonitrile, 3-((R)-1-((7-((S)-3-(dimethylamino)pyrrolidin-1-yl)-4-methylpyrido[3,4-d]pyridazin-1-yl)amino)ethyl)-2-methylbenzonitrile, (R)-3-(1-((6-fluoro-4-methyl-7-(4-methylpiperazin-1-yl)phthalazin-1-yl)amino)ethyl)-2-methylbenzonitrile, or a pharmaceutically acceptable salt thereof. In another embodiment, the SOS1 inhibitor is BI1701963.

In another embodiment, the SOS1 inhibitor, or a pharmaceutically acceptable salt or a pharmaceutical composition thereof, is administered in combination with the KRas G12C inhibitor, or a pharmaceutically acceptable salt or a pharmaceutical composition thereof, once disease progression has been observed for KRas G12C monotherapy, in which the combination therapy results in enhanced clinical benefit for the patient by increasing OS, PFS, tumor regression, tumor growth inhibition or the duration of stable disease in the patient. In one embodiment, the KRas G12C inhibitor is a compound selected from compound Nos. 1-678 (as numbered in WO2019099524), or a pharmaceutically acceptable salt thereof (e.g., Example No. 234, 359, 478 or 507 or a pharmaceutically acceptable salt thereof).

In one embodiment, the SOS1 inhibitor is selected from (R)-2-methyl-3-(1-((4-methyl-7-morpholinopyrido[3,4-d]pyridazin-1-yl)amino)ethyl)benzonitrile, 3-((R)-1-((7-((S)-hexahydropyrazino[2,1-c][1,4]oxazin-8(1H)-yl)-4-methylpyrido[3,4-d]pyridazin-1-yl)amino)ethyl)-2-methylbenzonitrile, (R)-3-(1-((7-(3-(dimethylamino)-3-methylazetidin-1-yl)-4-methylpyrido[3,4-d]pyridazin-1-yl)amino)ethyl)-2-methylbenzonitrile, (R)-2-methyl-3-(1-((4-methyl-7-(4-methylpiperazin-1-yl)pyrido[3,4-d]pyridazin-1-yl)amino)ethyl)benzonitrile, (R)-3-(1-((7-(4-ethylpiperazin-1-yl)-4-methylpyrido[3,4-d]pyridazin-1-yl)amino)ethyl)-2-methylbenzonitrile, (R)-2-methyl-3-(1-((4-methyl-7-(piperazin-1-yl)pyrido[3,4-d]pyridazin-1-yl)amino)ethyl)benzonitrile, 3-((R)-1-((7-((S)-3-(dimethylamino)pyrrolidin-1-yl)-4-methylpyrido[3,4-d]pyridazin-1-yl)amino)ethyl)-2-methylbenzonitrile, (R)-3-(1-((6-fluoro-4-methyl-7-(4-methylpiperazin-1-yl)phthalazin-1-yl)amino)ethyl)-2-methylbenzonitrile, or a pharmaceutically acceptable salt thereof. In another embodiment, the SOS1 inhibitor is BI1701963.

In one embodiment, the therapeutic combination comprises therapeutically effective amounts of adagrasib and (R)-2-methyl-3-(1-((4-methyl-7-morpholinopyrido[3,4-d]pyridazin-1-yl)amino)ethyl)benzonitrile, or a pharmaceutically acceptable salt thereof.

In another embodiment, the therapeutic combination comprises therapeutically effective amounts of adagrasib and 3-((R)-1-((7-((S)-hexahydropyrazino[2,1-c][1,4]oxazin-8(1H)-yl)-4-methylpyrido[3,4-d]pyridazin-1-yl)amino)ethyl)-2-methylbenzonitrile, or a pharmaceutically acceptable salt thereof.

In another embodiment, the therapeutic combination comprises therapeutically effective amounts of adagrasib and (R)-3-(1-((7-(3-(dimethylamino)-3-methylazetidin-1-yl)-4-methylpyrido[3,4-d]pyridazin-1-yl)amino)ethyl)-2-methylbenzonitrile, or a pharmaceutically acceptable salt thereof.

In another embodiment, the therapeutic combination comprises therapeutically effective amounts of adagrasib and (R)-2-methyl-3-(1-((4-methyl-7-(4-methylpiperazin-1-yl)pyrido[3,4-d]pyridazin-1-yl)amino)ethyl)benzonitrile, or a pharmaceutically acceptable salt thereof.

In another embodiment, the therapeutic combination comprises therapeutically effective amounts of adagrasib and (R)-3-(1-((7-(4-ethylpiperazin-1-yl)-4-methylpyrido[3,4-d]pyridazin-1-yl)amino)ethyl)-2-methylbenzonitrile, or a pharmaceutically acceptable salt thereof.

In another embodiment, the therapeutic combination comprises therapeutically effective amounts of adagrasib and (R)-2-methyl-3-(1-((4-methyl-7-(piperazin-1-yl)pyrido[3,4-d]pyridazin-1-yl)amino)ethyl)benzonitrile, or a pharmaceutically acceptable salt thereof.

In another embodiment, the therapeutic combination comprises therapeutically effective amounts of adagrasib and 3-((R)-1-((7-((S)-3-(dimethylamino)pyrrolidin-1-yl)-4-methylpyrido[3,4-d]pyridazin-1-yl)amino)ethyl)-2-methylbenzonitrile, or a pharmaceutically acceptable salt thereof.

In another embodiment, the therapeutic combination comprises therapeutically effective amounts of adagrasib and (R)-3-(1-((6-fluoro-4-methyl-7-(4-methylpiperazin-1-yl)phthalazin-1-yl)amino)ethyl)-2-methylbenzonitrile, or a pharmaceutically acceptable salt thereof.

In another embodiment, the therapeutic combination comprises therapeutically effective amounts of adagrasib and the SOS1 inhibitor is BI1701963.

The compositions and methods provided herein may be used for the treatment of a wide variety of cancers including tumors such as lung, colorectal, pancreas, prostate, breast, brain, skin, cervical carcinomas, testicular carcinomas, etc. More particularly, cancers that may be treated by the compositions and methods of the invention include, but are not limited to, tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosathecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma. In certain embodiments, the cancer is non-small cell lung cancer.

Also provided herein is a method for treating cancer in a subject in need thereof, the method comprising (a) determining that cancer is associated with a KRas G12C mutation (e.g., a KRas G12C-associated cancer) (e.g., as determined using a regulatory agency-approved, e.g., FDA-approved, assay or kit); and (b) administering to the patient a therapeutically effective amount of a combination of a SOS1 inhibitor, or a pharmaceutically acceptable salt or a pharmaceutical composition thereof, and the KRas G12C inhibitor compound adagrasib or a pharmaceutically acceptable salt or a pharmaceutical composition thereof, wherein the SOS1 inhibitor synergistically increases the sensitivity of the KRas G12C-associated cancer to the KRas G12C inhibitor. In one embodiment, the KRas G12C inhibitor is a compound selected from compound Nos. 1-678 (as numbered in WO2019099524), or a pharmaceutically acceptable salt thereof (e.g., one of Example Nos. 234, 359, 478 or 507 or a pharmaceutically acceptable salt thereof). In one embodiment, the SOS1 inhibitor is selected from: (R)-2-methyl-3-(1-((4-methyl-7-morpholinopyrido[3,4-d]pyridazin-1-yl)amino)ethyl)benzonitrile, 3-((R)-1-((7-((S)-hexahydropyrazino[2,1-c][1,4]oxazin-8(1H)-yl)-4-methylpyrido[3,4-d]pyridazin-1-yl)amino)ethyl)-2-methylbenzonitrile, (R)-3-(1-((7-(3-(dimethylamino)-3-methylazetidin-1-yl)-4-methylpyrido[3,4-d]pyridazin-1-yl)amino)ethyl)-2-methylbenzonitrile, (R)-2-methyl-3-(1-((4-methyl-7-(4-methylpiperazin-1-yl)pyrido[3,4-d]pyridazin-1-yl)amino)ethyl)benzonitrile, (R)-3-(1-((7-(4-ethylpiperazin-1-yl)-4-methylpyrido[3,4-d]pyridazin-1-yl)amino)ethyl)-2-methylbenzonitrile, (R)-2-methyl-3-(1-((4-methyl-7-(piperazin-1-yl)pyrido[3,4-d]pyridazin-1-yl)amino)ethyl)benzonitrile, 3-((R)-1-((7-((S)-3-(dimethylamino)pyrrolidin-1-yl)-4-methylpyrido[3,4-d]pyridazin-1-yl)amino)ethyl)-2-methylbenzonitrile, (R)-3-(1-((6-fluoro-4-methyl-7-(4-methylpiperazin-1-yl)phthalazin-1-yl)amino)ethyl)-2-methylbenzonitrile, or a pharmaceutically acceptable salt thereof; or the SOS1 inhibitor is BI1701963.

In one embodiment, the therapeutic combination comprises therapeutically effective amounts of (R)-2-methyl-3-(1-((4-methyl-7-morpholinopyrido[3,4-d]pyridazin-1-yl)amino)ethyl)benzonitrile or a pharmaceutically acceptable salt thereof.

In a further embodiment, the therapeutic combination comprises therapeutically effective amounts of 3-((R)-1-((7-((S)-hexahydropyrazino[2,1-c][1,4]oxazin-8(1H)-yl)-4-methylpyrido[3,4-d]pyridazin-1-yl)amino)ethyl)-2-methylbenzonitrile or a pharmaceutically acceptable salt thereof.

In a further embodiment, the therapeutic combination comprises therapeutically effective amounts of (R)-3-(1-((7-(3-(dimethylamino)-3-methylazetidin-1-yl)-4-methylpyrido[3,4-d]pyridazin-1-yl)amino)ethyl)-2-methylbenzonitrile or a pharmaceutically acceptable salt thereof.

In a further embodiment, the therapeutic combination comprises therapeutically effective amounts of (R)-2-methyl-3-(1-((4-methyl-7-(4-methylpiperazin-1-yl)pyrido[3,4-d]pyridazin-1-yl)amino)ethyl)benzonitrile or a pharmaceutically acceptable salt thereof.

In a further embodiment, the therapeutic combination comprises therapeutically effective amounts of (R)-3-(1-((7-(4-ethylpiperazin-1-yl)-4-methylpyrido[3,4-d]pyridazin-1-yl)amino)ethyl)-2-methylbenzonitrile or a pharmaceutically acceptable salt thereof.

In a further embodiment, the therapeutic combination comprises therapeutically effective amounts of (R)-2-methyl-3-(1-((4-methyl-7-(piperazin-1-yl)pyrido[3,4-d]pyridazin-1-yl)amino)ethyl)benzonitrile or a pharmaceutically acceptable salt thereof.

In a further embodiment, the therapeutic combination comprises therapeutically effective amounts of 3-((R)-1-((7-((S)-3-(dimethylamino)pyrrolidin-1-yl)-4-methylpyrido[3,4-d]pyridazin-1-yl)amino)ethyl)-2-methylbenzonitrile or a pharmaceutically acceptable salt thereof.

In a further embodiment, the therapeutic combination comprises therapeutically effective amounts of (R)-3-(1-((6-fluoro-4-methyl-7-(4-methylpiperazin-1-yl)phthalazin-1-yl)amino)ethyl)-2-methylbenzonitrile or a pharmaceutically acceptable salt thereof.

In a further embodiment, the therapeutic combination comprises therapeutically effective amounts of BI1701963.

In one embodiment, the KRas G12C compound adagrasib is administered as a tablet or capsule during the period of time. In one embodiment, the tablet or capsule formulation of adagrasib comprises on or more of: about 10 mg, about 25 mg, about 50 mg, about 75 mg, about 100 mg, about 150 mg, about 200 mg, about 250 mg, about 300 mg, about 350 mg, about 400 mg, about 450 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg and about 2000 mg. In one embodiment, adagrasib is orally administered once a day (QD) on a daily basis during a period of time. In one embodiment adagrasib is orally administered twice a day (BID) on a daily basis during a period of time.

In one embodiment, the SOS1 compound is orally administered in the amount of about 20 mg to about 500 mg (e.g., about 20 mg to about 480 mg, about 20 mg to about 460 mg, about 20 mg to about 440 mg, about 20 mg to about 420 mg, about 20 mg to about 400 mg, about 20 mg to about 380 mg, about 20 mg to about 360 mg, about 20 mg to about 340 mg, about 20 mg to about 320 mg, about 20 mg to about 300 mg, about 20 mg to about 280 mg, about 20 mg to about 260 mg, about 20 mg to about 240 mg, about 20 mg to about 220 mg, about 20 mg to about 200 mg, about 20 mg to about 180 mg, about 20 mg to about 160 mg, about 20 mg to about 140 mg, about 20 mg to about 120 mg, about 20 mg to about 100 mg, about 20 mg to about 80 mg, about 20 mg to about 60 mg, about 20 mg to about 40 mg, about 40 mg to about 500 mg, about 40 mg to about 480 mg, about 40 mg to about 460 mg, about 40 mg to about 440 mg, about 40 mg to about 420 mg, about 40 mg to about 400 mg, about 40 mg to about 380 mg, about 40 mg to about 360 mg, about 40 mg to about 340 mg, about 40 mg to about 320 mg, about 40 mg to about 300 mg, about 40 mg to about 280 mg, about 40 mg to about 260 mg, about 40 mg to about 240 mg, about 40 mg to about 220 mg, about 40 mg to about 200 mg, about 40 mg to about 180 mg, about 40 mg to about 160 mg, about 40 mg to about 140 mg, about 40 mg to about 120 mg, about 40 mg to about 100 mg, about 40 mg to about 80 mg, about 40 mg to about 60 mg, about 60 mg to about 500 mg, about 60 mg to about 480 mg, about 60 mg to about 460 mg, about 60 mg to about 440 mg, about 60 mg to about 420 mg, about 60 mg to about 400 mg, about 60 mg to about 380 mg, about 60 mg to about 360 mg, about 60 mg to about 340 mg, about 60 mg to about 320 mg, about 60 mg to about 300 mg, about 60 mg to about 280 mg, about 60 mg to about 260 mg, about 60 mg to about 240 mg, about 60 mg to about 220 mg, about 60 mg to about 200 mg, about 60 mg to about 180 mg, about 60 mg to about 160 mg, about 60 mg to about 140 mg, about 60 mg to about 120 mg, about 60 mg to about 100 mg, about 60 mg to about 80 mg, about 80 mg to about 500 mg, about 80 mg to about 480 mg, about 80 mg to about 460 mg, about 80 mg to about 440 mg, about 80 mg to about 420 mg, about 80 mg to about 400 mg, about 80 mg to about 380 mg, about 80 mg to about 360 mg, about 80 mg to about 340 mg, about 80 mg to about 320 mg, about 80 mg to about 300 mg, about 80 mg to about 280 mg, about 80 mg to about 260 mg, about 80 mg to about 240 mg, about 80 mg to about 220 mg, about 80 mg to about 200 mg, about 80 mg to about 180 mg, about 80 mg to about 160 mg, about 80 mg to about 140 mg, about 80 mg to about 120 mg, about 80 mg to about 100 mg, about 100 mg to about 500 mg, about 100 mg to about 480 mg, about 100 mg to about 460 mg, about 100 mg to about 440 mg, about 100 mg to about 420 mg, about 100 mg to about 400 mg, about 100 mg to about 380 mg, about 100 mg to about 360 mg, about 100 mg to about 340 mg, about 100 mg to about 320 mg, about 100 mg to about 300 mg, about 100 mg to about 280 mg, about 100 mg to about 260 mg, about 100 mg to about 240 mg, about 100 mg to about 220 mg, about 100 mg to about 200 mg, about 100 mg to about 180 mg, about 100 mg to about 160 mg, about 100 mg to about 140 mg, about 100 mg to about 120 mg, about 120 mg to about 500 mg, about 120 mg to about 480 mg, about 120 mg to about 460 mg, about 120 mg to about 440 mg, about 120 mg to about 420 mg, about 120 mg to about 400 mg, about 120 mg to about 380 mg, about 120 mg to about 360 mg, about 120 mg to about 340 mg, about 120 mg to about 320 mg, about 120 mg to about 300 mg, about 120 mg to about 280 mg, about 120 mg to about 260 mg, about 120 mg to about 240 mg, about 120 mg to about 220 mg, about 120 mg to about 200 mg, about 120 mg to about 180 mg, about 120 mg to about 160 mg, about 120 mg to about 140 mg, about 140 mg to about 500 mg, about 140 mg to about 480 mg, about 140 mg to about 460 mg, about 140 mg to about 440 mg, about 140 mg to about 420 mg, about 140 mg to about 400 mg, about 140 mg to about 380 mg, about 140 mg to about 360 mg, about 140 mg to about 340 mg, about 140 mg to about 320 mg, about 140 mg to about 300 mg, about 140 mg to about 280 mg, about 140 mg to about 260 mg, about 140 mg to about 240 mg, about 140 mg to about 220 mg, about 140 mg to about 200 mg, about 140 mg to about 180 mg, about 140 mg to about 160 mg, about 160 mg to about 500 mg, about 160 mg to about 480 mg, about 160 mg to about 460 mg, about 160 mg to about 440 mg, about 160 mg to about 420 mg, about 160 mg to about 400 mg, about 160 mg to about 380 mg, about 160 mg to about 360 mg, about 160 mg to about 340 mg, about 160 mg to about 320 mg, about 160 mg to about 300 mg, about 160 mg to about 280 mg, about 160 mg to about 260 mg, about 160 mg to about 240 mg, about 160 mg to about 220 mg, about 160 mg to about 200 mg, about 160 mg to about 180 mg, about 180 mg to about 500 mg, about 180 mg to about 480 mg, about 180 mg to about 460 mg, about 180 mg to about 440 mg, about 180 mg to about 420 mg, about 180 mg to about 400 mg, about 180 mg to about 380 mg, about 180 mg to about 360 mg, about 180 mg to about 340 mg, about 180 mg to about 320 mg, about 180 mg to about 300 mg, about 180 mg to about 280 mg, about 180 mg to about 260 mg, about 180 mg to about 240 mg, about 180 mg to about 220 mg, about 180 mg to about 200 mg, about 200 mg to about 500 mg, about 200 mg to about 480 mg, about 200 mg to about 460 mg, about 200 mg to about 440 mg, about 200 mg to about 420 mg, about 200 mg to about 400 mg, about 200 mg to about 380 mg, about 200 mg to about 360 mg, about 200 mg to about 340 mg, about 200 mg to about 320 mg, about 200 mg to about 300 mg, about 200 mg to about 280 mg, about 200 mg to about 260 mg, about 200 mg to about 240 mg, about 200 mg to about 220 mg, about 220 mg to about 500 mg, about 220 mg to about 480 mg, about 220 mg to about 460 mg, about 220 mg to about 440 mg, about 220 mg to about 420 mg, about 220 mg to about 400 mg, about 220 mg to about 380 mg, about 220 mg to about 360 mg, about 220 mg to about 340 mg, about 220 mg to about 320 mg, about 220 mg to about 300 mg, about 220 mg to about 280 mg, about 220 mg to about 260 mg, about 220 mg to about 240 mg, about 240 mg to about 500 mg, about 240 mg to about 480 mg, about 240 mg to about 460 mg, about 240 mg to about 440 mg, about 240 mg to about 420 mg, about 240 mg to about 400 mg, about 240 mg to about 380 mg, about 240 mg to about 360 mg, about 240 mg to about 340 mg, about 240 mg to about 320 mg, about 240 mg to about 300 mg, about 240 mg to about 280 mg, about 240 mg to about 260 mg, about 260 mg to about 500 mg, about 260 mg to about 480 mg, about 260 mg to about 460 mg, about 260 mg to about 440 mg, about 260 mg to about 420 mg, about 260 mg to about 400 mg, about 260 mg to about 380 mg, about 260 mg to about 360 mg, about 260 mg to about 340 mg, about 260 mg to about 320 mg, about 260 mg to about 300 mg, about 260 mg to about 280 mg, about 280 mg to about 500 mg, about 280 mg to about 480 mg, about 280 mg to about 460 mg, about 280 mg to about 440 mg, about 280 mg to about 420 mg, about 280 mg to about 400 mg, about 280 mg to about 380 mg, about 280 mg to about 360 mg, about 280 mg to about 340 mg, about 280 mg to about 320 mg, about 280 mg to about 300 mg, about 300 mg to about 500 mg, about 300 mg to about 480 mg, about 300 mg to about 460 mg, about 300 mg to about 440 mg, about 300 mg to about 420 mg, about 300 mg to about 400 mg, about 300 mg to about 380 mg, about 300 mg to about 360 mg, about 300 mg to about 340 mg, about 300 mg to about 320 mg, about 320 mg to about 500 mg, about 320 mg to about 480 mg, about 320 mg to about 460 mg, about 320 mg to about 440 mg, about 320 mg to about 420 mg, about 320 mg to about 400 mg, about 320 mg to about 380 mg, about 320 mg to about 360 mg, about 320 mg to about 340 mg, about 340 mg to about 500 mg, about 340 mg to about 480 mg, about 340 mg to about 460 mg, about 340 mg to about 440 mg, about 340 mg to about 420 mg, about 340 mg to about 400 mg, about 340 mg to about 380 mg, about 340 mg to about 360 mg, about 360 mg to about 500 mg, about 360 mg to about 480 mg, about 360 mg to about 460 mg, about 360 mg to about 440 mg, about 360 mg to about 420 mg, about 360 mg to about 400 mg, about 360 mg to about 380 mg, about 380 mg to about 500 mg, about 380 mg to about 480 mg, about 380 mg to about 460 mg, about 380 mg to about 440 mg, about 380 mg to about 420 mg, about 380 mg to about 400 mg, about 400 mg to about 500 mg, about 400 mg to about 480 mg, about 400 mg to about 460 mg, about 400 mg to about 440 mg, about 400 mg to about 420 mg, about 420 mg to about 500 mg, about 420 mg to about 480 mg, about 420 mg to about 460 mg, about 420 mg to about 440 mg, about 440 mg to about 500 mg, about 440 mg to about 480 mg, about 440 mg to about 460 mg, about 460 mg to about 500 mg, about 460 mg to about 480 mg, about 480 mg to about 500 mg, about 25, about 50, about 75, about 100, about 150, about 200, about 250, about 300, about 350, about 400, about 450, or about 500 mg), is administered over a period of time. In one embodiment, the SOS1 compound is orally administered twice a day (BID) on a daily basis during a period of time. In one embodiment adagrasib is orally administered twice a day (BID) on a daily basis during a period of time.

In one embodiment, the combination therapy comprises oral administration of adagrasib once or twice a day on a daily basis (during a period of time), e.g., in an amount of about 10 mg to about 400 mg (e.g., about 10 mg to about 380 mg, about 10 mg to about 360 mg, about 10 mg to about 340 mg, about 10 mg to about 320 mg, about 10 mg to about 300 mg, about 10 mg to about 280 mg, about 10 mg to about 260 mg, about 10 mg to about 240 mg, about 10 mg to about 220 mg, about 10 mg to about 200 mg, about 10 mg to about 180 mg, about 10 mg to about 160 mg, about 10 mg to about 140 mg, about 10 mg to about 120 mg, about 10 mg to about 100 mg, about 10 mg to about 80 mg, about 10 mg to about 60 mg, about 10 mg to about 40 mg, about 10 mg to about 20 mg, about 20 mg to about 400 mg, about 20 mg to about 380 mg, about 20 mg to about 360 mg, about 20 mg to about 340 mg, about 20 mg to about 320 mg, about 20 mg to about 300 mg, about 20 mg to about 280 mg, about 20 mg to about 260 mg, about 20 mg to about 240 mg, about 20 mg to about 220 mg, about 20 mg to about 200 mg, about 20 mg to about 180 mg, about 20 mg to about 160 mg, about 20 mg to about 140 mg, about 20 mg to about 120 mg, about 20 mg to about 100 mg, about 20 mg to about 80 mg, about 20 mg to about 60 mg, about 20 mg to about 40 mg, about 40 mg to about 400 mg, about 40 mg to about 380 mg, about 40 mg to about 360 mg, about 40 mg to about 340 mg, about 40 mg to about 320 mg, about 40 mg to about 300 mg, about 40 mg to about 280 mg, about 40 mg to about 260 mg, about 40 mg to about 240 mg, about 40 mg to about 220 mg, about 40 mg to about 200 mg, about 40 mg to about 180 mg, about 40 mg to about 160 mg, about 40 mg to about 140 mg, about 40 mg to about 120 mg, about 40 mg to about 100 mg, about 40 mg to about 80 mg, about 40 mg to about 60 mg, about 60 mg to about 400 mg, about 60 mg to about 380 mg, about 60 mg to about 360 mg, about 60 mg to about 340 mg, about 60 mg to about 320 mg, about 60 mg to about 300 mg, about 60 mg to about 280 mg, about 60 mg to about 260 mg, about 60 mg to about 240 mg, about 60 mg to about 220 mg, about 60 mg to about 200 mg, about 60 mg to about 180 mg, about 60 mg to about 160 mg, about 60 mg to about 140 mg, about 60 mg to about 120 mg, about 60 mg to about 100 mg, about 60 mg to about 80 mg, about 80 mg to about 400 mg, about 80 mg to about 380 mg, about 80 mg to about 360 mg, about 80 mg to about 340 mg, about 80 mg to about 320 mg, about 80 mg to about 300 mg, about 80 mg to about 280 mg, about 80 mg to about 260 mg, about 80 mg to about 240 mg, about 80 mg to about 220 mg, about 80 mg to about 200 mg, about 80 mg to about 180 mg, about 80 mg to about 160 mg, about 80 mg to about 140 mg, about 80 mg to about 120 mg, about 80 mg to about 100 mg, about 100 mg to about 400 mg, about 100 mg to about 380 mg, about 100 mg to about 360 mg, about 100 mg to about 340 mg, about 100 mg to about 320 mg, about 100 mg to about 300 mg, about 100 mg to about 280 mg, about 100 mg to about 260 mg, about 100 mg to about 240 mg, about 100 mg to about 220 mg, about 100 mg to about 200 mg, about 100 mg to about 180 mg, about 100 mg to about 160 mg, about 100 mg to about 140 mg, about 100 mg to about 120 mg, about 120 mg to about 400 mg, about 120 mg to about 380 mg, about 120 mg to about 360 mg, about 120 mg to about 340 mg, about 120 mg to about 320 mg, about 120 mg to about 300 mg, about 120 mg to about 280 mg, about 120 mg to about 260 mg, about 120 mg to about 240 mg, about 120 mg to about 220 mg, about 120 mg to about 200 mg, about 120 mg to about 180 mg, about 120 mg to about 160 mg, about 120 mg to about 140 mg, about 140 mg to about 400 mg, about 140 mg to about 380 mg, about 140 mg to about 360 mg, about 140 mg to about 340 mg, about 140 mg to about 320 mg, about 140 mg to about 300 mg, about 140 mg to about 280 mg, about 140 mg to about 260 mg, about 140 mg to about 240 mg, about 140 mg to about 220 mg, about 140 mg to about 200 mg, about 140 mg to about 180 mg, about 140 mg to about 160 mg, about 160 mg to about 400 mg, about 160 mg to about 380 mg, about 160 mg to about 360 mg, about 160 mg to about 360 mg, about 160 mg to about 340 mg, about 160 mg to about 320 mg, about 160 mg to about 300 mg, about 160 mg to about 280 mg, about 160 mg to about 260 mg, about 160 mg to about 240 mg, about 160 mg to about 220 mg, about 160 mg to about 200 mg, about 160 mg to about 180 mg, about 180 mg to about 400 mg, about 180 mg to about 380 mg, about 180 mg to about 360 mg, about 180 mg to about 340 mg, about 180 mg to about 320 mg, about 180 mg to about 300 mg, about 180 mg to about 280 mg, about 180 mg to about 260 mg, about 180 mg to about 240 mg, about 180 mg to about 220 mg, about 180 mg to about 200 mg, about 200 mg to about 400 mg, about 200 mg to about 380 mg, about 200 mg to about 360 mg, about 200 mg to about 340 mg, about 200 mg to about 320 mg, about 200 mg to about 300 mg, about 200 mg to about 280 mg, about 200 mg to about 260 mg, about 200 mg to about 240 mg, about 200 mg to about 220 mg, about 220 mg to about 400 mg, about 220 mg to about 380 mg, about 220 mg to about 360 mg, about 220 mg to about 340 mg, about 220 mg to about 320 mg, about 220 mg to about 300 mg, about 220 mg to about 280 mg, about 220 mg to about 260 mg, about 220 mg to about 240 mg, about 240 mg to about 400 mg, about 240 mg to about 380 mg, about 240 mg to about 360 mg, about 240 mg to about 340 mg, about 240 mg to about 320 mg, about 240 mg to about 300 mg, about 240 mg to about 280 mg, about 240 mg to about 260 mg, about 260 mg to about 400 mg, about 260 mg to about 380 mg, about 260 mg to about 360 mg, about 260 mg to about 340 mg, about 260 mg to about 320 mg, about 260 mg to about 300 mg, about 260 mg to about 280 mg, about 280 mg to about 400 mg, about 280 mg to about 380 mg, about 280 mg to about 360 mg, about 280 mg to about 340 mg, about 280 mg to about 320 mg, about 280 mg to about 300 mg, about 300 mg to about 400 mg, about 300 mg to about 380 mg, about 300 mg to about 360 mg, about 300 mg to about 340 mg, about 300 mg to about 320 mg, about 320 mg to about 400 mg, about 320 mg to about 380 mg, about 320 mg to about 360 mg, about 340 mg to about 360 mg, about 340 mg to about 400 mg, about 340 mg to about 380 mg, about 340 mg to about 360 mg, about 360 mg to about 400 mg, about 360 mg to about 380 mg, about 380 mg to about 400 mg, about 100 mg, about 200 mg, about 300 mg, or about 400 mg), and oral administration of a SOS1 inhibitor, or a pharmaceutically acceptable salt or a pharmaceutical composition thereof which is administered, for example once a day on a daily basis (during a period of time). In one embodiment, the KRas G12C inhibitor adagrasib or a pharmaceutically acceptable salt or a pharmaceutical composition thereof is orally administered once daily. In another embodiment, the KRas G12C inhibitor, or a pharmaceutically acceptable salt or a pharmaceutical composition thereof, is orally administered twice daily.

One skilled in the art will recognize that, both in vivo and in vitro trials using suitable, known and generally accepted cell and/or animal models are predictive of the ability of a test compound of the combination or the combination to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

Synergy

In one embodiment, the addition of a SOS1 inhibitor, or a pharmaceutically acceptable salt or a pharmaceutical composition thereof, synergistically increases the activity of the KRas G12C inhibitor compound adagrasib or a pharmaceutically acceptable salt or a pharmaceutical composition thereof against cancer or cancer cell lines expressing KRas G12C. Any method for determining whether two compounds exhibit synergy may be used for determining the synergistic effect of the combination.

Several mathematical models have been developed to determine whether two compounds act synergistically, i.e., beyond a mere additive effect. For instance, Loewe Additivity (Loewe (1928) Physiol. 27: 47-187), Bliss Independence (Bliss (1939) Ann. Appl. Biol. 26: 585-615), Highest Single Agent, ZIP (Yadav et al (2015) Comput Struct Biotech J 13: 504-513) and other models (Chou & Talalay (1984) Adv Enzyme Regul 22: 27-55. #6382953; and Greco et al. (1995) Pharmacol Rev 47(2): 331-85. #7568331) are well known models in the pharmaceutical industry and may be used to calculate a "synergy score" that indicates whether synergy was detected and the magnitude of such synergy. Combining these synergy scores produces a composite synergy score which may be used to evaluate and characterize the KRas G12C inhibitor compound adagrasib-B in combination with a SOS1 inhibitor.

In general, the mathematical models use data obtained from single agent values to determine the predicted additive effect of the combination which is compared to the observed effect for the combination. If the observed effect is greater than the predicted effect, the combination is deemed to be synergistic. For example, the Bliss independence model compares the observed combination response ($Y_O$) with the predicted combination response ($Y_P$), which was obtained based on the assumption that there is no effect from drug-drug interactions. Typically, the combination effect is declared synergistic if $Y_O$ is greater than $Y_P$.

In some embodiments, "synergistic effect" as used herein refers to combination of a KRasKRas inhibitor or a pharmaceutically acceptable salt thereof, and a SOS1SOS1 inhibitor or a pharmaceutically acceptable salt thereof producing an effect, for example, any of the beneficial or desired results including clinical results or endpoints as described herein, which is greater than the sum of the effect observed when a compound such as one described in compound Nos. 1-678 as numbered in WO2019099524, for instance adagrasib, and a SOS1 inhibitor or a pharmaceutically acceptable salt thereof are administered alone. In one embodiment, the KRas G12C inhibitor is adagrasib (MRTX-849, Example No. 478 in WO2019099524) or a pharmaceutically acceptable salt thereof). In one embodiment, the SOS1 inhibitor is selected from (R)-2-methyl-3-(1-((4-methyl-7-morpholinopyrido[3,4-d]pyridazin-1-yl)amino) ethyl)benzonitrile, 3-((R)-1-((7-((S)-hexahydropyrazino[2,1-c][1,4]oxazin-8(1H)-yl)-4-methylpyrido[3,4-d]pyridazin-1-yl)amino)ethyl)-2-methylbenzonitrile, (R)-3-(1-((7-(3-(dimethylamino)-3-methylazetidin-1-yl)-4-methylpyrido[3,4-d]pyridazin-1-yl)amino)ethyl)-2-methylbenzonitrile, (R)-2-methyl-3-(1-((4-methyl-7-(4-methylpiperazin-1-yl)pyrido[3,4-d]pyridazin-1-yl)amino)ethyl)benzonitrile, (R)-3-(1-((6-fluoro-4-methyl-7-(4-methylpiperazin-1-yl)phthalazin-1-yl)amino)ethyl)-2-methylbenzonitrile, or a pharmaceutically acceptable salt thereof, or a SOS1 inhibitor such as BI1701963.

In one embodiment, the synergistic therapeutic combination comprises therapeutically effective amounts of (R)-2-methyl-3-(1-((4-methyl-7-morpholinopyrido[3,4-d]pyridazin-1-yl)amino)ethyl)benzonitrile and adagrasib. In one embodiment, the synergistic therapeutic combination comprises therapeutically effective amounts of 3-((R)-1-((7-((S)-hexahydropyrazino[2,1-c][1,4]oxazin-8(1H)-yl)-4-methylpyrido[3,4-d]pyridazin-1-yl)amino)ethyl)-2-methylbenzonitrile and adagrasib. In one embodiment, the synergistic therapeutic combination comprises therapeutically effective amounts of (R)-3-(1-((7-(3-(dimethylamino)-3-methylazetidin-1-yl)-4-methylpyrido[3,4-d]pyridazin-1-yl)amino)ethyl)-2-methylbenzonitrile and adagrasib. In one embodiment, the synergistic therapeutic combination comprises therapeutically effective amounts of (R)-2-methyl-3-(1-((4-methyl-7-(4-methylpiperazin-1-yl)pyrido[3,4-d]pyridazin-1-yl)amino)ethyl)benzonitrile and adagrasib. In one embodiment, the synergistic therapeutic combination comprises therapeutically effective amounts of (R)-3-(1-((7-(4-ethylpiperazin-1-yl)-4-methylpyrido[3,4-d]pyridazin-1-yl)amino)ethyl)-2-methylbenzonitrile, and adagrasib. In one embodiment, the synergistic therapeutic combination comprises therapeutically effective amounts of (R)-2-methyl-3-(1-((4-methyl-7-(piperazin-1-yl)pyrido[3,4-d]pyridazin-1-yl)amino)ethyl)benzonitrile, and adagrasib. In one embodiment, the synergistic therapeutic combination comprises therapeutically effective amounts of 3-((R)-1-((7-((S)-3-(dimethylamino)pyrrolidin-1-yl)-4-methylpyrido[3,4-d]pyridazin-1-yl)amino)ethyl)-2-methylbenzonitrile, and adagrasib. In one embodiment, the synergistic therapeutic combination comprises therapeutically effective amounts of (R)-3-(1-((6-fluoro-4-methyl-7-(4-methylpiperazin-1-yl)phthalazin-1-yl)amino)ethyl)-2-methylbenzonitrile and adagrasib.

In one embodiment, the therapeutic combination comprises therapeutically effective amounts of BI1701963 and adagrasib.

In some embodiments, the methods provided herein can result in a 1% to 99/a (e.g., 1% to 98%, 1% to 95%, 1% to 90%, 1 to 85%, 1 to 80%, 1% to 75%, 1% to 70%, 1% to 65%, 1% to 60%, 1% to 55%, 1% to 50%, 1% to 45%, 1% to 40%, 1% to 35%, 1% to 30%, 1% to 25%, 1% to 20%, 1% to 15%, 1% to 10%, 1% to 5%, 2% to 99%, 2% to 90%, 2% to 85%, 2% to 80%, 2% to 75%, 2% to 70%, 2% to 65%, 2% to 60%, 2% to 55%, 2% to 50%, 2% to 45%, 2% to 40%, 2% to 35%, 2% to 30%, 2% to 25%, 2% to 20%, 2% to 15%, 2% to 10%, 2% to 5%, 4% to 99%, 4% to 95%, 4% to 90%, 4% to 85%, 4% to 80%, 4% to 75%, 4% to 70%, 4% to 65%, 4% to 60%, 4% to 55%, 4% to 50%, 4% to 45%, 4% to 40%, 4% to 35%, 4% to 30%, 4% to 25%, 4% to 20%, 4% to 15%, 4% to 10%, 6% to 99%, 6% to 95%, 6% to 90%, 6% to 85%, 6% to 80%, 6% to 75%, 6% to 70%, 6% to 65%, 6% to 60%, 6% to 55%, 6% to 50%, 6% to 45%, 6% to 40%, 6% to 35%, 6% to 30%, 6% to 25%, 6% to 20%, 6% to 15%, 6% to 10%, 8% to 99%, 8% to 95%, 8% to 90%, 8% to 85%, 8% to 80%, 8% to 75%, 8% to 70%, 8% to 65%, 8% to 60%, 8% to 55%, 8% to 50%, 8% to 45%, 8% to 40%, 8% to 35%, 8% to 30%, 8% to 25%, 8% to 20%, 8% to 15%, 10% to 99%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, 10% to 40%, 10% to 35%, 10% to 30%, 10% to 25%, 10% to 20%, 10% to 15%, 15% to 99%, 15% to 95%, 15% to 90%, 15% to 85%, 15% to 80%, 15% to 75%, 15% to 70%, 15% to 65%, 15% to 60%, 15% to 55%, 15% to 50%, 15% to 55%, 15% to 50%, 15% to 45%, 15% to 40%, 15% to 35%, 15% to 30%, 15% to 25%, 15% to 20%, 20% to 99%, 20% to 95%, 20% to 90%, 20% to 85%, 20% to 80%, 20% to 75%, 20% to 70%, 20% to 65%, 20% to 60%, 20% to 55%, 20% to 50%, 20% to 45%, 20% to 40%, 20% to 35%, 20% to 30%, 20% to 25%, 25% to 99%, 25% to 95%, 25% to 90%, 25% to 85%, 25% to 80%, 25% to 75%, 25% to 70%, 25% to 65%, 25% to 60%, 25% to 55%, 25% to 50%, 25% to 45%, 25% to 40%, 25% to 35%, 25% to 30%, 30% to 99%, 30% to 95%, 30% to 90%, 30% to 85%, 30% to 80%, 30% to 75%, 30% to 70%, 30% to 65%, 30% to 60%, 30% to 55%, 30% to 50%, 30% to 45%, 30% to 40%, 30% to 35%, 35% to 99%, 35% to 95%, 35% to 90%, 35% to 85%, 35% to 80%, 35% to 75%, 35% to 70%, 35% to 65%, 35% to 60%, 35% to 55%, 35% to 50%, 35% to 45%, 35% to 40%, 40% to 99%, 40% to 95%, 40% to 90%, 40% to 85%, 40% to 80%, 40% to 75%, 40% to 70%, 40% to 65%, 40% to 60%, 40% to 55%, 40% to 60%, 40% to 55%, 40% to 50%, 40% to 45%, 45% to 99%, 45% to 95%, 45% to 95%, 45% to 90%, 45% to 85%, 45% to 80%, 45% to 75%, 45% to 70%, 45% to 65%, 45% to 60%, 45% to 55%, 45% to 50%, 50% to 99%, 50% to 95%, 50% to 90%, 50% to 85%, 50% to 80%, 50% to 75%, 50% to 70%, 50% to 65%, 50% to 60%, 50% to 55%, 55% to 99%, 55% to 95%, 55% to 90%, 55% to 85%, 55% to 80%, 55% to 75%, 55% to 70%, 55% to 65%, 55% to 60%, 60% to 99%, 60% to 95%, 60% to 90%, 60% to 85%, 60% to 80%, 60% to 75%, 60% to 70%, 60% to 65%, 65% to 99%, 60% to 95%, 60% to 90%, 60% to 85%, 60% to 80%, 60% to 75%, 60% to 70%, 60% to 65%, 70% to 99%, 70% to 95%, 70% to 90%, 70% to 85%, 70% to 80%, 70% to 75%, 75% to 99%, 75% to 95%, 75% to 90%, 75% to 85%, 75% to 80%, 80% to 99%, 80% to 95%, 80% to 90%, 80% to 85%, 85% to 99%, 85% to 95%, 85% to 90%, 90% to 99%, 90% to 95%, or 95% to 100%) reduction in the volume of one or more solid tumors in a patient following treatment with the combination therapy for a period of time between 1 day and 2 years (e.g., between 1 day and 22 months, between 1 day and 20 months, between 1 day and 18 months, between 1 day and 16 months, between 1 day and 14 months, between 1 day and 12 months, between 1 day and 10 months, between 1 day and 9 months, between 1 day and 8 months, between 1 day and 7 months, between 1 day and 6 months, between 1 day and 5 months, between 1 day and 4 months, between 1 day and 3 months, between 1 day and 2 months, between 1 day and 1 month, between one week and 2 years, between 1 week and 22 months, between 1 week and 20 months, between 1 week and 18 months, between 1 week and 16 months, between 1 week and 14 months, between 1 week and 12 months, between 1 week and 10 months, between 1 week and 9 months, between 1 week and 8 months, between 1 week and 7 months, between 1 week and 6 months, between 1 week and 5 months, between 1 week and 4 months, between 1 week and 3 months, between 1 week and 2 months, between 1 week and 1 month, between 2 weeks and 2 years, between 2 weeks and 22 months, between 2 weeks and 20 months, between 2 weeks and 18 months, between 2 weeks and 16 months, between 2 weeks and 14 months, between 2 weeks and 12 months, between 2 weeks and 10 months, between 2 weeks and 9 months, between 2 weeks and 8 months, between 2 weeks and 7 months, between 2 weeks and 6 months, between 2 weeks and 5 months, between 2 weeks and 4 months, between 2 weeks and 3 months, between 2 weeks and 2 months, between 2 weeks and 1 month, between 1 month and 2 years, between 1 month and 22 months, between 1 month and 20 months, between 1 month and 18 months, between 1 month and 16 months, between 1 month and 14 months, between 1 month and 12 months, between 1 month and 10 months, between 1 month and 9 months, between 1 month and 8 months, between 1 month and 7 months, between 1 month and 6 months, between 1 month and 6 months, between 1 month and 5 months, between 1 month and 4 months, between 1 month and 3 months, between 1 month and 2 months, between 2 months and 2 years, between 2 months and 22 months, between 2 months and 20 months, between 2 months and 18 months, between 2 months and 16 months, between 2 months and 14 months, between 2 months and 12 months, between 2 months and 10 months, between 2 months and 9 months, between 2 months and 8 months, between 2 months and 7 months, between 2 months and 6 months, or between 2 months and 5 months, between 2 months and 4 months, between 3 months and 2 years, between 3 months and 22 months, between 3 months and 20 months, between 3 months and 18 months, between 3 months and 16 months, between 3 months and 14 months, between 3 months and 12 months, between 3 months and 10 months, between 3 months and 8 months, between 3 months and 6 months, between 4 months and 2 years, between 4 months and 22 months, between 4 months and 20 months, between 4 months and 18 months, between 4 months and 16 months, between 4 months and 14 months, between 4 months and 12 months, between 4 months and 10 months, between 4 months and 8 months, between 4 months and 6 months, between 6 months and 2 years, between 6 months and 22 months, between 6 months and 20 months, between 6 months and 18 months, between 6 months and 16 months, between 6 months and 14 months, between 6 months and 12 months, between 6 months and 10 months, or between 6 months and 8 months) (e.g., as compared to the size of the one or more solid tumors in the patient prior to treatment).

The phrase "time of survival" means the length of time between the identification or diagnosis of cancer (e.g., any of the cancers described herein) in a mammal by a medical professional and the time of death of the mammal (caused by the cancer). Methods of increasing the time of survival in a mammal having a cancer are described herein.

In some embodiments, any of the methods described herein can result in an increase (e.g., a 1% to 400%, 1% to 380%, 1% to 360%, 1% to 340%, 1% to 320%, 1% to 300%, 1% to 280%, 1% to 260%, 1% to 240%, 1% to 220%, 1% to 200%, 1% to 180%, 1% to 160%, 1% to 140%, 1% to 120%, 1% to 100%, 1% to 95%, 1% to 90%, 1% to 85%, 1% to 80%, 1% to 75%, 1% to 70%, 1% to 65%, 1% to 60%, 1% to 55%, 1% to 50%, 1% to 45%, 1% to 40%, 1% to 35%, 1% to 30%, 1% to 25%, 1% to 20%, 1% to 15%, 1% to 10%, 1% to 5%, 5% to 400%, 5% to 380%, 5% to 360%, 5% to 340%, 5% to 320%, 5% to 300%, 5% to 280%, 5% to 260%, 5% to 240%, 5% to 220%, 5% to 200%, 5% to 180%, 5% to 160%, 5% to 140%, 5% to 120%, 5% to 100%, 5% to 90%, 5% to 80%, 5% to 70%, 5% to 60%, 5% to 50%, 5% to 40%, 5% to 30%, 5% to 20%, 5% to 10%, 10% to 400%, 10% to 380%, 10% to 360%, 10% to 340%, 10% to 320%, 10% to 300%, 10% to 280%, 10% to 260%, 10% to 240%, 10% to 220%, 10% to 200%, 10% to 180%, 10% to 160%, 10% to 140%, 10% to 120%, 10% to 100%, 10% to 90%, 10% to 80%, 10% to 70%, 10% to 60%, 10% to 50%, 10% to 40%, 10% to 30%, 10% to 20%, 20% to 400%, 20% to 380%, 20% to 360%, 20% to 340%, 20% to 320%, 20% to 300%, 20% to 280%, 20% to 260%, 20% to 240%, 20% to 220%, 20% to 200%, 20% to 180%, 20% to 160%, 20% to 140%, 20% to 120%, 20% to 100%, 20% to 90%, 20% to 80%, 20% to 70%, 20% to 60%, 20% to 50%, 20% to 40%, 20% to 30%, 30% to 400%, 30% to 380%, 30% to 360%, 30% to 340%, 30% to 320%, 30% to 300%, 30% to 280%, 30% to 260%, 30% to 240%, 30% to 220%, 30% to 200%, 30% to 180%, 30% to 160%, 30% to 140%, 30% to 120%, 30% to 100%, 30% to 90%, 30% to 80%, 30% to 70%, 30% to 60%, 30% to 50%, 30% to 40%, 40% to 400%, 40% to 380%, 40% to 360%, 40% to 340%, 40% to 320%, 40% to 300%, 40% to 280%, 40% to 260%, 40% to 240%, 40% to 220%, 40% to 200%, 40% to 180%, 40% to 160%, 40% to 140%, 40% to 120%, 40% to 100%, 40% to 90%, 40% to 80%, 40% to 70%, 40% to 60%, 40% to 50%, 50% to 400%, 50% to 380%, 50% to 360%, 50% to 340%, 50% to 320%, 50% to 300%, 50% to 280%, 50% to 260%, 50% to 240%, 50% to 220%, 50% to 200%, 50% to 180%, 50% to 160%, 50% to 140%, 50% to 140%, 50% to 120%, 50% to 100%, 50% to 90%, 50% to 80%, 50% to 70%, 50% to 60%, 60% to 400%, 60% to 380%, 60% to 360%, 60% to 340%, 60% to 320%, 60% to 300%, 60% to 280%, 60% to 260%, 60% to 240%, 60% to 220%, 60% to 200%, 60% to 180%, 60% to 160%, 60% to 140%, 60% to 120%, 60% to 100%, 60% to 90%, 60% to 80%, 60% to 70%, 70% to 400%, 70% to 380%, 70% to 360%, 70% to 340%, 70% to 320%, 70% to 300%, 70% to 280%, 70% to 260%, 70% to 240%, 70% to 220%, 70% to 200%, 70% to 180%, 70% to 160%, 70% to 140%, 70% to 120%, to 100%, 70% to 90%, 70% to 80%, 80% to 400%, 80% to 380%, 80% to 360%, 80% to 340%, 80% to 320%, 80% to 300%, 80% to 280%, 80% to 260%, 80% to 240%, 80% to 220%, 80% to 200%, 80% to 180%, 80% to 160%, 80% to 140%, 80% to 120%, 80% to 100%, 80% to 90%, 90% to 400%, 90% to 380%, 90% to 360%, 90% to 340%, 90% to 320%, 90% to 300%, 90% to 280%, 90% to 260%, 90% to 240%, 90% to 220%, 90% to 200%, 90% to 180%, 90% to 160%, 90% to 140%, 90% to 120%, 90% to 100%, 100% to 400%, 100% to 380%, 100% to 360%, 100% to 340%, 100% to 320%, 100% to 300%, 100% to 280%, 100% to 260%, 100% to 240%, 100% to 220%, 100% to 200%, 100% to 180%, 100% to 160%, 100% to 140%, 100% to 120%, 120% to 400%, 120% to 380%, 120% to 360%, 120% to 340%, 120% to 320%, 120% to 300%, 120% to 280%, 120% to 260%, 120% to 240%, 120% to 220%, 120% to 200%, 120% to 180%, 120% to 160%, 120% to 140%, 140% to 400%, 140% to 380%, 140% to 360%, 140% to 340%, 140% to 320%, 140% to 300%, 140% to 280%, 140% to 260%, 140% to 240%, 140% to 220%, 140% to 200%, 140% to 180%, 140% to 160%, 160% to 400%, 160% to 380%, 160% to 360%, 160% to 340%, 160% to 320%, 160% to 300%, 160% to 280%, 160% to 260%, 160% to 240%, 160% to 220%, 160% to 200%, 160% to 180%, 180% to 400%, 180% to 380%, 180% to 360%, 180% to 340%, 180% to 320%, 180% to 300%, 180% to 280%, 180% to 260%, 180% to 240%, 180% to 220%, 180% to 200%, 200% to 400%, 200% to 380%, 200% to 360%, 200% to 340%, 200% to 320%, 200% to 300%, 200% to 280%, 200% to 260%, 200% to 240%, 200% to 220%, 220% to 400%, 220% to 380%, 220% to 360%, 220% to 340%, 220% to 320%, 220% to 300%, 220% to 280%, 220% to 260%, 220% to 240%, 240% to 400%, 240% to 380%, 240% to 360%, 240% to 340%, 240% to 320%, 240% to 300%, 240% to 280%, 240% to 260%, 260% to 400%, 260% to 380%, 260% to 360%, 260% to 340%, 260% to 320%, 260% to 300%, 260% to 280%, 280% to 400%, 280% to 380%, 280% to 360%, 280% to 340%, 280% to 320%, 280% to 300%, 300% to 400%, 300% to 380%, 300% to 360%, 300% to 340%, or 300% to 320%) in the time of survival of the patient (e.g., as compared to a patient having a similar cancer and administered a different treatment or not receiving a treatment).

In some embodiments of any of the methods described herein, before treatment with the compositions or methods of the invention, the patient was treated with one or more of a chemotherapy, a targeted anticancer agent, radiation therapy, and surgery, and optionally, the prior treatment was unsuccessful; and/or the patient has been administered surgery and optionally, the surgery was unsuccessful; and/or the patient has been treated with a platinum-based chemotherapeutic agent, and optionally, the patient has been previously determined to be non-responsive to treatment with the platinum-based chemotherapeutic agent; and/or the patient has been treated with a kinase inhibitor, and optionally, the prior treatment with the kinase inhibitor was unsuccessful; and/or the patient was treated with one or more other therapeutic agent(s).

Kits

The present invention also relates to a kit comprising a SOS1 inhibitor, or a pharmaceutically acceptable salt or a pharmaceutical composition thereof, and the KRas G12C inhibitor compound adagrasib or a pharmaceutically acceptable salt or a pharmaceutical composition thereof. Also provided is a kit comprising a SOS1 inhibitor, or a pharmaceutically acceptable salt or a pharmaceutical composition thereof, and the KRas G12C inhibitor compound adagrasib or a pharmaceutically acceptable salt or a pharmaceutical composition thereof, for use in treating a hematological cancer.

In a related aspect, the invention provides a kit containing a dose of a SOS1 inhibitor, or a pharmaceutically acceptable salt or a pharmaceutical composition thereof, and dose of the KRas G12C inhibitor compound adagrasib or a pharmaceutically acceptable salt or a pharmaceutical composition thereof, in an amount effective to inhibit proliferation of cancer cells, particularly KRas G12C-expressing cancer cells, in a subject. The kit in some cases includes an insert with instructions for administration of the a SOS1 inhibitor, or a pharmaceutically acceptable salt or a pharmaceutical composition thereof, and the KRas G12C inhibitor compound adagrasib or a pharmaceutically acceptable salt or a pharmaceutical composition thereof. The insert may provide a user with one set of instructions for using the a SOS1 inhibitor, or a pharmaceutically acceptable salt or a pharmaceutical composition thereof, in combination with the KRas G12C inhibitor compound adagrasib or a pharmaceutically acceptable salt or a pharmaceutical composition thereof.

The following Examples are intended to illustrate further certain embodiments of the invention and are not intended to limit the scope of the invention.

EXAMPLE A

In Vivo Models for Examining KRas G12C Inhibitor—SOS1 Inhibitor Combinations

Immunocompromised nude/nude mice are inoculated in the right hind flank with cells or patient derived tumor samples harboring a KRas G12C mutation. When tumor volumes reach between 200-400 mm$^3$ in size, the mice are divided into four groups of 4-12 mice each. The first group is administered vehicle only. The second group is administered a single agent dose of the KRas G12C inhibitor at a concentration that yields a maximal biological effect or a less than maximal biological effect, depending on the cell line and the single agent activity, that does not result in complete tumor regression. The third group is administered a single agent dose of the SOS1 inhibitor at a concentration that yields a maximal biological effect or a less than maximal biological effect, depending on the cell line and the single agent activity, that also does not result in complete tumor regression. An optional group is administered with a single agent dose of the MEK inhibitor (VS-6766) that yields less than maximal biological effect. The final group is administered the single agent dose of the KRas G12C inhibitor in combination with the single agent dose of the SOS1 inhibitor or with single agent dose of the KRas G12C inhibitor in combination with the single agent dose of the SOS1 inhibitor and the single agent VS-6766. The treatment period varies from cell line to cell line but typically is between 20-42 days. Tumor volumes are measured using a caliper every two-three days and tumor volumes are calculated by the formula: $0.5\times(Length\times Width)^2$. A greater degree of tumor growth inhibition for the combination in this model demonstrates that the combination therapy is likely to have a clinically meaningful benefit to treated subjects relative to treatment with only a KRas G12C inhibitor.

16-32 nude/nude, Balb/c nude, or NOD/SCID mice per study were inoculated in the right hind limb with $5\times10^6$ of the indicated cell line or tumor fragment. When tumor volume reached ~200-400 mm$^3$ (Study Day 0), 4 or more mice in each of the four to six groups were administered p.o. daily for 20-42 days: vehicle only (0.5% MC (4000 cps)/ 0.2% Tween80 in water), 10, 30, or 100 mg/kg of KRas G12C inhibitor adagrasib (10% Captisol in 50 mM citrate buffer, pH 5.0), 0.3 mg/kg of the MEK inhibitor VS-6766 (5% DMSO with 10% Hydroxypropyl-β-cyclodextrin in water), 50 or 100 mg/kg of the SOS1 inhibitor (R)-2-methyl-3-(1-((4-methyl-7-morpholinopyrido[3,4-d]pyridazin-1-yl)amino)ethyl)benzonitrile (MRTX-0902) (0.5% MC (4000 cps)/0.2% Tween80 in water), 3-((R)-1-((7-((S)-hexahydropyrazino[2,1-c][1,4]oxazin-8(1H)-yl)-4-methylpyrido[3,4-d]pyridazin-1-yl)amino)ethyl)-2-methylbenzonitrile (MRTX-2006) (20% SBE-β-CD/50 mM citric acid pH 5), or (R)-2-methyl-3-(1-((4-methyl-7-(4-methylpiperazin-1-yl)pyrido[3,4-d]pyridazin-1-yl)amino)ethyl)benzonitrile (MRTX-4197) (20% SBE-β-CD/50 mM citric acid pH 5), or 10, 30, or 100 mg/kg of KRas G12C inhibitor adagrasib and 50 or 100 mg/kg of MRTX-0902, MRTX-2006, or MRTX-4197. An additional combination group with 0.3 mg/kg MEK inhibitor VS-6766 was included for the triple combination study. Tumor volumes, measured at pre-specified days, for the 4-8 mice per group were averaged and are reported for MIA PaCa-2 cells in Tables 1, 2, 3 and 4; LU99 cells in Table 5; NCI-H2122 cells in Tables 6 and 7; CR6256 colorectal patient-derived tumors in Table 8.

TABLE 1

Average Tumor Volumes (mm$^3$) of MIA PaCA-2 Tumor Bearing Mice Treated with Single Agents and in Combination

| Study Day | Vehicle | Adagrasib | MRTX-0902 | Adagrasib + MRTX-0902 Combination |
|---|---|---|---|---|
| 0 | 254 | 252 | 255 | 252 |
| 2 | 337 | 263 | 293 | 201 |
| 6 | 560 | 212 | 452 | 101 |
| 9 | 643 | 192 | 497 | 35 |
| 13 | 882 | 219 | 524 | 17 |
| 16 | 955 | 286 | 584 | 22 |
| 20 | 1091 | 344 | 688 | 24 |
| 23 | 1139 | 410 | 793 | 53 |
| 27 | 1263 | 493 | 884 | 67 |

As shown in FIG. 1 and Table 1, the administration of adagrasib or MRTX-0902 as a single agent exhibited 76.3% and 37.5% tumor growth at Day 27, respectively. The combination of the SOS1 inhibitor MRTX-0902 and adagrasib resulted in −73.4% tumor regression at Day 27.

TABLE 2

Average Tumor Volumes (mm$^3$) of MIA PaCA-2 Tumor Bearing Mice Treated with Single Agents and in Combination

| Study Day | Vehicle | Adagrasib | MRTX-0902 (25 mg/kg BID) | MRTX-0902 (50 mg/kg BID) | Adagrasib + MRTX-0902 (25 mg/kg BID) Combination | Adagrasib + MRTX-0902 (50 mg/kg BID) Combination |
|---|---|---|---|---|---|---|
| 0 | 160 | 158 | 167 | 161 | 165 | 137 |
| 4 | 267 | 81 | 235 | 208 | 48 | 33 |
| 7 | 326 | 88 | 290 | 243 | 40 | 20 |
| 10 | 363 | 110 | 309 | 261 | 53 | 19 |
| 14 | 377 | 125 | 289 | 256 | 38 | 11 |
| 18 | 420 | 171 | 287 | 252 | 45 | 11 |
| 21 | 427 | 162 | 322 | 269 | 46 | 11 |
| 25 | 481 | 181 | 349 | 311 | 76 | 11 |

Figure 2:
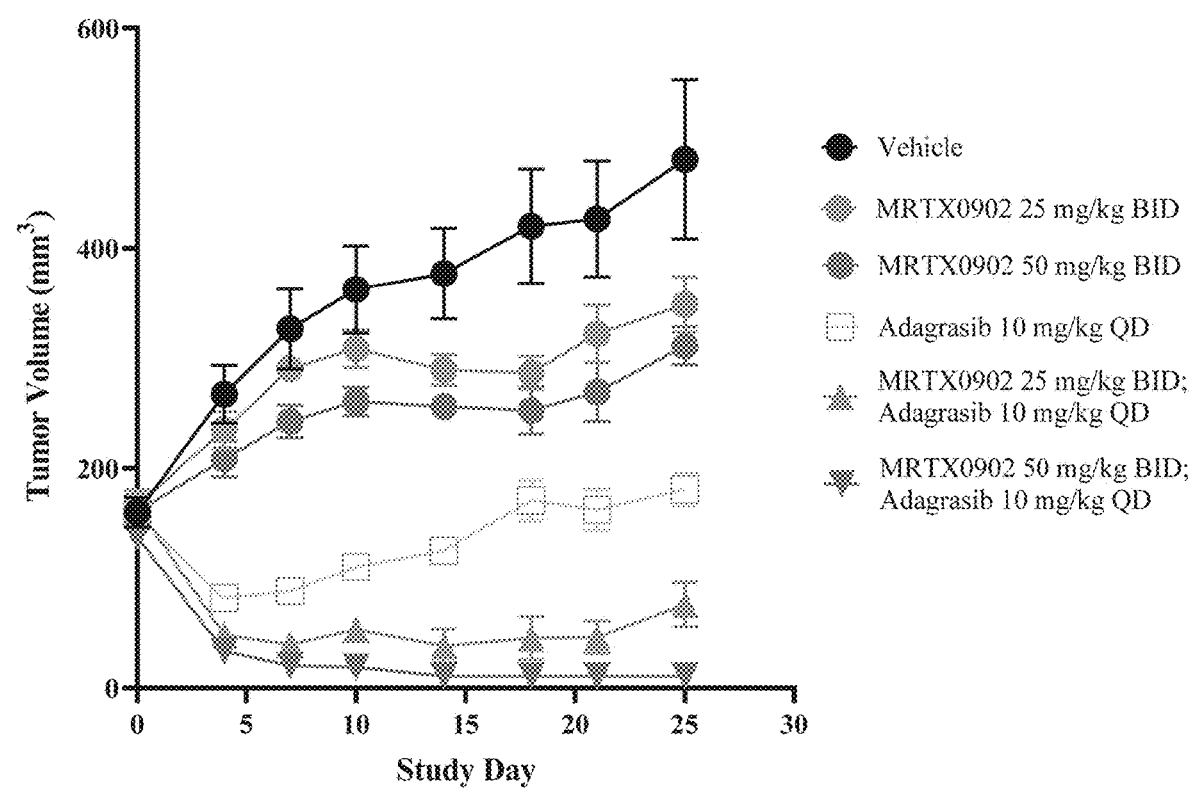
FIG. 2 is a chart of tumor growth inhibition of MIA PaCA-2 tumor bearing mice by MRTX0902, adagrasib, and a combination of MRTX0902 and adagrasib.

As shown in FIG. 2 and Table 2, the administration of single agent adagrasib or 25 and 50 mg/kg BID MRTX-0902 exhibited 93.5%, 41.2%, and 52.9% tumor growth at Day 25, respectively. The combinations of the SOS1 inhibitor MRTX-0902 (25 and 50 mg/kg BID) and adagrasib resulted in −54.1 and −92.1% tumor regression, respectively, at Day 25.

TABLE 3

Average Tumor Volumes (mm³) of MIA PaCA-2 Tumor Bearing Mice Treated with Single Agents and in Combination

| Study Day | Vehicle | Adagrasib | MRTX-2006 | Adagrasib + MRTX-2006 Combination |
|---|---|---|---|---|
| 0 | 165 | 159 | 158 | 152 |
| 4 | 286 | 125 | 218 | 103 |
| 7 | 381 | 95 | 255 | 67 |
| 11 | 551 | 119 | 359 | 72 |
| 15 | 710 | 153 | 493 | 105 |
| 18 | 710 | 191 | 549 | 128 |
| 21 | 816 | 210 | 623 | 112 |
| 25 | 909 | 282 | 710 | 169 |
| 27 | 966 | 346 | 728 | 197 |

Figure 3:
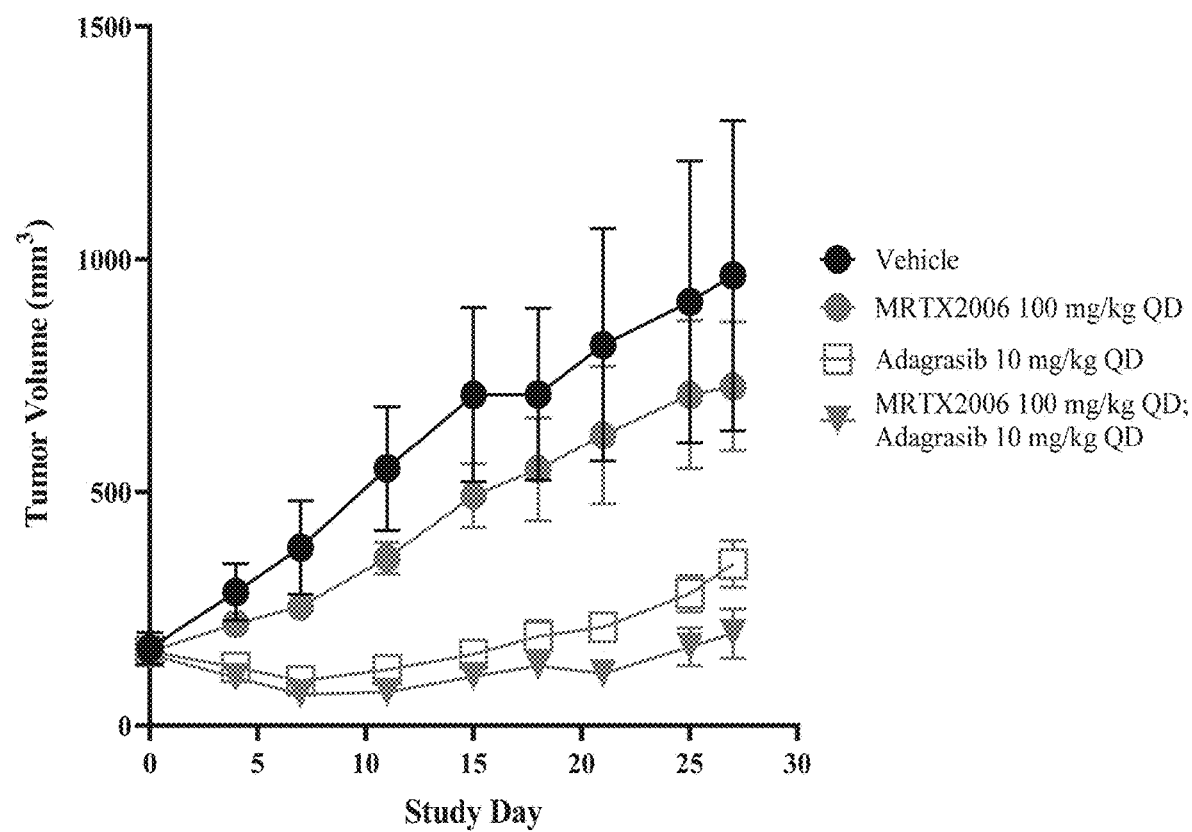
FIG. 3 is a chart of tumor growth inhibition of MIA PaCA-2 tumor bearing mice by MRTX2006, adagrasib, and a combination of MRTX0902 and adagrasib.

As shown in FIG. 3 and Table 3, the administration of adagrasib or MRTX-2006 as a single agent exhibited 77.4% and 29.7% tumor growth at Day 27, respectively. The combination of the SOS1 inhibitor MRTX-2006 and adagrasib resulted in 96.0% tumor growth inhibition at Day 27.

TABLE 4

Average Tumor Volumes (mm³) of MIA PaCA-2 Tumor Bearing Mice Treated with Single Agents and in Combination

| Study Day | Vehicle | Adagrasib | MRTX-4197 | Adagrasib + MRTX-4197 Combination |
|---|---|---|---|---|
| 0 | 254 | 252 | 251 | 248 |
| 2 | 337 | 263 | 279 | 151 |
| 6 | 560 | 212 | 332 | 94 |
| 9 | 643 | 192 | 405 | 43 |
| 13 | 882 | 219 | 397 | 40 |
| 16 | 955 | 286 | 461 | 53 |
| 20 | 1091 | 344 | 438 | 67 |

Figure 4:
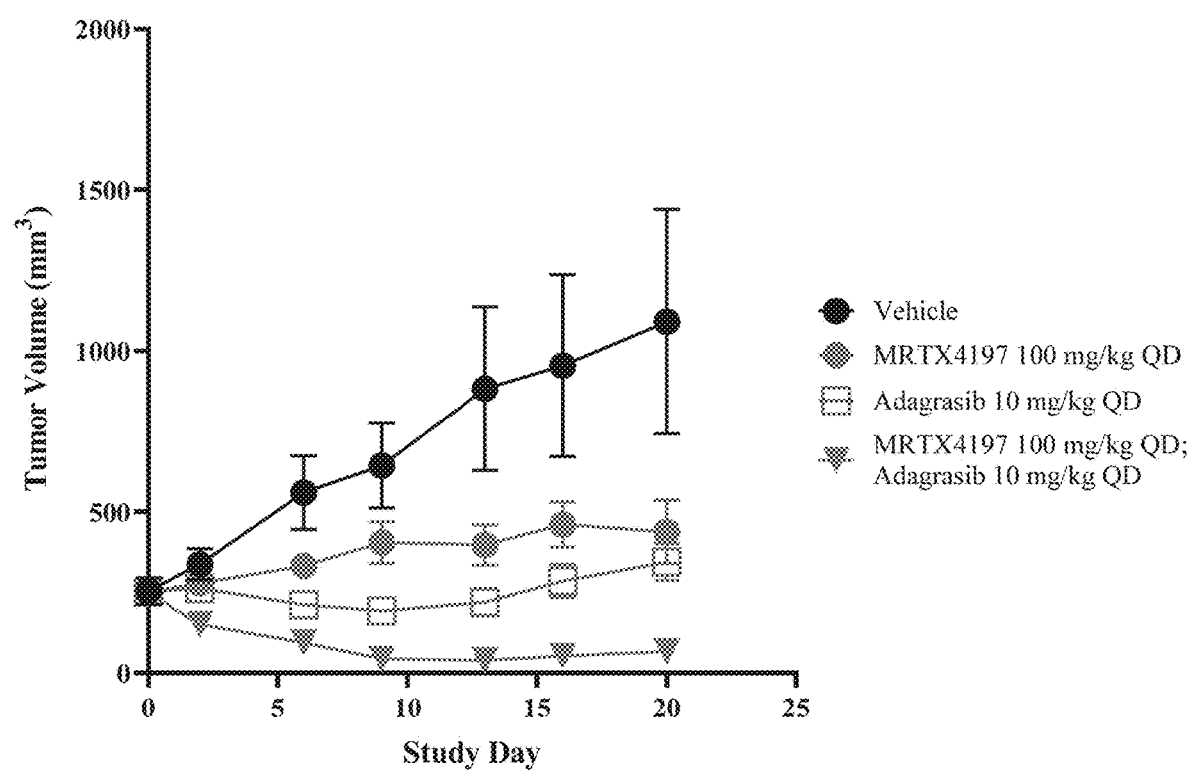
FIG. 4 is a chart of tumor growth inhibition of MIA PaCA-2 tumor bearing mice by MRTX4197, adagrasib, and a combination of MRTX0902 and adagrasib.

As shown in FIG. 4 and Table 4, the administration of adagrasib or MRTX-4197 as a single agent exhibited 89.2% and 78.0% tumor growth at Day 20, respectively. The combination of the SOS1 inhibitor MRTX-4197 and adagrasib resulted in −73.0% tumor regression at Day 28.

TABLE 5

Average Tumor Volumes (mm³) of LU99 Tumor Bearing Mice Treated with Single Agents and in Combination

| Study Day | Vehicle | Adagrasib | MRTX-0902 | Adagrasib + MRTX-0902 Combination |
|---|---|---|---|---|
| 0 | 152 | 154 | 153 | 153 |
| 5 | 180 | 142 | 186 | 110 |
| 8 | 304 | 117 | 224 | 85 |
| 12 | 545 | 87 | 290 | 36 |
| 15 | 718 | 81 | 433 | 17 |
| 20 | 1140 | 84 | 770 | 10 |
| 22 | 1237 | 103 | 976 | 10 |
| 26 | 1548 | 171 | 1249 | 14 |

Figure 5:
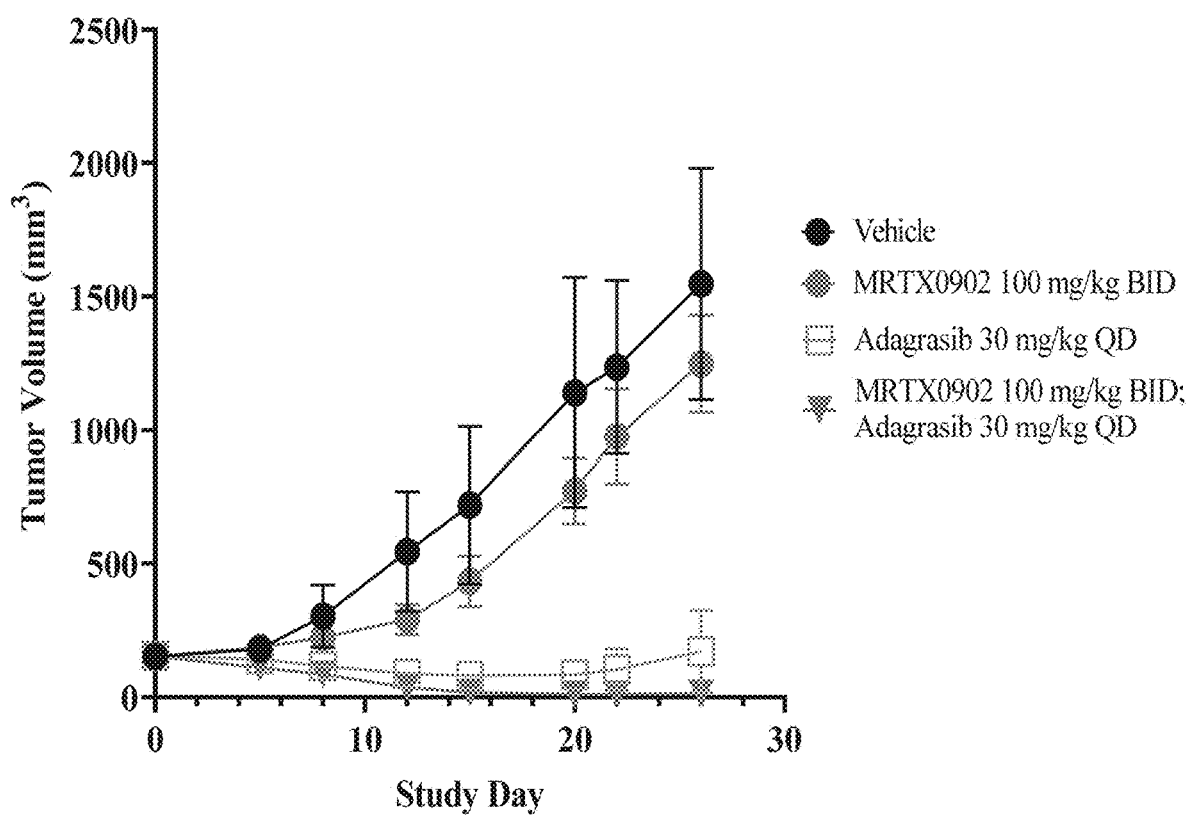
FIG. 5 is a chart of tumor growth inhibition of LU99 tumor bearing mice by MRTX0902, adagrasib, and a combination of MRTX0902 and adagrasib.

As shown in FIG. 5 and Table 5, the administration of adagrasib or MRTX-0902 as a single agent exhibited 98.6% and 21.4% tumor growth at Day 28, respectively. The combination of the SOS1 inhibitor MRTX-0902 and adagrasib resulted in −90.9% tumor regression at Day 26.

TABLE 6

Average Tumor Volumes (mm³) of H2122 Tumor Bearing Mice Treated with Single Agents and in Combination

| Study Day | Vehicle | Adagrasib | MRTX-0902 | Adagrasib + MRTX-0902 Combination |
|---|---|---|---|---|
| 1 | 166 | 169 | 167 | 169 |
| 7 | 818 | 377 | 724 | 339 |
| 10 | 1077 | 350 | 937 | 248 |
| 13 | 1514 | 320 | 1284 | 223 |
| 16 | 1790 | 335 | 1471 | 219 |
| 20 | 1916 | 405 | 1754 | 246 |

Figure 6:
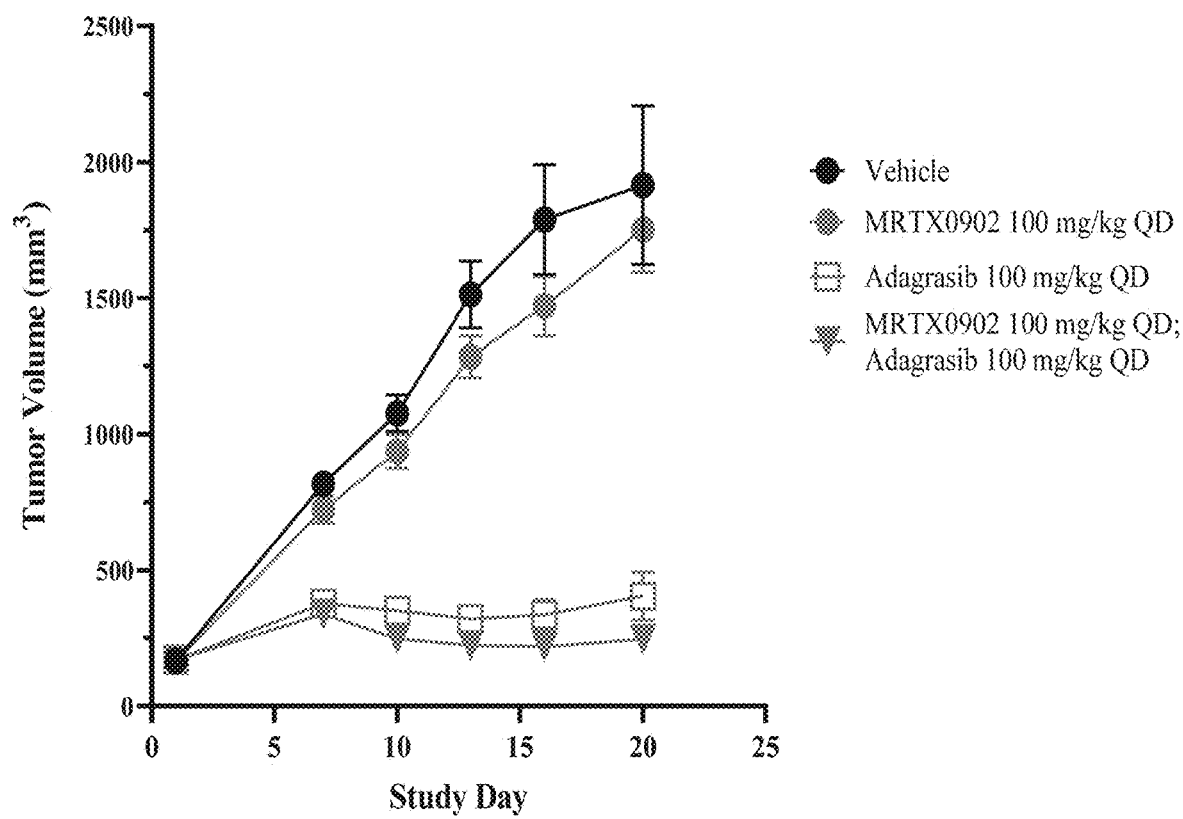
FIG. 6 is a chart of tumor growth inhibition of NCl-H2122 tumor bearing mice by MRTX0902; adagrasib; and a combination of MRTX0902 and adagrasib.

As shown in FIG. 6 and Table 6, the administration of adagrasib or MRTX-0902 as a single agent exhibited 86.3% and 9.2% tumor growth at Day 28, respectively. The combination of the SOS1 inhibitor MRTX-0902 and adagrasib resulted in 95.4% tumor growth inhibition at Day 20.

TABLE 7

Average Tumor Volumes (mm³) of H2122 Tumor Bearing Mice Treated with Single Agents and in Combination

| Study Day | Vehicle | Adagrasib | MRTX-0902 | VS-6766 | Adagrasib + MRTX-0902 + VS-6766 Combination |
|---|---|---|---|---|---|
| −1 | 304 | 306 | 305 | 307 | 309 |
| 2 | 395 | 334 | 430 | 406 | 266 |
| 7 | 564 | 317 | 613 | 415 | 149 |
| 10 | 844 | 360 | 796 | 428 | 125 |
| 13 | 993 | 466 | 933 | 501 | 119 |
| 16 | 1188 | 515 | 1168 | 566 | 131 |
| 20 | 1400 | 535 | 1242 | 592 | 117 |
| 23 | 1571 | 549 | 1410 | 617 | 101 |

Figure 7:
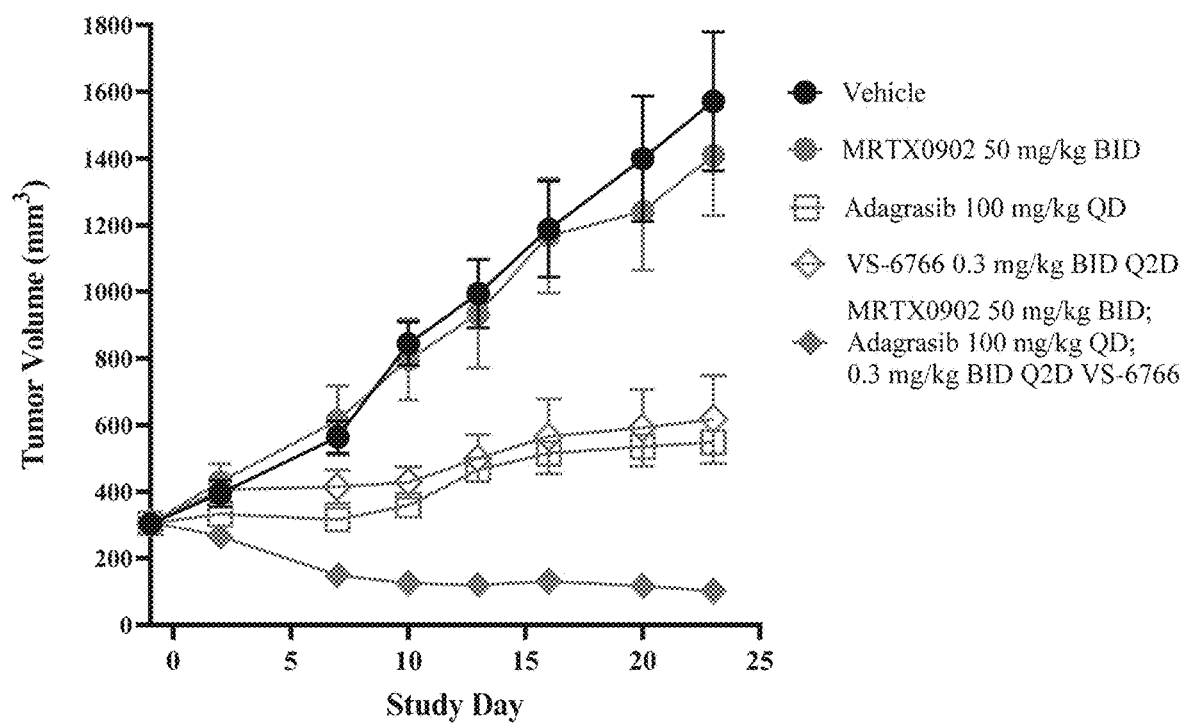
FIG. 7 is a chart of tumor growth inhibition of NCl-H2122 tumor bearing mice by MRTX0902, adagrasib, a combination of MRTX0902 and VS-6766; and a combination of VS-6766 and adagrasib.

As shown in FIG. 7 and Table 7, the administration of adagrasib, MRTX-0902, or VS-6766 as a single agent exhibited 86.9%, 13.7%, and 81.1% tumor growth at Day 23, respectively. The combination of the SOS1 inhibitor MRTX-0902, VS-6766, and adagrasib resulted in −61.9% regression at Day 23.

TABLE 8

Average Tumor Volumes (mm³) of CR6256 Tumor Bearing Mice Treated with Single Agents and in Combination

| Study Day | Vehicle | Adagrasib | MRTX-0902 | Adagrasib + MRTX-0902 Combination |
|---|---|---|---|---|
| 0 | 254 | 254 | 254 | 254 |
| 4 | 455 | 276 | 429 | 241 |
| 7 | 565 | 216 | 579 | 153 |
| 11 | 727 | 189 | 684 | 108 |
| 14 | 837 | 140 | 849 | 74 |
| 18 | 1063 | 152 | 1059 | 60 |
| 21 | 1303 | 168 | 1306 | 73 |
| 25 | 1503 | 164 | 1500 | 76 |
| 28 | 1572 | 160 | 1577 | 72 |
| 32 | 1688 | 156 | 1697 | 43 |
| 35 | 1750 | 178 | 1579 | 38 |
| 39 | 2109 | 220 | 1871 | 62 |
| 42 | 2308 | 276 | 2182 | 50 |

Figure 8:
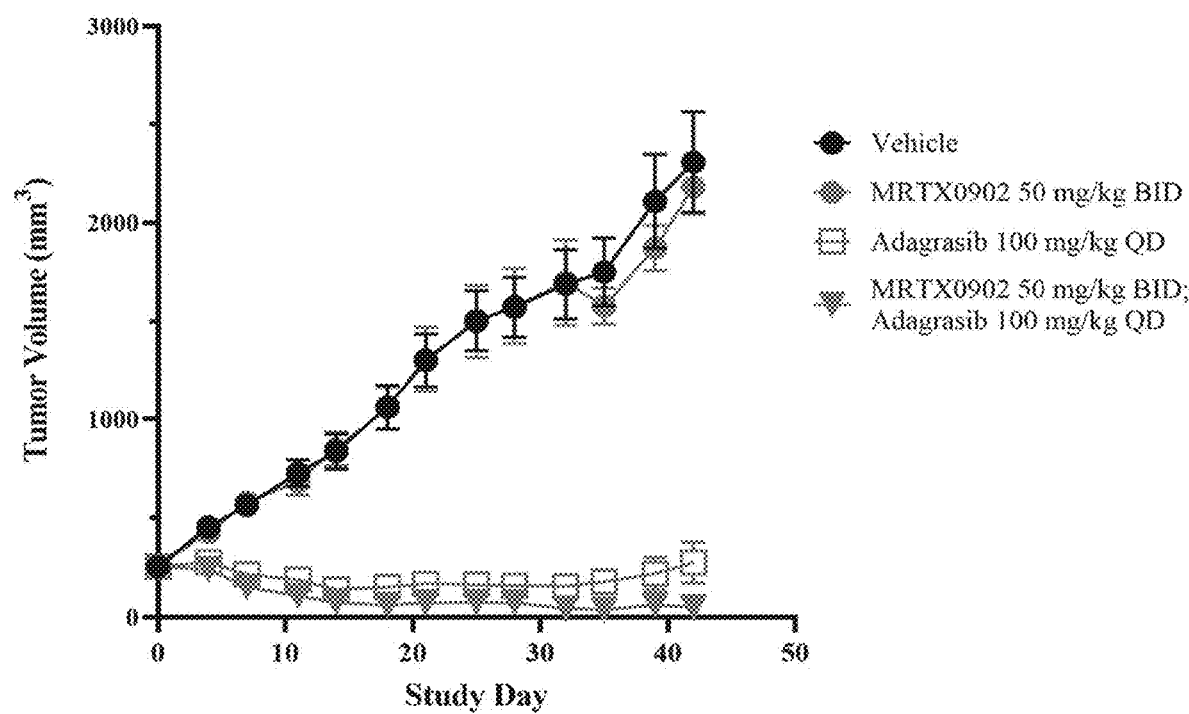
FIG. 8 is a chart of tumor growth inhibition of CR6256 tumor bearing mice by MRTX0902; adagrasib; and a combination of MRTX0902 and adagrasib.

As shown in FIG. 8 and Table 8, the administration of adagrasib or MRTX-0902 as a single agent exhibited 99.0% and 6.1% tumor growth at Day 42, respectively. The combination of the SOS1 inhibitor MRTX-0902 and adagrasib resulted in −80.4% regression at Day 42.

Figure 9:
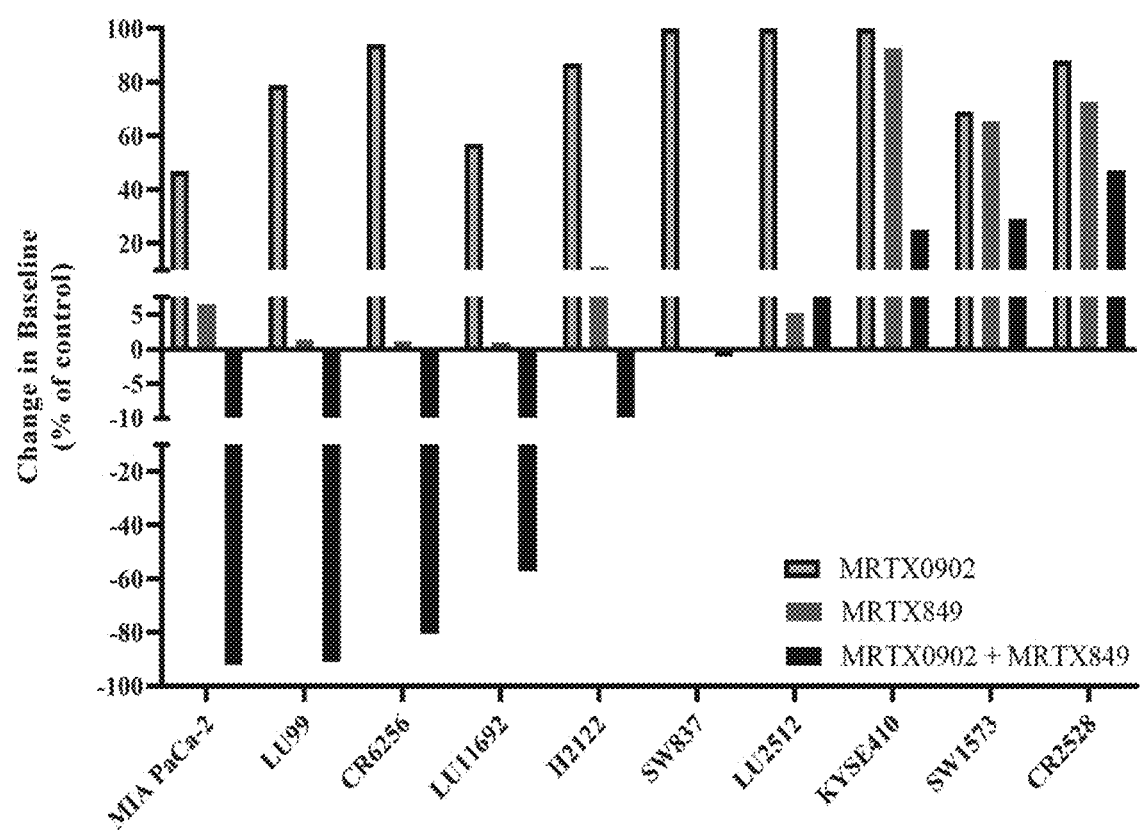
FIG. 9 is a bar chart demonstrating efficacy of a combination of MRTX849 and MRTX0902 in a variety of human tumor xenograft KRas G12C models.

As shown in FIG. 9, the administration of MRTX-0902 with adagrasib leads to broad antitumor activity in KRASG12C-mutant human tumor cell line-derived and patient-derived xenograft models from pancreatic, non-small cell lung, colorectal, and esophageal cancer. These results demonstrate that the combination therapy resulted in greater amount of tumor growth inhibition compared to either single agent alone demonstrating enhanced in vivo anti-tumor efficacy of the combination against KRas G12C expressing cancer.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method of treating cancer in a subject in need thereof, comprising administering to the subject a therapeutically effective amount of a combination of the KRas G12C inhibitor adagrasib:

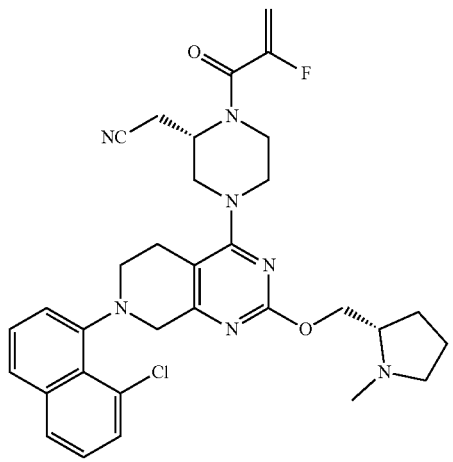 [SMILES: C=C(F)C(=O)N1CCN(c2nc(OC[C@@H]3CCCN3C)nc3c2CCN(c2cccc4cccc(Cl)c24)C3)C[C@@H]1CC#N]

or a pharmaceutically acceptable salt thereof, and a SOS1 inhibitor, wherein the SOS1 inhibitor is

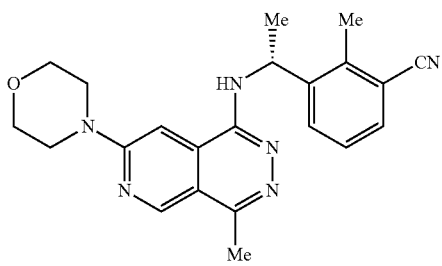 [SMILES: Cc1c(C#N)cccc1[C@@H](C)Nc1nnc(C)c2cnc(N3CCOCC3)cc12]

or a pharmaceutically acceptable salt thereof; wherein the cancer is a KRas G12C-associated cancer selected from the group consisting of lung cancer; gastrointestinal cancer; genitourinary tract cancer; liver cancer; biliary tract cancer; bone cancer; nervous system cancer; gynecological cancer; hematologic cancer; skin cancer; and adrenal glands cancer.

2. The method according to claim 1, wherein the method also comprises administering to the subject in need thereof a compound with the following structure:

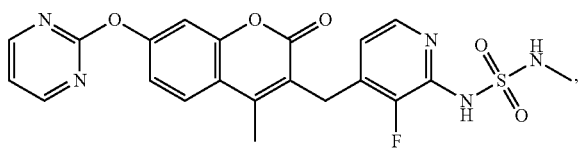 [SMILES: CNS(=O)(=O)Nc1nccc(Cc2c(C)c3ccc(Oc4ncccn4)cc3oc2=O)c1F]

or a pharmaceutically acceptable salt thereof.

3. A method of treating cancer in a subject in need thereof, comprising administering to the subject a therapeutically effective amount of a combination of:
a KRas G12C inhibitor adagrasib:

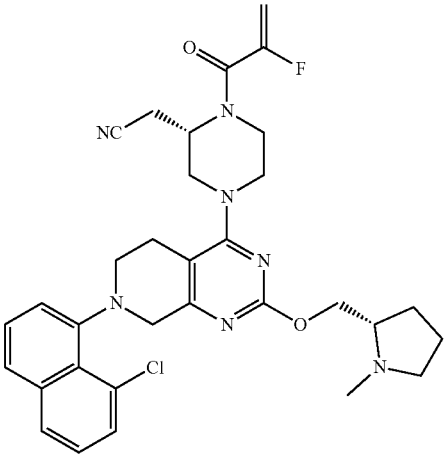 [SMILES: C=C(F)C(=O)N1CCN(c2nc(OC[C@@H]3CCCN3C)nc3c2CCN(c2cccc4cccc(Cl)c24)C3)C[C@@H]1CC#N]

or a pharmaceutically acceptable salt thereof, and
a SOS1 inhibitor:

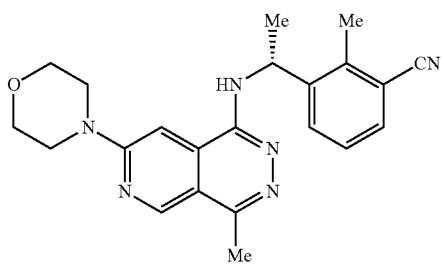 [SMILES: Cc1c(C#N)cccc1[C@@H](C)Nc1nnc(C)c2cnc(N3CCOCC3)cc12]

or a pharmaceutically acceptable salt thereof, and
a MEK inhibitor:

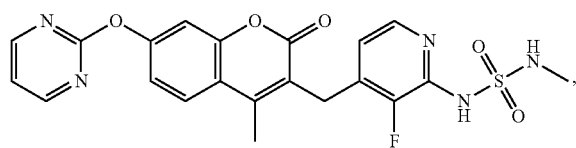 [SMILES: CNS(=O)(=O)Nc1nccc(Cc2c(C)c3ccc(Oc4ncccn4)cc3oc2=O)c1F]

or a pharmaceutically acceptable salt thereof.

4. The method according to claim 1, wherein the SOS1 inhibitor and the KRas G12C inhibitor are administered on the same day.

5. The method according to claim 1, wherein the SOS1 inhibitor and the KRas G12C inhibitor are administered on different days.

6. The method according to claim 1, wherein the KRas G12C inhibitor is administered at a maximum tolerated dose.

7. The method according to claim 1, wherein the SOS1 inhibitor is administered at a maximum tolerated dose.

8. The method according to claim 1, wherein the SOS1 inhibitor and the KRas G12C inhibitor are each administered at a maximum tolerated dose.

9. The method according to claim 1, wherein the KRas G12C inhibitor is administered at below maximum tolerated dose.

10. The method according to claim 1, wherein the SOS 1 inhibitor is administered at below maximum tolerated dose.

11. The method according to claim 1, wherein the SOS1 inhibitor and the KRas G12C inhibitor are each administered at below maximum tolerated dose.

12. The method according to claim 1, wherein the therapeutically effective amount of the combination of the SOS1 inhibitor and the KRas G12C inhibitor results in an increased duration of overall survival, an increased duration of progression free survival, an increase in tumor growth regression, an increase in tumor growth inhibition or an increased duration of stable disease in the subjects relative to treatment with only the KRas G12C inhibitor.

13. The method according to claim 1, wherein the therapeutically effective amount of the combination of the SOS1 inhibitor and the KRas G12C inhibitor results in an increased duration of overall survival, an increased duration of progression free survival, an increase in tumor growth regression, an increase in tumor growth inhibition or an increased duration of stable disease in the subjects relative to treatment with only the SOS1 inhibitor.

14. A method for inhibiting KRas G12C activity in a cell, comprising contacting the cell in which inhibition of KRas G12C activity is desired with an effective amount of a combination of the KRas G12C inhibitor adagrasib:

or a pharmaceutically acceptable salt thereof, and a SOS1 inhibitor, wherein the SOS1 inhibitor is

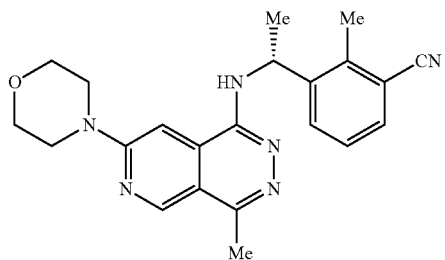 [SMILES: Cc1c(C#N)cccc1[C@@H](C)Nc1nnc(C)c2cnc(N3CCOCC3)cc12]

or a pharmaceutically acceptable salt thereof.

15. The method according to claim 14, further comprising contacting the cell with a compound having the following structure:

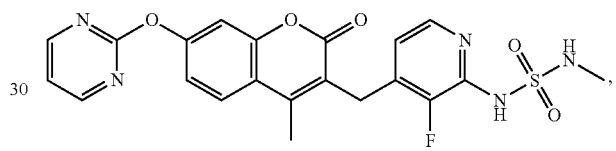

or a pharmaceutically acceptable salt thereof.

16. The method according to claim 1, wherein the SOS1 inhibitor synergistically increases the sensitivity of cancer cells to the KRas G12C inhibitor.

17. A method for increasing the sensitivity of a cancer cell to the KRas G12C inhibitor comprising administering to a subject undergoing KRas G12C treatment with an effective amount of a combination the KRas G12C inhibitor adagrasib:

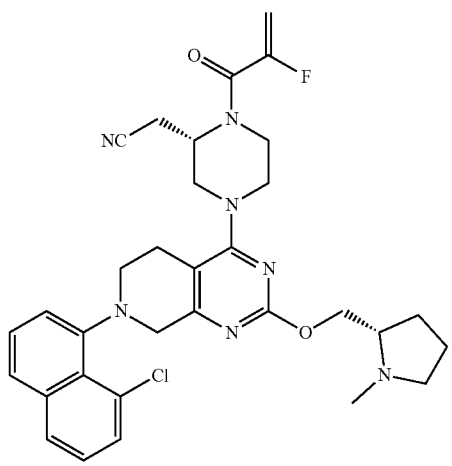 [SMILES: C=C(F)C(=O)N1CCN(c2nc(OC[C@@H]3CCCN3C)nc3c2CCN(c2cccc4cccc(Cl)c24)C3)C[C@@H]1CC#N]

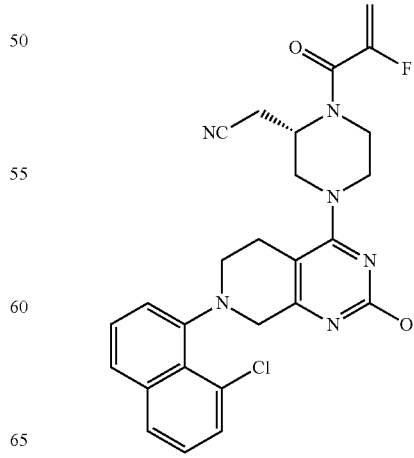

or a pharmaceutically acceptable salt thereof, and a SOS1 inhibitor, wherein the SOS1 inhibitor is

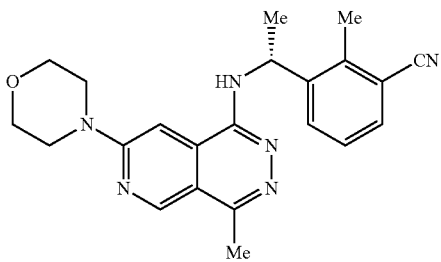 [SMILES: Cc1c(C#N)cccc1[C@@H](C)Nc1nnc(C)c2cnc(N3CCOCC3)cc12]

or a pharmaceutically acceptable salt thereof, and wherein the SOS1 inhibitor synergistically increases the sensitivity of the cancer cell to the KRas G12C inhibitor.

18. The method according to claim 17, wherein the method further comprises administering to the subject in need thereof a compound with the following structure:

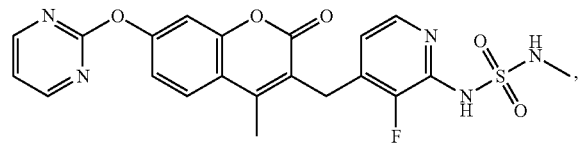 [SMILES: CNS(=O)(=O)Nc1nccc(Cc2c(C)c3ccc(Oc4ncccn4)cc3oc2=O)c1F]

or a pharmaceutically acceptable salt thereof.

19. The method according to claim 1, wherein the therapeutically effective amount of the KRas G12C inhibitor in the combination is between about 0.01 to 100 mg/kg per day.

20. The method according to claim 19, wherein the therapeutically effective amount of the KRas G12C inhibitor in the combination is between about 0.1 to 50 mg/kg per day.

21. The method according to claim 1, wherein the therapeutically effective amount of the SOS1 inhibitor in the combination is between about 0.01 to 100 mg/kg per day.

22. The method according to claim 21, wherein the therapeutically effective amount of the SOS1 inhibitor in the combination is between about 0.1 to 50 mg/kg per day.

23. The method according to claim 1, wherein the lung cancer is non-small cell lung cancer.

24. The method according to claim 1, wherein said cancer is lung cancer.

25. The method according to claim 24, wherein said lung cancer is non small cell lung cancer.

26. The method according to claim 1, wherein said cancer is gastrointestinal cancer.

27. The method according to claim 1, wherein said cancer is genitourinary tract cancer.

28. The method according to claim 1, wherein said cancer is liver cancer.

29. The method according to claim 1, wherein said cancer is biliary tract cancer.

30. The method according to claim 1, wherein said cancer is bone cancer.

31. The method according to claim 1, wherein said cancer is nervous system cancer.

32. The method according to claim 1, wherein said cancer is gynecological cancer.

33. The method according to claim 1, wherein said cancer is hematologic cancer.

34. The method according to claim 1, wherein said cancer is skin cancer or adrenal glands cancer.

* * * * *